(12) United States Patent
Arulanandam et al.

(10) Patent No.: US 7,892,567 B2
(45) Date of Patent: Feb. 22, 2011

(54) METHODS AND COMPOSITIONS FOR IMMUNIZATION AGAINST CHLAMYDIAL INFECTION AND DISEASE

(75) Inventors: Bernard P. Arulanandam, San Antonio, TX (US); Ashlesh K. Murthy, San Antonio, TX (US); Guangming Zhong, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 12/243,769

(22) Filed: Oct. 1, 2008

(65) Prior Publication Data

US 2009/0098165 A1 Apr. 16, 2009

Related U.S. Application Data

(60) Provisional application No. 60/976,636, filed on Oct. 1, 2007.

(51) Int. Cl.
*A61K 39/118* (2006.01)
(52) U.S. Cl. .............. 424/263.1; 424/190.1; 424/193.1; 424/195.11; 424/197.11; 424/203.1
(58) Field of Classification Search ........................ None
See application file for complete search history.

(56) References Cited

U.S. PATENT DOCUMENTS

| 6,746,676 B1 | 6/2004 | Rockey et al. |
| 2006/0034871 A1 | 2/2006 | Grandi et al. |

FOREIGN PATENT DOCUMENTS

| WO | WO 02/079244 A2 | 10/2002 |
| WO | WO 02/082091 A2 | 10/2002 |
| WO | WO 02/082091 A3 | 10/2002 |

OTHER PUBLICATIONS

Greenspan et al (Nature Biotechnology 7: 936-937, 1999).*
Murphy et al. Pediatr. Infect. Dis. J. 1989. 8: S66-S68.*
Yamanaka et al (J. Pediatrics. 1993. 122(2): 212-218).*
Brunham and Rey-Ladino. "Immunology of *Chlamydia* Infection: Implications for a *Chlamydia trachomatis* Vaccine" *Nature Reviews / Immunology* 5:149-161 (2005).
Cong et al. "Intranasal Immunization With Chlamydial Protease-Like Activity Factor and CpG Deoxynucleotides Enhances Protective Immunity Against Genital *Chlamydia muridarum* Infection" *Vaccine* 25:3773-3780 (2007).
Dong et al. "Cleavage-Dependent Activation of a Chlamydia-Secreted Protease" *Molecular Microbiology* 52(5):1487-1494 (2004).
Dong et al. "Cleavage of Host Keratin 8 by a Chlamydia-Secreted Protease" *Infection and Immunity* 72(7):3863-3868 (2004).
Dong et al. "Intramolecular Dimerization is Required for the Chlamydia-Secreted Protease CPAF to Degrade Host Transcriptional Factors" *Infection and Immunity* 72(7):3869-3875 (2004).
Dong et al. "Production of a Proteolytically Active Protein, Chlamydial Protease/Proteasome-Like Activity Factor, by Five Different *Chlamydia* Species" *Infection and Immunity* 73(7):1868-1872 (2005).
Dong et al. Author's Correction to "Production of a Proteolytically Active Protein, Chlamydial Protease/Protesome-Like Activity Factor, by Five Different *Chlamydia* Species" *Infection and Immunity* 73(3):1868-1872 (2005) p. 1872 (1 page).
Genbank Accession No. AAC68456. Hypothetical Protein (*Chlamydia trachomatis*), May 20, 1998 (1 page).
Genbank Accession No. NP_220380. Predicted Protease Containing IRBP and DHR Domains (*Chlamydia trachomatis*), Sep. 10, 2001 (2 pages).
Li et al. "Antigen-Specific CD4+ T Cells Produce Sufficient IFN-γ to Mediate Robust Protective Immunity Against Genital *Chlamydia muridarum* Infection" *The Journal of Immunology* 180:3375-3382 (2008).
Li et al. "Induction of Cross-Serovar Protection Against Genital Chlamydial Infection by a Targeted Multisubunit Vaccination Approach" *Clinical and Vaccine Immunology* 14(12):1537-1544 (2007).
Murphey et al. "The Protective Efficacy of Chlamydial Protease-Like Activity Factor Vaccination is Dependent Upon CD4+ T Cells" *Cell Immunol.* 242(2):110-117 (2006).
Murthy et al. "Chlamydial Protease-Like Activity Factor Induces Protective Immunity Against Genital Chlamydial Infection in Transgenic Mice That Express the Human HLA-DR4 Allele" *Infection and Immunity* 74(12):6722-6729 (2006).
Murthy et al. "Intranasal Vaccination With a Secreted Chlamydial Protein Enhances Resolution of Genital *Chlamydia muridarum* Infection, Protects Against Oviduct Pathology, and is Highly Dependent Upon Endogenous Gamma Interferon Production" *Infection and Immunity* 75(2):666-676 (2007).
Sharma et al. "Human Antibody Responses to a Chlamydia-Secreted Protease Factor" *Infection and Immunity* 72(12):7164-7171 (2004).
Sharma et al. "Inhibition of Proteolytic Activity of a Chlamydial Proteasome/Protease-Like Activity Factor by Antibodies from Humans Infected With *Chlamydia trachomatis*" *Infection and Immunity* 73(7):4414-4419 (2005).
Sharma et al. "Profiling of Human Antibody Responses to *Chlamydia trachomatis* Urogenital Tract Infection Using Microplates Arrayed With 156 Chlamydial Fusion Proteins" *Infection and Immunity* 74(3):1490-1499 (2006).
Stephens et al. "Genome Sequence of an Obligate Intracellular Pathogen of Humans: *Chlamydia trachomatis*" *Science* 282:754-759 (1998).
Zhong et al. "Chlamydia Inhibits Interferon γ-Inducible Major Histocompatibility Complex Class II Expression by Degradation of Upstream Stimulatory Factor 1" *J. Exp. Med.* 189(12):1931-1937 (1999).
Zhong et al. "Degradation of Transcription Factor RFX5 During the Inhibition of Both Constitutive and Interferon γ-Inducible Major Histocompatibility Complex Class I Expression in Chlamydia-Infected Cells" *J. Exp. Med.* 191(9):1525-1534 (2000).
Zhong et al. "Identification of a Chlamydial Protease-Like Activity Factor Responsible for the Degeneration of Host Transcription Factors" *J. Exp. Med.* 193(8):935-942 (2001).

* cited by examiner

*Primary Examiner*—Jennifer E Graser
(74) *Attorney, Agent, or Firm*—Myers Bigel Sibley & Sajovec, P.A.

(57) ABSTRACT

The present invention provides *Chlamydia* proteins and compositions and methods of use in the treatment/prevention of chlamydial infection in a subject, for eliciting an immune response in a subject and for reducing the likelihood of infertility and reducing the incidence and/or degree of hydrosalpinx due to *Chlamydia* infection in a subject.

6 Claims, 7 Drawing Sheets

Fig. 1.

| IFN-γR$^{+/+}$ CD4$^+$ T cells from mice immunized with | Recipient mice | % mice shedding *Chlamydia* (n=6) | | | | | | | | | |
|---|---|---|---|---|---|---|---|---|---|---|---|
| | | Day after i.vag. challenge | | | | | | | | | |
| | | 3 | 6 | 9 | 12 | 15 | 18 | 21 | 24 | 27 | 30 |
| PBS | IFN-γR$^{+/+}$ | 100 | 100 | 100 | 100 | 100 | 83 | 83 | 33 | 0 | 0 |
| PBS | IFN-γR$^{-/-}$ | 100 | 100 | 100 | 100 | 100 | 100 | 100 | 100 | 83 | 50 |
| rCPAF+CpG | IFN-γR$^{+/+}$ | 100 | 100 | 100 | 83 | 50 | 0 | 0 | 0 | 0 | 0 |
| rCPAF+CpG | IFN-γR$^{-/-}$ | 100 | 100 | 100 | 100 | 100 | 100 | 100 | 100 | 83 | 50 |

| Immunization | | % mice shedding chlamydia from the vagina (n=5) | | | | | | | | | |
|---|---|---|---|---|---|---|---|---|---|---|---|
| | | Days after i.vag. challenge | | | | | | | | | |
| | | 3 | 6 | 9 | 12 | 15 | 18 | 21 | 24 | 27 | 30 |
| Mock | $\beta_2 m^{+/+}$ | 100 | 100 | 100 | 100 | 100 | 100 | 100 | 60 | 0 | 0 |
| | $\beta_2 m^{-/-}$ | 100 | 100 | 100 | 100 | 100 | 100 | 100 | 60 | 0 | 0 |
| rCPAF+CpG | $\beta_2 m^{+/+}$ | 100 | 100 | 100 | 100 | 40 | 0 | 0 | 0 | 0 | 0 |
| | $\beta_2 m^{-/-}$ | 100 | 100 | 100 | 100 | 40 | 0 | 0 | 0 | 0 | 0 |

B

| Immunization | | % Mice developing hydrosalpinx (n=5) | |
|---|---|---|---|
| | | Day 80 after *C. muridarum* challenge | |
| | | B | U |
| Mock | $\beta_2 m^{+/+}$ | 80 | 20 |
| | $\beta_2 m^{-/-}$ | 100 | 0 |
| rCPAF+CpG | $\beta_2 m^{+/+}$ | 20 | 0 |
| | $\beta_2 m^{-/-}$ | 20 | 20 |

SEQUENCE LISTING

<160> NUMBER OF SEQ ID NOS: 8

<210> SEQ ID NO 1
<211> LENGTH: 200
<212> TYPE: PRT
<213> ORGANISM: Chlamydia trachomatis

<400> SEQUENCE: 1

Met Gly Phe Trp Arg Thr Ser Ile Met Lys Met Asn Arg Ile Trp Leu
1               5                   10                  15

```
Leu Leu Leu Thr Phe Ser Ser Ala Ile His Ser Pro Val Arg Gly Glu
            20                  25                  30

Ser Leu Val Cys Lys Asn Ala Leu Gln Asp Leu Ser Phe Leu Glu His
        35                  40                  45

Leu Leu Gln Val Lys Tyr Ala Pro Lys Thr Trp Lys Glu Gln Tyr Leu
    50                  55                  60

Gly Trp Asp Leu Val Gln Ser Val Ser Ala Gln Gln Lys Leu Arg
65                  70                  75                  80

Thr Gln Glu Asn Pro Ser Thr Ser Phe Cys Gln Gln Val Leu Ala Asp
                85                  90                  95

Phe Ile Gly Gly Leu Asn Asp Phe His Ala Gly Val Thr Phe Phe Ala
            100                 105                 110

Ile Glu Ser Ala Tyr Leu Pro Tyr Thr Val Gln Lys Ser Ser Asp Gly
        115                 120                 125

Arg Phe Tyr Phe Val Asp Ile Met Thr Phe Ser Ser Glu Ile Arg Val
130                 135                 140

Gly Asp Glu Leu Leu Glu Val Asp Gly Ala Pro Val Gln Asp Val Leu
145                 150                 155                 160

Ala Thr Leu Tyr Gly Ser Asn His Lys Gly Thr Ala Ala Glu Glu Ser
                165                 170                 175

Ala Ala Leu Arg Thr Leu Phe Ser Arg Met Ala Ser Leu Gly His Lys
            180                 185                 190

Val Pro Ser Gly Arg Thr Thr Leu
        195                 200

<210> SEQ ID NO 2
<211> LENGTH: 474
<212> TYPE: PRT
<213> ORGANISM: Chlamydia trachomatis

<400> SEQUENCE: 2

Met Thr Phe Ser Ser Glu Ile Arg Val Gly Asp Glu Leu Leu Glu Val
1               5                   10                  15

Asp Gly Ala Pro Val Gln Asp Val Leu Ala Thr Leu Tyr Gly Ser Asn
            20                  25                  30

His Lys Gly Thr Ala Ala Glu Glu Ser Ala Ala Leu Arg Thr Leu Phe
        35                  40                  45

Ser Arg Met Ala Ser Leu Gly His Lys Val Pro Ser Gly Arg Thr Thr
    50                  55                  60

Leu Lys Ile Arg Arg Pro Phe Gly Thr Thr Arg Glu Val Arg Val Lys
65                  70                  75                  80

Trp Arg Tyr Val Pro Glu Gly Val Gly Asp Leu Ala Thr Ile Ala Pro
                85                  90                  95

Ser Ile Arg Ala Pro Gln Leu Gln Lys Ser Met Arg Ser Phe Phe Pro
            100                 105                 110

Lys Lys Asp Asp Ala Phe His Arg Ser Ser Leu Phe Tyr Ser Pro
        115                 120                 125

Met Val Pro His Phe Trp Ala Glu Leu Arg Asn His Tyr Ala Thr Ser
130                 135                 140

Gly Leu Lys Ser Gly Tyr Asn Ile Gly Ser Thr Asp Gly Phe Leu Pro
145                 150                 155                 160

Val Ile Gly Pro Val Ile Trp Glu Ser Glu Gly Leu Phe Arg Ala Tyr
                165                 170                 175

Ile Ser Ser Val Thr Asp Gly Asp Gly Lys Ser His Lys Val Gly Phe
            180                 185                 190
```

```
Leu Arg Ile Pro Thr Tyr Ser Trp Gln Asp Met Glu Asp Phe Asp Pro
            195                 200                 205

Ser Gly Pro Pro Pro Trp Glu Glu Phe Ala Lys Ile Ile Gln Val Phe
    210                 215                 220

Ser Ser Asn Thr Glu Ala Leu Ile Ile Asp Gln Thr Asn Asn Pro Gly
225                 230                 235                 240

Gly Ser Val Leu Tyr Leu Tyr Ala Leu Leu Ser Met Leu Thr Asp Arg
                245                 250                 255

Pro Leu Glu Leu Pro Lys His Arg Met Ile Leu Thr Gln Asp Glu Val
            260                 265                 270

Val Asp Ala Leu Asp Trp Leu Thr Leu Leu Glu Asn Val Asp Thr Asn
        275                 280                 285

Val Glu Ser Arg Leu Ala Leu Gly Asp Asn Met Glu Gly Tyr Thr Val
    290                 295                 300

Asp Leu Gln Val Ala Glu Tyr Leu Lys Ser Phe Gly Arg Gln Val Leu
305                 310                 315                 320

Asn Cys Trp Ser Lys Gly Asp Ile Glu Leu Ser Thr Pro Ile Pro Leu
                325                 330                 335

Phe Gly Phe Glu Lys Ile His Pro His Pro Arg Val Gln Tyr Ser Lys
            340                 345                 350

Pro Ile Cys Val Leu Ile Asn Glu Gln Asp Phe Ser Cys Ala Asp Phe
        355                 360                 365

Phe Pro Val Val Leu Lys Asp Asn Asp Arg Ala Leu Ile Val Gly Thr
    370                 375                 380

Arg Thr Ala Gly Ala Gly Gly Phe Val Phe Asn Val Gln Phe Pro Asn
385                 390                 395                 400

Arg Thr Gly Ile Lys Thr Cys Ser Leu Thr Gly Ser Leu Ala Val Arg
                405                 410                 415

Glu His Gly Ala Phe Ile Glu Asn Ile Gly Val Glu Pro His Ile Asp
            420                 425                 430

Leu Pro Phe Thr Ala Asn Asp Ile Arg Tyr Lys Gly Tyr Ser Glu Tyr
        435                 440                 445

Leu Asp Lys Val Lys Lys Leu Val Cys Gln Leu Ile Asn Asn Asp Gly
    450                 455                 460

Thr Ile Ile Leu Ala Glu Asp Gly Ser Phe
465                 470

<210> SEQ ID NO 3
<211> LENGTH: 368
<212> TYPE: PRT
<213> ORGANISM: Chlamydia trachomatis

<400> SEQUENCE: 3

Met Arg Ser Phe Phe Pro Lys Lys Asp Asp Ala Phe His Arg Ser Ser
1               5                   10                  15

Ser Leu Phe Tyr Ser Pro Met Val Pro His Phe Trp Ala Glu Leu Arg
            20                  25                  30

Asn His Tyr Ala Thr Ser Gly Leu Lys Ser Gly Tyr Asn Ile Gly Ser
        35                  40                  45

Thr Asp Gly Phe Leu Pro Val Ile Gly Pro Val Ile Trp Glu Ser Glu
    50                  55                  60

Gly Leu Phe Arg Ala Tyr Ile Ser Ser Val Thr Asp Gly Asp Gly Lys
65                  70                  75                  80
```

Ser His Lys Val Gly Phe Leu Arg Ile Pro Thr Tyr Ser Trp Gln Asp
            85                  90                  95

Met Glu Asp Phe Asp Pro Ser Gly Pro Pro Trp Glu Glu Phe Ala
        100                 105                 110

Lys Ile Ile Gln Val Phe Ser Ser Asn Thr Glu Ala Leu Ile Ile Asp
            115                 120                 125

Gln Thr Asn Asn Pro Gly Gly Ser Val Leu Tyr Leu Tyr Ala Leu Leu
130                 135                 140

Ser Met Leu Thr Asp Arg Pro Leu Glu Leu Pro Lys His Arg Met Ile
145                 150                 155                 160

Leu Thr Gln Asp Glu Val Val Asp Ala Leu Asp Trp Leu Thr Leu Leu
                165                 170                 175

Glu Asn Val Asp Thr Asn Val Glu Ser Arg Leu Ala Leu Gly Asp Asn
            180                 185                 190

Met Glu Gly Tyr Thr Val Asp Leu Gln Val Ala Glu Tyr Leu Lys Ser
        195                 200                 205

Phe Gly Arg Gln Val Leu Asn Cys Trp Ser Lys Gly Asp Ile Glu Leu
    210                 215                 220

Ser Thr Pro Ile Pro Leu Phe Gly Phe Glu Lys Ile His Pro His Pro
225                 230                 235                 240

Arg Val Gln Tyr Ser Lys Pro Ile Cys Val Leu Ile Asn Glu Gln Asp
                245                 250                 255

Phe Ser Cys Ala Asp Phe Phe Pro Val Val Leu Lys Asp Asn Asp Arg
            260                 265                 270

Ala Leu Ile Val Gly Thr Arg Thr Ala Gly Ala Gly Gly Phe Val Phe
        275                 280                 285

Asn Val Gln Phe Pro Asn Arg Thr Gly Ile Lys Thr Cys Ser Leu Thr
    290                 295                 300

Gly Ser Leu Ala Val Arg Glu His Gly Ala Phe Ile Glu Asn Ile Gly
305                 310                 315                 320

Val Glu Pro His Ile Asp Leu Pro Phe Thr Ala Asn Asp Ile Arg Tyr
                325                 330                 335

Lys Gly Tyr Ser Glu Tyr Leu Asp Lys Val Lys Lys Leu Val Cys Gln
            340                 345                 350

Leu Ile Asn Asn Asp Gly Thr Ile Ile Leu Ala Glu Asp Gly Ser Phe
        355                 360                 365

<210> SEQ ID NO 4
<211> LENGTH: 325
<212> TYPE: PRT
<213> ORGANISM: Chlamydia trachomatis

<400> SEQUENCE: 4

Gly Tyr Asn Ile Gly Ser Thr Asp Gly Phe Leu Pro Val Ile Gly Pro
1               5                   10                  15

Val Ile Trp Glu Ser Glu Gly Leu Phe Arg Ala Tyr Ile Ser Ser Val
            20                  25                  30

Thr Asp Gly Asp Gly Lys Ser His Lys Val Gly Phe Leu Arg Ile Pro
        35                  40                  45

Thr Tyr Ser Trp Gln Asp Met Glu Asp Phe Asp Pro Ser Gly Pro Pro
    50                  55                  60

Pro Trp Glu Glu Phe Ala Lys Ile Ile Gln Val Phe Ser Ser Asn Thr
65                  70                  75                  80

Glu Ala Leu Ile Ile Asp Gln Thr Asn Asn Pro Gly Gly Ser Val Leu
            85                  90                  95

```
Tyr Leu Tyr Ala Leu Leu Ser Met Leu Thr Asp Arg Pro Leu Glu Leu
            100                 105                 110

Pro Lys His Arg Met Ile Leu Thr Gln Asp Glu Val Val Asp Ala Leu
            115                 120                 125

Asp Trp Leu Thr Leu Leu Glu Asn Val Asp Thr Asn Val Glu Ser Arg
        130                 135                 140

Leu Ala Leu Gly Asp Asn Met Glu Gly Tyr Thr Val Asp Leu Gln Val
145                 150                 155                 160

Ala Glu Tyr Leu Lys Ser Phe Gly Arg Gln Val Leu Asn Cys Trp Ser
                165                 170                 175

Lys Gly Asp Ile Glu Leu Ser Thr Pro Ile Pro Leu Phe Gly Phe Glu
            180                 185                 190

Lys Ile His Pro His Pro Arg Val Gln Tyr Ser Lys Pro Ile Cys Val
            195                 200                 205

Leu Ile Asn Glu Gln Asp Phe Ser Cys Ala Asp Phe Phe Pro Val Val
        210                 215                 220

Leu Lys Asp Asn Asp Arg Ala Leu Ile Val Gly Thr Arg Thr Ala Gly
225                 230                 235                 240

Ala Gly Gly Phe Val Phe Asn Val Gln Phe Pro Asn Arg Thr Gly Ile
                245                 250                 255

Lys Thr Cys Ser Leu Thr Gly Ser Leu Ala Val Arg Glu His Gly Ala
            260                 265                 270

Phe Ile Glu Asn Ile Gly Val Glu Pro His Ile Asp Leu Pro Phe Thr
        275                 280                 285

Ala Asn Asp Ile Arg Tyr Lys Gly Tyr Ser Glu Tyr Leu Asp Lys Val
290                 295                 300

Lys Lys Leu Val Cys Gln Leu Asn Asn Asp Gly Thr Ile Ile Leu Ala
305                 310                 315                 320

Glu Asp Gly Ser Phe
                325

<210> SEQ ID NO 5
<211> LENGTH: 223
<212> TYPE: PRT
<213> ORGANISM: Chlamydia trachomatis

<400> SEQUENCE: 5

Met Leu Thr Asp Arg Pro Leu Glu Leu Pro Lys His Arg Met Ile Leu
1               5                   10                  15

Thr Gln Asp Glu Val Val Asp Ala Leu Asp Trp Leu Thr Leu Leu Glu
            20                  25                  30

Asn Val Asp Thr Asn Val Glu Ser Arg Leu Ala Leu Gly Asp Asn Met
        35                  40                  45

Glu Gly Tyr Thr Val Asp Leu Gln Val Ala Glu Tyr Leu Lys Ser Phe
    50                  55                  60

Gly Arg Gln Val Leu Asn Cys Trp Ser Lys Gly Asp Ile Glu Leu Ser
65                  70                  75                  80

Thr Pro Ile Pro Leu Phe Gly Phe Glu Lys Ile His Pro His Pro Arg
                85                  90                  95

Val Gln Tyr Ser Lys Pro Ile Cys Val Leu Ile Asn Glu Gln Asp Phe
            100                 105                 110

Ser Cys Ala Asp Phe Phe Pro Val Val Leu Lys Asp Asn Asp Arg Ala
        115                 120                 125
```

```
Leu Ile Val Gly Thr Arg Thr Ala Gly Ala Gly Phe Val Phe Asn
    130                 135                 140

Val Gln Phe Pro Asn Arg Thr Gly Ile Lys Thr Cys Ser Leu Thr Gly
145                 150                 155                 160

Ser Leu Ala Val Arg Glu His Gly Ala Phe Ile Glu Asn Ile Gly Val
                165                 170                 175

Glu Pro His Ile Asp Leu Pro Phe Thr Ala Asn Asp Ile Arg Tyr Lys
            180                 185                 190

Gly Tyr Ser Glu Tyr Leu Asp Lys Val Lys Lys Leu Val Cys Gln Leu
        195                 200                 205

Ile Asn Asn Asp Gly Thr Ile Ile Leu Ala Glu Asp Gly Ser Phe
    210                 215                 220

<210> SEQ ID NO 6
<211> LENGTH: 609
<212> TYPE: PRT
<213> ORGANISM: Chlamydia trachomatis

<400> SEQUENCE: 6

Met Gly Phe Trp Arg Thr Ser Ile Met Lys Met Asn Arg Ile Trp Leu
1               5                   10                  15

Leu Leu Leu Thr Phe Ser Ser Ala Ile His Ser Pro Val Arg Gly Glu
            20                  25                  30

Ser Leu Val Cys Lys Asn Ala Leu Gln Asp Leu Ser Phe Leu Glu His
        35                  40                  45

Leu Leu Gln Val Lys Tyr Ala Pro Lys Thr Trp Lys Glu Gln Tyr Leu
    50                  55                  60

Gly Trp Asp Leu Val Gln Ser Val Ser Ala Gln Gln Lys Leu Arg
65                  70                  75                  80

Thr Gln Glu Asn Pro Ser Thr Ser Phe Cys Gln Gln Val Leu Ala Asp
                85                  90                  95

Phe Ile Gly Gly Leu Asn Asp Phe His Ala Gly Val Thr Phe Phe Ala
            100                 105                 110

Ile Glu Ser Ala Tyr Leu Pro Tyr Thr Val Gln Lys Ser Ser Asp Gly
        115                 120                 125

Arg Phe Tyr Phe Val Asp Ile Met Thr Phe Ser Ser Glu Ile Arg Val
    130                 135                 140

Gly Asp Glu Leu Leu Glu Val Asp Gly Ala Pro Val Gln Asp Val Leu
145                 150                 155                 160

Ala Thr Leu Tyr Gly Ser Asn His Lys Gly Thr Ala Ala Glu Glu Ser
                165                 170                 175

Ala Ala Leu Arg Thr Leu Phe Ser Arg Met Ala Ser Leu Gly His Lys
            180                 185                 190

Val Pro Ser Gly Arg Thr Thr Leu Lys Ile Arg Arg Pro Phe Gly Thr
        195                 200                 205

Thr Arg Glu Val Arg Val Lys Trp Arg Tyr Val Pro Glu Gly Val Gly
    210                 215                 220

Asp Leu Ala Thr Ile Ala Pro Ser Ile Arg Ala Pro Gln Leu Gln Lys
225                 230                 235                 240

Ser Met Arg Ser Phe Phe Pro Lys Lys Asp Asp Ala Phe His Arg Ser
                245                 250                 255

Ser Ser Leu Phe Tyr Ser Pro Met Val Pro His Phe Trp Ala Glu Leu
            260                 265                 270

Arg Asn His Tyr Ala Thr Ser Gly Leu Lys Ser Gly Tyr Asn Ile Gly
        275                 280                 285
```

-continued

```
Ser Thr Asp Gly Phe Leu Pro Val Ile Gly Pro Val Ile Trp Glu Ser
    290                 295                 300

Glu Gly Leu Phe Arg Ala Tyr Ile Ser Ser Val Thr Asp Gly Asp Gly
305                 310                 315                 320

Lys Ser His Lys Val Gly Phe Leu Arg Ile Pro Thr Tyr Ser Trp Gln
                325                 330                 335

Asp Met Glu Asp Phe Asp Pro Ser Gly Pro Pro Trp Glu Phe
            340                 345                 350

Ala Lys Ile Ile Gln Val Phe Ser Ser Asn Thr Glu Ala Leu Ile Ile
            355                 360                 365

Asp Gln Thr Asn Asn Pro Gly Gly Ser Val Leu Tyr Leu Tyr Ala Leu
    370                 375                 380

Leu Ser Met Leu Thr Asp Arg Pro Leu Glu Leu Pro Lys His Arg Met
385                 390                 395                 400

Ile Leu Thr Gln Asp Glu Val Val Asp Ala Leu Asp Trp Leu Thr Leu
                405                 410                 415

Leu Glu Asn Val Asp Thr Asn Val Glu Ser Arg Leu Ala Leu Gly Asp
            420                 425                 430

Asn Met Glu Gly Tyr Thr Val Asp Leu Gln Val Ala Glu Tyr Leu Lys
            435                 440                 445

Ser Phe Gly Arg Gln Val Leu Asn Cys Trp Ser Lys Gly Asp Ile Glu
    450                 455                 460

Leu Ser Thr Pro Ile Pro Leu Phe Gly Phe Glu Lys Ile His Pro His
465                 470                 475                 480

Pro Arg Val Gln Tyr Ser Lys Pro Ile Cys Val Leu Ile Asn Glu Gln
                485                 490                 495

Asp Phe Ser Cys Ala Asp Phe Phe Pro Val Val Leu Lys Asp Asn Asp
            500                 505                 510

Arg Ala Leu Ile Val Gly Thr Arg Thr Ala Gly Ala Gly Gly Phe Val
            515                 520                 525

Phe Asn Val Gln Phe Pro Asn Arg Thr Gly Ile Lys Thr Cys Ser Leu
    530                 535                 540

Thr Gly Ser Leu Ala Val Arg Glu His Gly Ala Phe Ile Glu Asn Ile
545                 550                 555                 560

Gly Val Glu Pro His Ile Asp Leu Pro Phe Thr Ala Asn Asp Ile Arg
                565                 570                 575

Tyr Lys Gly Tyr Ser Glu Tyr Leu Asp Lys Val Lys Lys Leu Val Cys
            580                 585                 590

Gln Leu Ile Asn Asn Asp Gly Thr Ile Ile Leu Ala Glu Asp Gly Ser
        595                 600                 605

Phe
```

<210> SEQ ID NO 7
<211> LENGTH: 20
<212> TYPE: DNA
<213> ORGANISM: Artificial
<220> FEATURE:
<223> OTHER INFORMATION: Synthetic oligonucleotide

<400> SEQUENCE: 7
tccatgacgt tcctgacgtt                                               20

<210> SEQ ID NO 8
<211> LENGTH: 20
<212> TYPE: DNA

```
-continued
<213> ORGANISM: Artificial
<220> FEATURE:
<223> OTHER INFORMATION: Synthetic oligonucleotide

<400> SEQUENCE: 8
tccaggactt tcctcaggtt                                              20
```

{# METHODS AND COMPOSITIONS FOR IMMUNIZATION AGAINST CHLAMYDIAL INFECTION AND DISEASE

STATEMENT OF PRIORITY

This application claims the benefit, under 35 U.S.C. §119 (e), of U.S. Provisional Application No. 60/976,636, filed Oct. 1, 2007, the contents of which are incorporated by reference herein in their entirety.

STATEMENT OF GOVERNMENT SUPPORT

The present invention was funded in part by government support under grant number SO6GM008194-24 from the National Institutes of Health. The United States Government has certain rights in this invention.

BACKGROUND OF THE INVENTION

1. Field of the Invention

The present invention relates to treatment/prevention of chlamydial infection and disease.

2. Background Art

*Chlamydia trachomatis* is an obligate intracellular Gram-negative bacterium that is the leading cause of bacterial sexually transmitted disease worldwide. The majority of genital chlamydial infections are initially asymptomatic and untreated, despite the availability of effective antimicrobial therapy, and may lead to severe complications such as pelvic inflammatory disease, ectopic pregnancy and infertility. Additionally, the incidence rates of genital chlamydial infections have increased over the last decade, indicating the need for an effective chlamydial vaccine.

The "chlamydial protease-like activity factor" or "CPAF" protein is a protein secreted by *Chlamydia* which has been shown to cleave host major histocompatibility complex (MHC) transcription factors and keratin-8, which is indicated in survival and expansion within infected cells.

The present invention overcomes previous shortcomings in the art by providing methods and compositions employing CPAF for the treatment and/or prevention of chlamydial infection and disease.

SUMMARY OF THE INVENTION

Provided herein is a method of treating and/or preventing chlamydial infection in a subject, including administering to the subject an effective amount of a chlamydial protease-like activity factor (CPAF) protein or an immunogenic fragment or epitope thereof. In some embodiments, administration includes intranasal administration.

Also provided is a method of treating and/or preventing chlamydial infection in a subject, including administering to the subject a composition including: a) an effective amount of a chlamydial protease-like activity factor (CPAF) protein or an immunogenic fragment or epitope thereof, and b) an effective amount of a different chlamydial protein (i.e., a chlamydial protein or fragment or a combination of chlamydial proteins or fragments that does not include CPAF) (e.g., incA, MOMP, etc.) or immunogenic fragment or epitope thereof and/or an adjuvant (e.g., IL-12, CpG oligodeoxynucleotides, alum, Montanide ISA720, etc.). In some embodiments, the composition further includes a pharmaceutically acceptable carrier. In some embodiments, administration includes intranasal administration.

Further provided is a method of eliciting an immune response in a subject, including administering to the subject an effective amount of a chlamydial protease-like activity factor (CPAF) protein or an immunogenic fragment or epitope thereof. In some embodiments, the immune response includes an active (e.g., a protective) immune response. In some embodiments, the immune response includes a cellular and/or humoral immune response. In some embodiments, the immune response includes a Th1 and/or Th2 immune response.

A method of eliciting an immune response in a subject is also provided herein, including administering to the subject a composition including: a) an effective amount of a chlamydial protease-like activity factor (CPAF) protein or an immunogenic fragment or epitope thereof, and b) an effective amount of a different chlamydial protein or immunogenic fragment or epitope thereof and/or an adjuvant. In some embodiments, the immune response includes an active (e.g., a protective) immune response. In some embodiments, the immune response includes a cellular and/or humoral immune response. In some embodiments, the immune response includes a Th1 and/or Th2 immune response.

Also provided herein are compositions including an isolated chlamydial protease-like activity factor (CPAF) protein or an immunogenic fragment or epitope thereof, either alone or in combination with a different isolated chlamydial protein or an immunogenic fragment or epitope thereof. In some embodiments, the CPAF of fragment thereof of this invention, with our without a different chlamydial protein or fragment thereof, also includes an adjuvant.

Further aspects of the present invention include a method of reducing the likelihood of infertility due to *Chlamydia* infection in a subject, comprising administering to the subject a composition comprising an effective amount of a chlamydial protease-like activity factor (CPAF) protein or an immunogenic fragment or epitope thereof. In some embodiments, the method can further comprise administering an adjuvant to the subject.

Also provided herein is a method of reducing the likelihood of infertility due to *Chlamydia* infection in a subject, comprising administering to the subject a composition comprising: a) an effective amount of a chlamydial protease-like activity factor (CPAF) protein or an immunogenic fragment or epitope thereof, and b) an effective amount of a different chlamydial protein or immunogenic fragment or epitope thereof. In some embodiments, the method can further comprise administering an adjuvant to the subject.

In additional embodiments, the present invention provides a method of reducing the incidence of hydrosalpinx due to *Chlamydia* infection in a subject, comprising administering to the subject a composition comprising an effective amount of a chlamydial protease-like activity factor (CPAF) protein or an immunogenic fragment or epitope thereof.

Furthermore, the present invention provides a method of reducing the incidence of hydrosalpinx due to *Chlamydia* infection in a subject, comprising administering to the subject a composition comprising: a) an effective amount of a chlamydial protease-like activity factor (CPAF) protein or an immunogenic fragment or epitope thereof, and b) an effective amount of a different chlamydial protein or immunogenic fragment or epitope thereof.

BRIEF DESCRIPTION OF THE DRAWINGS

FIG. 1. CPAF-specific $CD4^+$ T cells induce anti-chlamydial immunity in an IFN-γ dependent fashion. Groups of C57BL/6 mice were vaccinated with three doses of rCPAF+}

CpG or PBS (mock). Ten days following the last immunization, CD4+ T cells were purified and transferred ($10^7$ cells/mouse) intraperitoneally (i.p.) into *C. muridarum* challenged recipient IFN-γR$^{-/-}$ or IFN-γR$^{+/+}$ animals (6 mice per group). Vaginal chlamydial shedding was measured every third day after challenge and the percentage of mice shedding bacteria at each time-period is reported. p=0.0001 (Kaplan-Meier Test) for resolution time between IFN-γ R$^{+/+}$ mice receiving CPAF-specific CD4+ T cells and other groups. Results are representative of two independent experiments.

Figure 2:
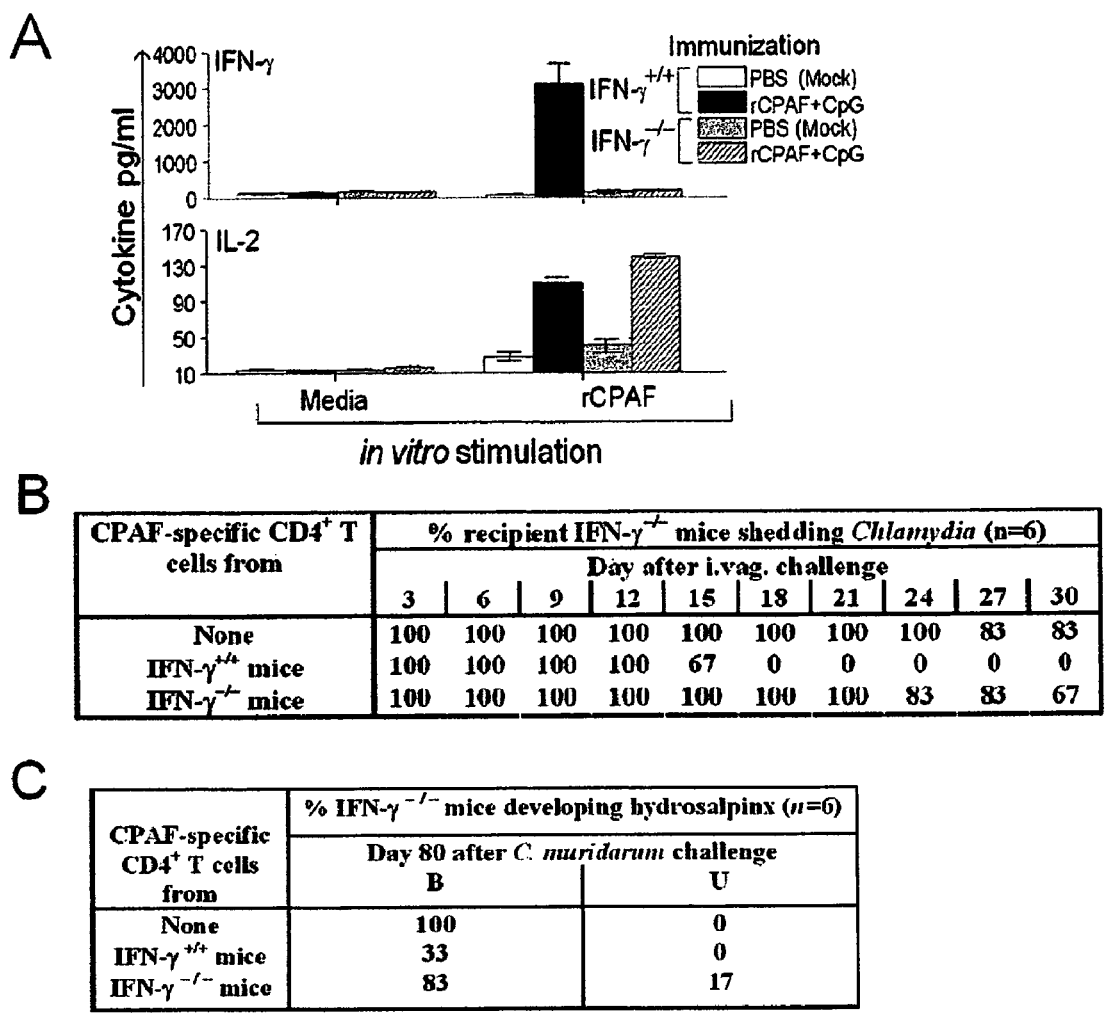

FIGS. 2A-C. CPAF-specific CD4+ T cells are a sufficient source of IFN-γ for resolution of genital chlamydial infection and reduction of oviduct pathology. Groups of IFN-γ$^{-/-}$ mice and IFN-γ$^{+/+}$ mice were immunized with three doses of rCPAF+CpG or PBS (mock). (A) Ag-specific cytokine production. Ten days after the last immunization, some animals (3 mice per group) in each group were euthanized, and splenocytes stimulated in vitro with rCPAF or medium alone. After 72 h incubation, the supernatants were analyzed for IFN-γ and IL-2 production. Results are expressed as mean±SD of cytokine production in each group. (B) Ten days after final immunization, CD4+ T cells were purified from the spleens of vaccinated animals and transferred into *C. muridarum* challenged recipient IFN-γ$^{-/-}$ mice (6 mice per group). One group of IFN-γ$^{-/-}$ mice (6 mice per group) that did not receive cellular transfers was challenged as a control. Vaginal chlamydial shedding was measured every third day after challenge and the percentage of mice shedding bacteria at each time-period is reported. p=0.0009 (Kaplan-Meier test) for resolution time between mice receiving IFN-γ$^{+/+}$ CPAF-specific CD4+ T cells and other groups. (C) On day 80 after chlamydial challenge, the percentage of animals exhibiting hydrosalpinx is reported. p<0.05 (ANOVA) between mice receiving IFN-γ$^{+/+}$ CPAF-specific CD4+ T cells and other groups. B-bilateral, U-unilateral. All results are representative of two independent experiments.

FIGS. 3A-B. MHC II pathway is sufficient for rCPAF+CpG induced anti-chlamydial immunity. Groups of β2m$^{-/-}$ mice and C57BL/6 β2 m$^{+/+}$ mice (5 mice per group) were immunized with three doses of rCPAF+CpG or PBS (mock) and rested for one month. The animals were then challenged intravaginally (i.vag.) with *C. muridarum* ($10^5$ IFU). (A) Chlamydial shedding was analyzed at the indicated time periods. The percentage of animals shedding bacteria at each time-period is reported. (B) On day 80 after chlamydial challenge, the percentage of animals exhibiting hydrosalpinx is reported. B-bilateral, U-unilateral. Results are representative of two independent experiments.

Figure 4:
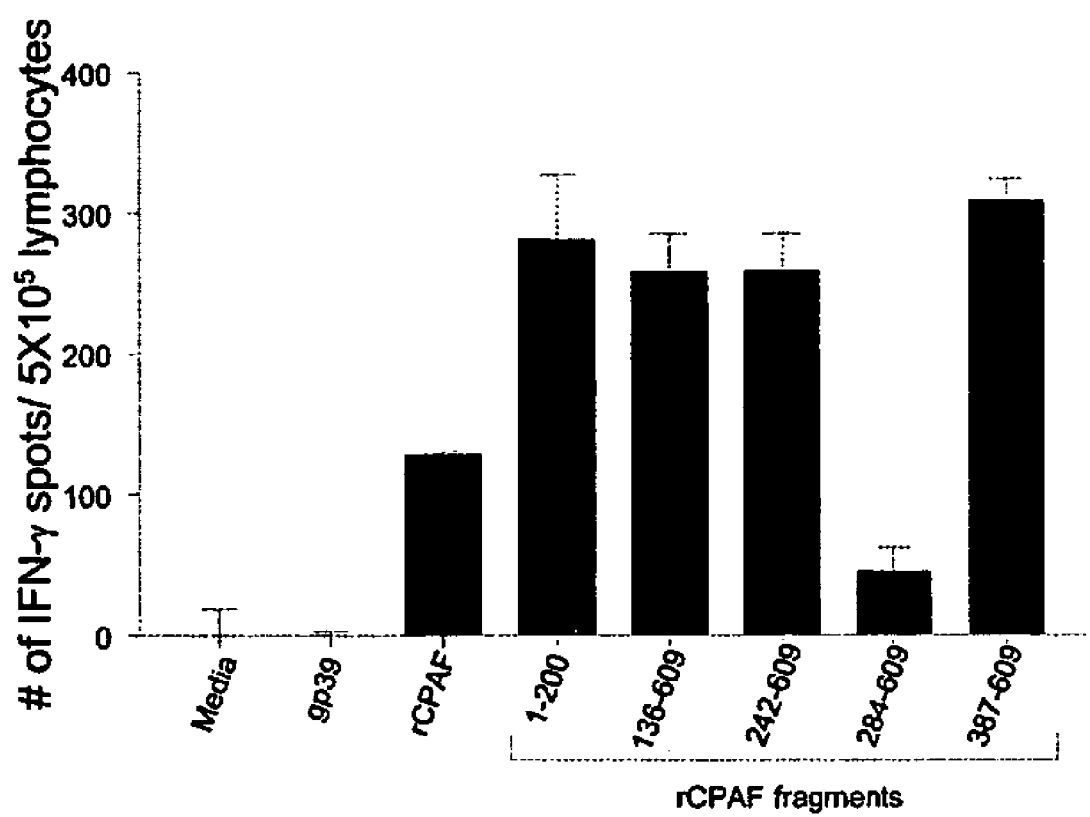

FIG. 4. Cellular response to rCPAF fragments after vaccination in HLA-DR4 tg mice using ELISPOT. HLA-DR4 tg mice (n=3) were injected s.c. using 15 µg of rCPAF with complete Freund's adjuvant (CFA). On day 14, single cell suspensions ($5×10^5$ cells/well) of draining lymph nodes from individual mice were added onto ELISPOT plates pre-incubated with IFN-γ capture antibody and incubated for 24 hrs with full-length rCPAF, or the indicated fragments, or an unrelated antigen, gp39. All cultures were in triplicate and results are expressed as number of IFN-γ spots per $5×10^5$ lymphocytes±standard error of mean. Results are representative of two independent experiments.

Figure 5:
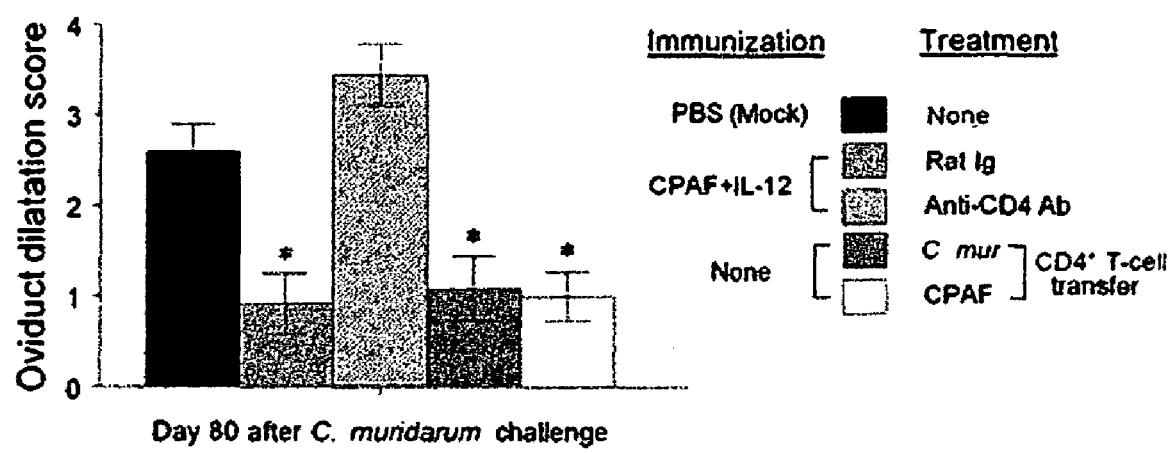

FIG. 5. CPAF-induced protection against genital pathology is dependent on CD4+ T cells. Animals (6 mice/group) were treated with three doses of CPAF+IL-12 or PBS. One month following the final vaccination, mice were challenged i.vag. with 1,500 IFU of *C. muridarum* and CPAF+IL-12 immunized animals were treated either with rat anti-mouse neutralizing anti-CD4 Ab or control rat Ig. Conversely, naïve recipient animals (6 mice/group) were injected with enriched CD4+ T cells ($10^7$ cells/animal) collected from animals 40 days after i.vag. infection with *C. muridarum* (1,500 IFU/animal) or treatment with CPAF+IL-12. The development of oviduct dilatation was scored on day 80 after challenge by microscopic examination and results expressed as means±SEM of the oviduct dilatation scores. * Significant differences between indicated groups and challenged PBS treated group (P<0.05, Kruskall-Wallis test). Results are representative of two independent experiments.

Figure 6:
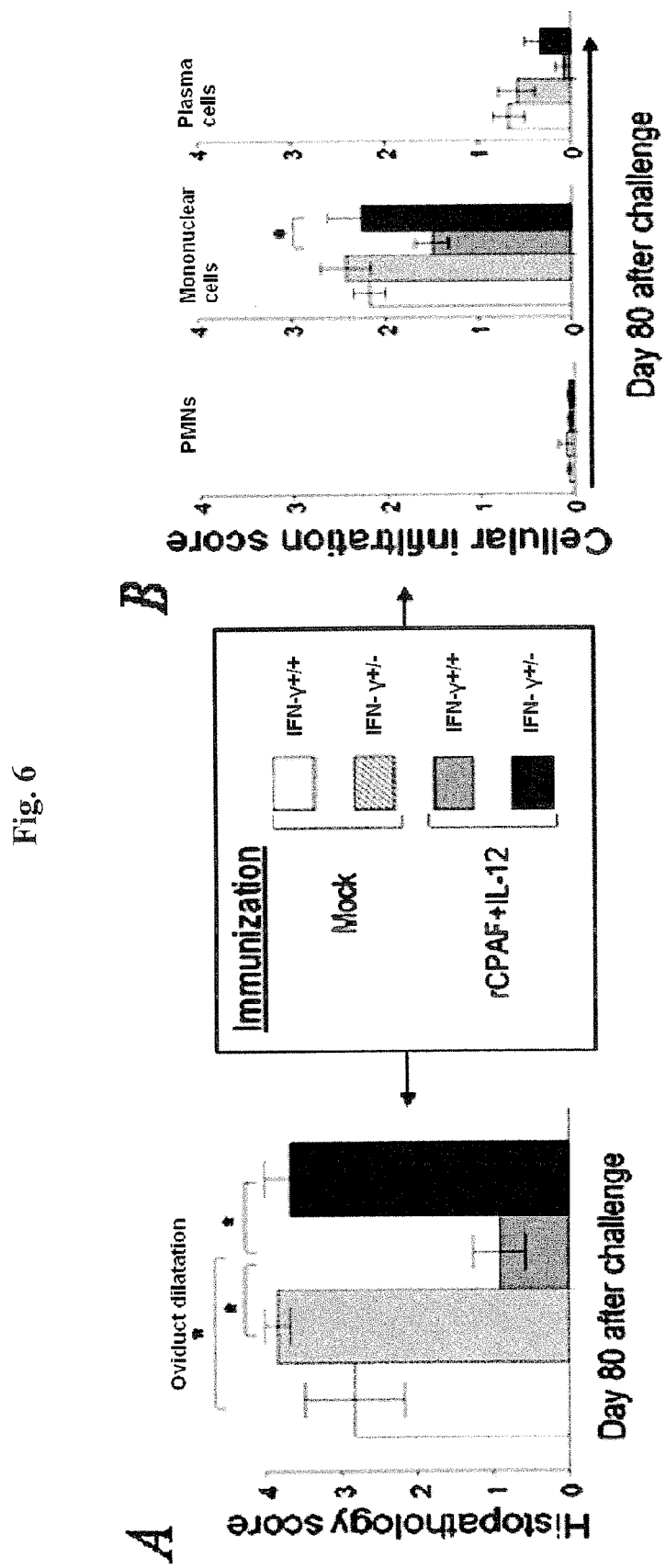

FIGS. 6A-B. IFN-γ is required for prevention of oviduct pathology in *Chlamydia*-challenged rCPAF+IL-12 immunized animals. Animals (8 mice/group) were immunized with 3 doses of rCPAF+IL-12 or PBS (Mock), rested for 1 month, and subsequently challenged i.vag. with $5×10^4$ IFU of *C. muridarum*. At day 80 after challenge, animals (8 mice/group) were euthanized and tissues collected for further analyses. (A) Quantitative histopathological scoring of oviduct dilatation. (B) Quantitative estimation of cellular infiltration into the genital tracts following chlamydial challenge. Means±SEM of histopathology scores are shown. * Significant differences between indicated groups (P<0.05, Kruskall-Wallis test). Results are representative of two independent experiments.

Figure 7:
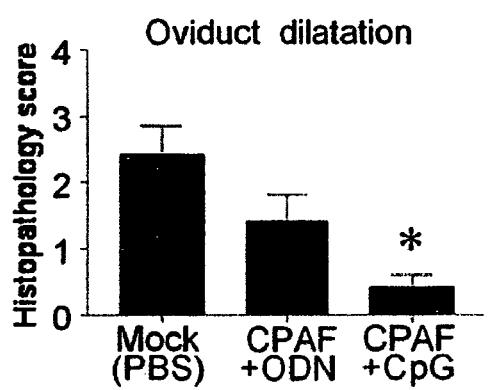
Figure 7:
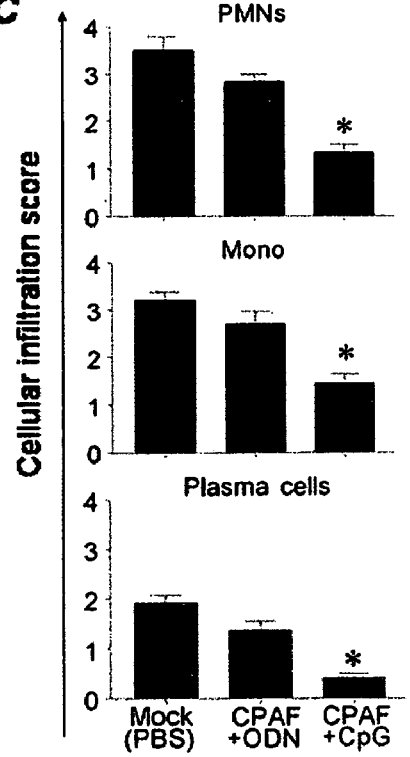

FIGS. 7A-C. CPAF+CpG vaccination reduces the development of oviduct pathology. Animals (6 mice/group) were treated i.n. or i.p. with three doses of CPAF+CpG, CPAF+ODN, or PBS. One month following final vaccination, mice were challenged i.vag. with $5×10^4$ IFU of *C. muridarum*. At day 80 following challenge, animals were euthanized and tissues collected for further analysis. (A) Percentage of animals developing hydrosalpinx in different immunization groups after genital chlamydial challenge: B-bilateral and U-unilateral. (B) Quantitative histopathological scoring of oviduct dilatation. (C) Quantitative estimation of cellular infiltration into the genital tracts following chlamydial challenge. Means±SD of histopathology and cellular infiltration scores are shown. * Significant differences between CPAF+CpG and mock-immunized (PBS) animals (P<0.05, Mann-Whitney Rank-Sum test). Results are representative of two independent experiments.

DETAILED DESCRIPTION OF THE INVENTION

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

As used herein, the term "consists essentially of" (and grammatical variants) means that an immunogenic composition of this invention comprises no other material immunogenic agent other than the indicated agents. The term "consists essentially of" does not exclude the presence of other components in the composition such as adjuvants, immunomodulators, and the like.

The present invention is directed to the use of CPAF, alone or in combination with other immunogens and/or adjuvants for eliciting an immune response in a subject to treat and/or prevent chlamydial infection and/or to ameliorate the pathological conditions associated with chlamydial infection.

Thus, in some embodiments, the present invention provides a method of treating and/or preventing chlamydial infection in a subject, comprising administering to the subject an effective amount of a chlamydial protease-like activity factor (CPAF) protein or an immunogenic fragment or epitope thereof.

In further embodiments, the present invention provides a method of treating and/or preventing chlamydial infection in a subject, comprising administering to the subject a composition comprising: a) an effective amount of a chlamydial protease-like activity factor (CPAF) protein or an immunogenic fragment or epitope thereof, and b) an effective amount of a different chlamydial protein or immunogenic fragment or epitope thereof and/or an adjuvant.

Further provided herein is a method of eliciting an immune response in a subject, comprising administering to the subject an effective amount of a chlamydial protease-like activity factor (CPAF) protein or an immunogenic fragment or epitope thereof.

Additionally, the present invention provides a method of eliciting an immune response in a subject, comprising administering to the subject a composition comprising: a) an effective amount of a chlamydial protease-like activity factor (CPAF) protein or an immunogenic fragment or epitope thereof, and b) an effective amount of a different chlamydial protein or immunogenic fragment or epitope thereof and/or an adjuvant.

Further embodiments of the present invention include a method of reducing the likelihood of infertility due to *Chlamydia* infection in a subject, comprising administering to the subject a composition comprising an effective amount of a chlamydial protease-like activity factor (CPAF) protein or an immunogenic fragment or epitope thereof. The method can further comprise administering an adjuvant to the subject.

Also provided herein is a method of reducing the likelihood of infertility due to *Chlamydia* infection in a subject, comprising administering to the subject a composition comprising: a) an effective amount of a chlamydial protease-like activity factor (CPAF) protein or an immunogenic fragment or epitope thereof, and b) an effective amount of a different chlamydial protein or immunogenic fragment or epitope thereof. The method can further comprise administering an adjuvant to the subject.

By "reducing the likelihood of infertility due to *Chlamydia* infection" is meant that a subject of this invention to whom the immunogenic compositions of this invention are administered is prevented from becoming infertile as a result of *Chlamydia* infection or that the likelihood that the subject will become infertile as a result of being infected by *Chlamydia* is reduced as compared to the likelihood that an untreated subject will become infertile as a result of being infected by *Chlamydia*. That infertility is prevented or its likelihood as a result of *Chlamydia* infection is reduced in a subject can be determined according to protocols described herein and as would be well known in the art.

Hydrosalpinx is a result of tubal blockade and subsequent retention of fluid exudate within the tubal lumen. Given that the patency of oviducts is important to allow fertilization of the ovum and sperm, and that the hydrosalpinx fluid is toxic to the ovum, the presence of hydrosalpinx serves as an indirect marker of infertility. Additionally provided herein are data that provide a direct demonstration of the preservation of fertility in CPAF+CpG vaccinated animals.

Thus, the present invention further provides a method of reducing the incidence of hydrosalpinx due to *Chlamydia* infection in a subject, comprising administering to the subject a composition comprising an effective amount of a chlamydial protease-like activity factor (CPAF) protein or an immunogenic fragment or epitope thereof. The method can further comprise administering an adjuvant to the subject.

Also provided herein is a method of reducing the incidence of hydrosalpinx due to *Chlamydia* infection in a subject, comprising administering to the subject a composition comprising: a) an effective amount of a chlamydial protease-like activity factor (CPAF) protein or an immunogenic fragment or epitope thereof, and b) an effective amount of a different chlamydial protein or immunogenic fragment or epitope thereof. The method can further comprise administering an adjuvant to the subject.

By "reducing the incidence of hydrosalpinx due to *Chlamydia* infection" is meant that a subject of this invention to whom the immunogenic compositions of this invention are administered will be prevented from or protected against developing hydrosalpinx due to *Chlamydia* infection or has a reduced likelihood of developing hydrosalpinx due to *Chlamydia* infection or has a lesser degree of hydrosalpinx due to *Chlamydia* infection as compared to an untreated subject infected by *Chlamydia*. That hydrosalpinx due to *Chlamydia* infection is prevented or its incidence and/or degree are reduced in a subject can be determined according to protocols described herein and as would be well known in the art.

In some embodiments, the CPAF protein or immunogenic fragment or epitope thereof and other chlamydial proteins or immunogenic fragments or epitopes thereof of this invention can be administered to a subject of this invention as a protein or peptide to elicit an immune response to treat and/or prevent chlamydial infections and/or to reduce the likelihood of infertility due to *Chlamydia* infection. In other embodiments, a nucleic acid or multiple nucleic acids encoding a CPAF protein or immunogenic fragment or epitope thereof and other (i.e., different) chlamydial proteins or immunogenic fragments or epitopes thereof of this invention in any combination can be administered to a subject of this invention to elicit an immune response to treat and/or prevent chlamydial infection and/or reduce the likelihood of infertility due to *Chlamydia* infection.

In embodiments of this invention wherein one or more nucleic acids are administered to a subject, the nucleic acid(s) can be present as naked nucleic acid and/or in a vector or plasmid that carries the nucleic acid(s). The nucleic acid(s) and/or vectors and/or plasmids can also be in a cell (e.g., an isolated cell) that is administered to a subject.

Thus, in particular embodiments, a nucleic acid encoding a *Chlamydia* protein or immunogenic fragment thereof of this invention can be introduced into a subject, wherein the nucleic acid is expressed and the encoded product is produced to elicit an immune response in the subject, thereby treating or preventing a *Chlamydia* infection and/or disease.

Examples of different *Chlamydia* proteins or fragments or epitopes thereof, besides CPAF, that can be used in combination with CPAF in the methods of the present invention include, but are not limited to, *Chlamydia trachomatis* proteins such as major outer membrane protein (rMOMP), inclusion membrane protein A (rIncA), etc., as are known in the art. Other examples include, but are not limited to, PorB (Ifere et al., *J. Microbiol. Immunol. Infect.* 40:188-200 (2007))), enolase (Finco et al. *Vaccine* 23:1178-1188 (2005)) Cta1 (Roan et al. PNAS 103:12069-74 (2006)), *Chlamydia trachomatis* proteins CH089 (CopN), (b) CT147 (EEA homology), CT226 (Inc), CT442 (15 kDa Crp), CT443 (60 kDa CRP, OmcB), CT529 (Inc, CapA), CT694 (HP, IB), CT795

(HP, IB), CT806, (j) CT812 (pmpD), CT813 (Inc), CT823, CT841, pCT03, CT110 (HSP60), *Chlamydia trachomatis* CT806 protein, CT823 protein, CT841 protein, pCT03 protein CT813 protein, a homologue of a CT806, CT823, CT841, pCT03 or CT813 protein from a different *Chlamydia* species, TroA, TroB, IncA, IncB and IncC (see, e.g., U.S. Pat. No. 6,746,676 to Rockey et al. and U.S. Patent Application Publication No. 2006/0034871 to Grandi et al., each of which is incorporated by reference herein), as well as any combination thereof. A protein or immunogenic fragment and/or epitope thereof of this invention can be any protein or immunogenic fragment or epitope thereof from *Chlamydia trachomatis, Chlamydia muridarum, Chlamydia pneumoniae Chlamydia psittaci, Chlamydophila abortus* and/or *Chlamydia caviae* in any combination. A CPAF protein or immunogenic fragment and/or epitope thereof of this invention can be from any species of *Chlamydia, Chlamydophila* and/or *Parachlamydia* that produces CPAF. These different chlamydial immunogens (e.g., protein, peptide and/or immunogenic fragment and/or epitope thereof) can be provided with CPAF in any combination and in any ratio with respect to CPAF and/or other chlamydial proteins and/or immunogenic fragments and/or epitopes thereof that may be present.

The polypeptides, immunogenic fragments and/or epitopes of this invention can be modified according to art-known methods and/or administered in an adjuvant in order to increase antigenicity. Methods of increasing the antigenicity of a protein or peptide are well known in the art and include, but are not limited to, coupling the antigen with a heterologous protein (such as globulin or β-galactosidase) or through the inclusion of one or more adjuvants in addition to the immunogen of this invention. The adjuvant can be administered with the immunogen, before administration of the immunogen, after administration of the immunogen, or any combination thereof.

Thus, the compositions employed in the methods of this invention can comprise, consist essentially of and/or consist of a CPAF protein and/or immunogenic fragment and/or epitope thereof either alone or in combination with a different chlamydial protein and/or immunogenic fragment and or epitope thereof of this invention, as well as nucleic acids encoding the chlamydial proteins and/or immunogenic fragments and/or epitopes of this invention and can further comprise, consist essentially of and/or consist of an adjuvant.

In some embodiments, such compositions can further comprise one or more than one adjuvant in the form of an amino acid sequence, and/or in the form or a nucleic acid encoding an adjuvant. The adjuvant, in the form of an amino acid sequence, can be a component of the different chlamydial and/or CPAF polypeptide or fragment or epitope thereof and/ or a separate component of the composition comprising the different chlamydial polypeptide or fragment or epitope thereof and/or CPAF polypeptide or fragment or epitope thereof of this invention. When in the form of a nucleic acid, the adjuvant can be a component of a nucleic acid encoding the polypeptide(s) or fragment(s) or epitope(s) and/or a separate component of the composition comprising the nucleic acid encoding the polypeptide(s) or fragment(s) or epitope(s) of this invention. An adjuvant of this invention can be an amino acid sequence that is a peptide, a protein fragment or a whole protein that functions as an adjuvant, and/or the adjuvant can be a nucleic acid encoding a peptide, protein fragment or whole protein that functions as an adjuvant. As used herein, "adjuvant" describes a substance, which can be any immunomodulating substance capable of being combined with the polypeptide and/or nucleic acid compositions of this invention to enhance, improve or otherwise modulate an immune response in a subject without deleterious effect on the subject.

In further embodiments, an adjuvant of this invention can be, but is not limited to, an immunostimulatory cytokine (including, but not limited to, GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules), SYNTEX adjuvant formulation 1 (SAF-1) composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Suitable adjuvants also include an aluminum salt such as aluminum hydroxide gel (alum), aluminum phosphate, or algannmulin, but may also be a salt of calcium, iron or zinc, and/or may be an insoluble suspension of acylated tyrosine, or acylated sugars, cationically or anionically derivatized polysaccharides, or polyphosphazenes.

Other adjuvants are well known in the art and include MF 59, LT-K63, LT-R72 (Pal et al., *Vaccine* 24(6):766-75 (2005)), QS-21, Freund's adjuvant (complete and incomplete), aluminum hydroxide, N-acetyl-muramyl-L-threonyl-D-isoglutamine (thr-MDP), N-acetyl-normuramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/Tween 80 emulsion.

Additional adjuvants can include, for example, a combination of monophosphoryl lipid A, preferably 3-de-O-acylated monophosphoryl. lipid A (3D-MPL) together with an aluminum salt. An enhanced adjuvant system involves the combination of a monophosphoryl lipid A and a saponin derivative, particularly the combination of QS21 and 3D-MPL as disclosed in PCT publication number WO 94/00153 (the entire contents of which are incorporated herein by reference), or a less reactogenic composition where the QS21 is quenched with cholesterol as disclosed in PCT publication number WO 96/33739 (the entire contents of which are incorporated herein by reference). A particularly potent adjuvant formulation involving QS21 3D-MPL & tocopherol in an oil in water emulsion is described in PCT publication number WO 95/17210 (the entire contents of which are incorporated herein by reference). In addition, the nucleic acid of this invention can include an adjuvant by comprising a nucleotide sequence encoding an antigen of this invention and a nucleotide sequence that provides an adjuvant function, such as CpG sequences. Such CpG sequences, or motifs, are well known in the art.

An adjuvant of this invention, such as, for example, an immunostimulatory cytokine, can be administered before, concurrent with, and/or within a few hours, several hours, and/or 1, 2, 3, 4, 5, 6, 7, 8, 9, and/or 10 days before and/or after the administration of an immunogenic chlamydial composition of this invention to a subject.

Furthermore, any combination of adjuvants, such as immunostimulatory cytokines, can be co-administered to the subject before, after and/or concurrent with the administration of an immunogenic chlamydial composition of this invention. For example, combinations of immunostimulatory cytokines, can consist of two or more immunostimulatory cytokines of this invention, such as GM/CSF, interleukin-2, interleukin- 12, interferon-gamma, interleukin-4, tumor necrosis factor-alpha, interleukin-1, hematopoietic factor flt3L, CD40L, B7.1 co-stimulatory molecules and B7.2 co-stimulatory molecules. The effectiveness of an adjuvant or combination of adjuvants can be determined by measuring the immune response produced in response to administration of a composition of this invention to a subject with and without the adjuvant or combination of adjuvants, using standard procedures, as described herein and as known in the art.

Pharmaceutical compositions comprising the immunogenic chlamydial proteins, fragments and or epitopes of this invention and a pharmaceutically acceptable carrier are also provided. The compositions described herein can be formulated for administration in a pharmaceutical carrier in accordance with known techniques. See, e.g., Remington, *The Science And Practice of Pharmacy* (latest edition). In the manufacture of a pharmaceutical composition according to embodiments of the present invention, the composition of this invention is typically admixed with, inter alia, a pharmaceutically acceptable carrier. By "pharmaceutically acceptable carrier" is meant a carrier that is compatible with other ingredients in the pharmaceutical composition and that is not harmful or deleterious to the subject. The carrier may be a solid or a liquid, or both, and is preferably formulated with the composition of this invention as a unit-dose formulation, for example, a tablet, which may contain from about 0.01 or 0.5% to about 95% or 99% by weight of the composition. The pharmaceutical compositions are prepared by any of the well-known techniques of pharmacy including, but not limited to, admixing the components, optionally including one or more accessory ingredients. In certain embodiments, the pharmaceutically acceptable carrier is sterile and would be deemed suitable for administration into human subjects according to regulatory guidelines for pharmaceutical compositions comprising the carrier.

Furthermore, a "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include any of the standard pharmaceutical carriers such as phosphate buffered saline solutions, water, emulsions such as oil/water emulsion, microemulsions and various types of wetting agents.

As set forth herein, the term "immunogenic fragment" means a fragment (e.g., a peptide) of a protein that can stimulate either humoral or cellular immune responses in the subject. An immunogenic fragment of this invention can comprise, consist essentially of and/or consist of one, two, three, four or more epitopes of a protein of this invention. An immunogenic fragment can be any fragment of contiguous amino acids of the CPAF protein and can be for example, 5, 10, 15, 20, 25, 30, 35, 40, 45, 50, 75, 100, 150, 200, 250, 300, 350, 400, 450, 500 or 550 amino acids in length. Identification of any such immunogenic fragments is routine in the art. Specific examples of an immunogenic fragment of a CPAF protein of this invention include, but are not limited to amino acids 1-200 (MGFWRTSIMKMNRIWLLLLTFSSAIHSPVRGESLVCKNALQDLSFLEHLLQVKYAPKTWKEQ YLGWDLVQSSVSAQQKLRTQENPSTSFCQQVLADFI GGLNDFHAGVTFFAIESAYLPYTVQKSSDGRFYFVDI MTFSSEIRVGDELLEVDGAPVQDVLATLYGSNHKGT AA EESAALRTLFSRMAS LGHKVPSGRTTL; SEQ ID NO:1), amino acids 136-609 (MTFSSEIRVGDELLEVD-GAPVQDVLATLYGSNHKGTAAEESAALRTLFSRMAS LGHKVPSGRTTLKIRRPFGTTREVRVKWRYVPEGVG DLATIAPSIRAPQLQKSMRSFFPKKDDAFHRSSSLFYS PMVPHFWAELRNHYATSGLKSGYNIGSTDGFLPVIGP VIWESEGLFRAYISSVTDGDGKSHKVGFLRIPTYSWQ DMEDFDPSGPPPWEEFAKIIQVFSSNTEALIIDQTNNP GGSVLYLYALLSMLTDRPLELPKHRMILTQDEVVDAL DWLTLLENVDTNVESRLALGDNMEGYTVDLQVAEY LKSFGRQVLNCWSKGDIELSTPIPLFGFEKIHPHPRVQ YSKPICVLNEQDFSCADFFPVVLKDNDRALIVGTRTA GAGGFVFNVQFPNRTGIKTCSLTGSLAVREHGAFIENI GVEPHIDLPFTANDIRYKGYSEYLDKVKKLVCQLINN D GTIILAEDGSF; SEQ ID NO:2), amino acids 242-609 (MRSFFPKKDDAFHRSSSLFYSPMVPHFWAELRNHY ATSGLKSGYNIGSTDGFLPVIGPVIWESEGLFRAYISS VTDGDGKSHKVGFLRIPTYSWQDMEDFDPSGPPPW EEFAKIIQVFSSNTEALIIDQTNNPGGSVLYLYALLSM LTDRPLELPKHRMILTQDEVVDALDWLTLLENVDTN VESRLALGDNMEGYTVDLQVAEYLKSFGRQVLNCW SkGDIELSTPIPLFGFEKIHPHPRVQYSKPICVLINEQD FSCADFFPVVLKDNDRALIVGTRTAGAGGFVFNVQF PNRTGIKTCSLTGSLAVREHGAFIENIGVEPHIDLPFTA NDIRYKGYSEYLDKVIKKLVCOLINNDGTIILAEDGS F; SEQ ID NO:3), amino acids 284-609 (GYNIGSTDG-FLPVIGPVIWESEGLFRAYISSVTDGDGKSHKVGFLRI PTYSWQDMEDFDPSGPP PWEEFAKIIQVFSSNTEALI-IDQTNNPGGSVLYLYALLSMLTDRPLELPKHRMILTQ DEVVDALDWLTLLENVDTNVESRLALGDNMEGYTV DLQVAEYLKSFGRQVLNCWSKGDIELSTPIPLFGFEK IHPHPRVQYSKPICVLINEQDFSCADFFPVVLKDNDR ALIVGTRTAGAGGFVFNVQFPNRTGIKTCSLTGSLAV REHGAFIENIGVEPHIDLPFTANDIRYKGYSEYLDKVI CKLVCQLNNDGTIILAE DGSF; SEQ ID NO:4) and amino acids 387-609 (MLTDRPLELPKHRMILTQDEVVDALD-WLTLLENVDTNVESRLALGDNMEGYTVDLQVAEYL KSFGRQVLNCWSKGDIELSTPIPLFGFEKIHPHPRVQY SK PICVLINEQDFSCADFFPVVLKDND RALIVGTRTA-GAGGFVFNVQFPNRTGIKTCSLTGSLAVREHGAFIENI GVEPHIDLPFTANDIRYKGYSEYLDKVKKLVCQLINN DGTIILAEDGSF; SEQ ID NO:5) (numbering is starting from amino acid 1 at the amino terminus through amino acid 609 at the carboxy teriminus of the CPAF protein: MGFWRT-SIMKMNRIWLLLLTFSSAIHSPVRGESLVCKNALQDL SFLEHLLQVKYAPKTWKEQYLGWDLVQSSVSAQQK LRTQENPSTSFCQQVLADFIGGLNDFHAGVTFFAIES AYLPYTVQKSSDGRFYFVDIMTFSSEIRVGDELLEVD GAPVQDVLATLYGSNHKGTAAEESAALRTLFSRMAS LGHKVPSGRTTLKIRRPFGTTREVRVKWRYVPEGVG DLATIAPSIRAPQLQKSMRSFFPKKDDAFHRSSSLFYS PMVPHFWAELRNHYATSGLKSGYNIGSTDGFLPVIGP VIWESEGLFRAYISSVTDGDGKSHKVGFLRIPTYSWQ DMEDFDPSGPPPWEEFAKIIQVFSSNTEALIIDQTNNP GGSVLYLYALLSMLTDRPLELPKHRMILTQDEVVDA LDWLTLLENVDTNVESRLALGDNMEGYTVDLQVAE YLKSFGRQVLNCWSKGDIELSTPIPLFGFEKIHPHPRV QYSKPICVLINEQDFSCADFFPVVLKDNDRALIVGTR TAGAGGFVFNVQFPNRTGIKTCSLTGSLAVREHGAFI ENIGVEPHIDLPFTANDIRYKGYSEYLDKVKKLVCQL I NNDGTIILAEDGSF (SEQ ID NO:6), the amino acid sequence of which is well known in the art. (Zhong et al. "Identification of a chlamydial protease-like activity factor responsible for the degradation of host transcription factors" *J Exp Med.* 193(8):935-42 (2001); Dong et al. "Intramolecular Dimerization Is Required for the *Chlamydia*-Secreted Protease CPAF To Degrade Host Transcriptional Factors" *Infection and Immunity,* 72:3869-3875 (2004); Dong et al. "Production of a Proteolytically Action Protease/Proteasome-Like Activity Factor, by Five Different *Chlamydia* Species," incorporated by reference in their entireties herein for their description and characterization of CPAF and GenBank® Accession numbers of various CPAF proteins (e.g., Accession No. AAC6859332, version GI:3329332)).

As noted herein, an immune response elicited or produced by carrying out the methods of this invention can be a protective immune response, a cellular immune response, a humoral immune response, a Th1 immune response, a Th2 immune response and any combination thereof.

To stimulate the humoral arm of the immune system, i.e., the production of antigen-specific antibodies, an immunogenic fragment can include at least about 5-10 contiguous amino acid residues of the full-length molecule, or at least about 15-25 contiguous amino acid residues of the full-length molecule, or at least about 20-50 or more contiguous amino acid residues of the full-length molecule, that define one or more epitopes, or any integer between five amino acids and the full-length sequence, provided that the fragment in question retains immunogenic activity, as measured by any art-known assay, such as, e.g., the ones described herein and/or those known in the art.

Regions of a given polypeptide that include an epitope can be identified using any number of epitope mapping techniques, well known in the art. (See, e.g., *Epitope Mapping Protocols in Methods in Molecular Biology,* Vol. 66, Glenn E. Morris, Ed., 1996, Humana Press, Totowa, N.J.). For example, linear epitopes can be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708, 871; Geysen et al. (1984) *Proc. Natl. Acad. Sci. USA* 81:3998-4002; Geysen et al. (1986) *Molec. Immunol.* 23:709-715, all incorporated herein by reference in their entireties.

Similarly, conformational epitopes are readily identified by determining spatial conformation of amino acids such as by, e.g., x-ray crystallography and 2-dimensional nuclear magnetic resonance. Antigenic regions of proteins can also be identified using standard antigenicity and hydropathy plots, such as those calculated using, e.g., the Omiga version 1.0 software program available from the Oxford Molecular Group. This computer program employs the Hopp/Woods method (Hopp et al., *Proc. Natl. Acad. Sci. USA* (1981) 78:3824-3828) for determining antigenicity profiles and the Kyte-Doolittle technique (Kyte et al., *J. Mol. Biol.* (1982) 157:105-132) for hydropathy plots.

Generally, T-cell epitopes that are involved in stimulating the cellular arm of a subject's immune system are short peptides of about 8-25 amino acids, and these are not typically predicted by the above-described methods for identifying humoral epitopes. A common way to identify T-cell epitopes is to use overlapping synthetic peptides and analyze pools of these peptides, or the individual ones, that are recognized by T cells from animals that are immune to the antigen of interest, using, for example, an enzyme-linked immunospot assay (ELISPOT). These overlapping peptides can also be used in other assays such as the stimulation of cytokine release or secretion, or evaluated by constructing major histocompatibility (MHC) tetramers containing the peptide. Such immunogenic fragments can also be identified based on their ability to stimulate lymphocyte proliferation in response to stimulation by various fragments from the antigen of interest.

The term "epitope" as used herein refers to at least about 3 to about 5, or about 5 to about 10 or about 5 to about 15, and not more than about 100, 500 or 1,000 amino acids (or any integer therebetween), which define a sequence that by itself or as part of a larger sequence, binds to an antibody generated in response to such sequence and/or stimulates a cellular immune response. There is no critical upper limit to the length of the fragment, which can comprise nearly the full-length of the protein sequence, or even a fusion protein comprising two or more epitopes from a single or multiple chlamydial proteins. An epitope for use in the present invention is not limited to a polypeptide having the exact sequence of the portion of the parent protein from which it is derived. Indeed, there are many known strains or isolates of *Chlamydia* and there are several variable domains that exhibit relatively high degrees of variability between isolates. Thus, the term "epitope" encompasses sequences identical to the native sequence, as well as modifications to the native sequence, such as deletions, additions and substitutions (generally, but not always, conservative in nature) that are readily produced and/or identified as epitopes according to methods standard in the art.

As used herein, the term "polypeptide" or "protein" is used to describe a chain of amino acids that correspond to those encoded by a nucleic acid. A polypeptide or protein of this invention can be a peptide, which usually describes a chain of amino acids of from two to about 30 amino acids. The term polypeptide as used herein also describes a chain of amino acids having more than 30 amino acids and can be a fragment or domain of a protein or a full length protein. Furthermore, as used herein, the term polypeptide can refer to a linear chain of amino acids or it can refer to a chain of amino acids that has been processed and folded into a functional protein. It is understood, however, that 30 is an arbitrary number with regard to distinguishing peptides and polypeptides and the terms can be used interchangeably for a chain of amino acids. The polypeptides of the present invention are obtained by isolation and purification of the polypeptides from cells where they are produced naturally, by enzymatic (e.g., proteolytic) cleavage, and/or recombinantly by expression of nucleic acid encoding the polypeptides or fragments of this invention. The polypeptides and/or fragments of this invention can also be obtained by chemical synthesis or other known protocols for producing polypeptides and fragments.

The amino acid sequences of this invention are presented in the amino to carboxy direction, from left to right. Nucleotide sequences are presented herein, in the 5' to 3' direction, from left to right. The nucleic acids of this invention can be either single or double stranded (i.e., including the complementary nucleic acid). A nucleic acid of this invention can be the complement (e.g., complementary to the full length or only to a portion) of a nucleic acid described herein.

A "biologically active fragment" includes a polypeptide of this invention that comprises a sufficient number of amino acids to have one or more of the biological activities of the polypeptides of this invention. Such biological activities can include, but are not limited to, in any combination, binding activity and/or immunogenic activity, as well as any other activity now known or later identified for the polypeptides and/or fragments of this invention.

A fragment of a polypeptide or protein of this invention can be produced by methods well known and routine in the art. Fragments of this invention can be produced, for example, by enzymatic or other cleavage of naturally occurring peptides or polypeptides or by synthetic protocols that are well known. Such fragments can be tested for one or more of the biological activities of this invention (e.g., immunogenicity) according to the methods described herein, which are routine methods for testing activities of polypeptides, and/or according to any art-known and routine methods for identifying such activities. Such production and testing to identify biologically active fragments and/or immunogenic fragments of the polypeptides described herein would be well within the scope of one of ordinary skill in the art and would be routine.

The term "isolated" as used herein means the protein or polypeptide or immunogenic fragment or nucleic acid or cell of this invention is sufficiently free of contaminants or cell components or other biological components with which polypeptides and/or nucleic acids and/or cells normally occur. "Isolated" does not mean that the preparation is technically pure (homogeneous), but it is sufficiently pure to provide the polypeptide or nucleic acid in a form in which it can be used therapeutically. Furthermore, an isolated cell is a cell that has been separated from other components with which it is normally associated in nature. For example, an isolated cell can be a cell in culture medium and/or a cell in a pharmaceutically acceptable carrier of this invention.

In additional embodiments, the present invention provides a method of providing passive immunity against chlamydial infection and disease to a subject, comprising administering to the subject an effective amount of an antibody of this invention to the subject. An antibody of this invention can be an antibody that specifically binds a CPAF protein or fragment or epitope thereof, as well as an antibody that specifically binds a different chlamydial protein or fragment or epitope thereof. The administration of antibodies to a subject in passive immunity protocols is well known and standard in the art.

As used herein, the term "antibody" includes intact immunoglobin molecules as well as fragments thereof, such as Fab, F(ab')2, and Fc, which are capable of binding the epitopic determinant of an antigen (i.e., antigenic determinant). Antibodies that bind the polypeptides of this invention are prepared using intact polypeptides and/or fragments containing small peptides of interest as the immunizing antigen. The polypeptide or fragment used to immunize an animal can be derived from enzymatic cleavage, recombinant expression, isolation from biological materials, synthesis, etc., and can be conjugated to a carrier protein, if desired. Commonly used carriers that are chemically coupled to peptides and proteins for the production of antibody include, but are not limited to, bovine serum albumin, thyroglobulin and keyhole limpet hemocyanin. The coupled peptide or protein is then used to immunize a host animal (e.g., a mouse, rat, goat, sheep, human or rabbit). The polypeptide or peptide antigens can also be administered with an adjuvant, as described herein and as otherwise known in the art.

The terms "antibody" and "antibodies" as used herein refer to all types of immunoglobulins, including IgG, IgM, IgA, IgD, and IgE. The antibody can be monoclonal or polyclonal and can be of any species of origin, including, for example, mouse, rat, rabbit, horse, goat, sheep or human, and/or can be a chimeric or humanized antibody. See, e.g., Walker et al., *Molec. Immunol.* 26:403-11 (1989). The antibodies can be recombinant monoclonal antibodies produced according to the methods disclosed in U.S. Pat. No. 4,474,893 or U.S. Pat. No. 4,816,567. The antibodies can also be chemically constructed according to the method disclosed in U.S. Pat. No. 4,676,980. The antibody can further be a single chain antibody or bispecific antibody.

Techniques for the production of chimeric antibodies or humanized antibodies by splicing mouse antibody genes to human antibody genes to obtain a molecule with appropriate antigen specificity and biological activity can be used (Morrison et al. 1984. *Proc. Natl. Acad. Sci.* 81:6851-6855; Neuberger et al. 1984. *Nature* 312:604-608; Takeda et al. 1985. *Nature* 314:452-454). Alternatively, techniques described for the production of single chain antibodies can be adapted, using methods known in the art, to produce single chain antibodies specific for the polypeptides and/or fragments and/or epitopes of this invention. Antibodies with related specificity, but of distinct idiotypic composition, can be generated by chain shuffling from random combinatorial immunoglobin libraries (Burton 1991. *Proc. Natl. Acad. Sci.* 88:11120-3).

Antibody fragments included within the scope of the present invention include, for example, Fab, F(ab')2, and Fc fragments, and the corresponding fragments obtained from antibodies other than IgG. Such fragments can be produced by known techniques. For example, F(ab')2 fragments can be produced by pepsin digestion of the antibody molecule, and Fab fragments can be generated by reducing the disulfide bridges of the F(ab')2 fragments. Alternatively, Fab expression libraries can be constructed to allow rapid and easy identification of monoclonal Fab fragments with the desired specificity (Huse et al., (1989) *Science* 254:1275-1281).

Monoclonal antibodies can be produced in a hybridoma cell line according to the technique of Kohler and Milstein (*Nature* 265:495-97 (1975)). For example, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in bacterial cell such as *E. coli* by recombinant techniques known to those skilled in the art. See, e.g., W. Huse, (1989) *Science* 246:1275-81.

Antibodies can also be obtained by phage display techniques known in the art or by immunizing a heterologous host with a cell containing an epitope of interest.

The methods of this invention can be practiced to treat and/or prevent infection and/or disease caused by any chlamydial species that can infect a subject of this invention, including, for example *Chlamydia trachomatis, Chlamydia pneumoniae, Chlamydia muridarum, Chlamydia psittaci, Chlamydophila abortus* and/or *Chlamydia caviae*.

The terms "prevent," "preventing," and "prevention" and like terms are used herein to include imparting any level of prevention or protection which is of some benefit to a subject, such that there is a reduction in the incidence and/or the severity of the disease in a treated subject, regardless of whether the protection or reduction in incidence and/or severity is partial or complete.

By "prime," "primed" or "priming" (and grammatical variations thereof) as used herein, it is meant to initiate an active immune response that is less than protective until a second dose (booster) is given at a later time.

"Boost" or "booster" means a second immunization, after an initial (or "priming") immunization that enhances the immune response of the subject. Therefore, in some embodiments, the invention provides a composition that produces an anamnestic response against a *Chlamydia* infection, in a sensitized subject, comprising an anamnestic response-inducing amount of a *Chlamydia* protein immunizing component. As used herein, the term "anamnestic response" means a secondary (booster) immune response in a sensitized subject. By "sensitized subject" is meant a subject that has previously been in contact with a chlamydial antigen or antigens, either by natural exposure or by vaccination (primary immunization) with *Chlamydia* protein immunizing components.

The terms "reduce," "reduced," "reducing," and "reduction" (and grammatical variations thereof), as used herein, describe a decrease in a chlamydial infection- or disease-related parameter or symptom that is of some therapeutic value or benefit to the subject.

As used herein, the terms "elicit" or "induce" or "produce" (or grammatical variations thereof) in the context of an immune response against *Chlamydia* are intended to encompass the activation and/or stimulation of cells and other components of the immune system in a subject to ameliorate the effects of chlamydial infection in the subject. The immune response of this invention can be a protective immune response, for example, as desired in vaccination methods to treat and/or prevent infection. Protection is not required if there is some other purpose for inducing the immune response, for example, for research purposes or to produce antibody for passive immunizations or as a reagent (e.g., to detect, isolate and/or identify *Chlamydia* species).

Also as used herein, the terms "treat," "treating" or "treatment" refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, prevention or delay of the onset of the disease, disorder, or illness, and/or change in clinical parameters of the condition, disorder, disease or illness, etc., as would be well known in the art.

As used herein "effective response" or "responding effectively" means a positive or beneficial response to a particular treatment in contrast to a "lack of an effective response" which can be an ineffectual, negative or detrimental response as well as the lack of a positive or beneficial response. An effective response or lack of effective response (i.e., ineffective response) is detected by evaluation, according to known protocols, of various immune functions (e.g., cell-mediated immunity, humoral immune response, etc.) and pharmacological and biological functions as would be known in the art.

"Effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation. (See, for example, Remington, *The Science And Practice of Pharmacy* (20th ed. 2000)).

The terms "immunogenic amount" or "effective immunizing dose," as used herein, unless otherwise indicated, mean a dose of a composition of this invention sufficient to induce an immune response (which can be a protective response) in the treated subject that is greater than the inherent immunity of non-immunized subjects. An immunogenic amount or effective amount or effective immunizing dose in any particular context can be routinely determined using methods known in the art.

In some embodiments, an effective immunizing dose or immunogenic amount or effective amount can comprise one or more (e.g., two or three or four or more) doses of the immunogenic composition of this invention at any time interval (e.g., hourly, daily, weekly, monthly, yearly, etc.) so as to achieve and/or maintain the desired level of protection and/or other therapeutic benefit.

The terms "vaccine," "vaccination" and "immunization" are well-understood in the art, and are used interchangeably herein. For example, the terms vaccine, vaccination or immunization can be understood to be a process or composition that increases a subject's immune reaction to an immunogen (e.g., by providing an active immune response), and therefore its ability to resist, overcome and/or recover from infection (i.e., a protective immune response).

The terms "protective immunity" or "protective immune response," as used herein, are intended to mean that the subject mounts an active immune response to the immunogenic composition and/or that the subject has been provided with passive immunity, such that upon subsequent exposure or a challenge, the animal is able to resist and/or overcome infection and/or disease. Thus, a protective immune response will decrease the incidence of morbidity and/or mortality from subsequent exposure to the chlamydial pathogens of this invention.

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formulation*, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

In some embodiments, "cross-species immunity," e.g., immunity with respect to multiple species of *Chlamydia* (e.g., *Chlamydia muridarum, Chlamydia trachomatis*, etc.) (e.g., cross-species protective immunity) can be accomplished with the methods of this invention as described herein. Thus, the present invention provides a method of eliciting a cross-species immune response in a subject (e.g., to treat and/or prevent chlamydial infection and/or disease) by administering to the subject an effective amount of the immunogenic chlamydial compositions of this invention, such as CPAF and/or an immunogenic fragment or epitope thereof, alone or in combination with one or more than one different chlamydial protein or immunogenic fragment or epitope thereof, and/or an adjuvant of this invention, thereby eliciting a cross-species immune response to *Chlamydia* species in the subject.

In certain embodiments, employing the methods of this invention provides a reduction in the incidence of hydrosalpinx, oviduct dilatation, and/or cellular infiltration associated with chlamydial infection. Thus, the present invention further provides methods of treating and/or preventing hydrosalpinx, oviduct dilatation, and/or cellular infiltration associated with chlamydial infection in a subject, comprising administering to the subject an immunogenic composition of this invention, with our without an adjuvant.

In yet further embodiments, the immune response of this invention can include a Th1 immune response. "Th1" refers to a helper T cell response which involves the production of interferon-gamma (IFN-γ), leading to cell-mediated immunity. In other embodiments, the immune response can include a Th2 immune response. "Th2" refers to a helper T cell response which involves the release of interleukin 4 (IL-4), leading to humoral immunity. See, e.g., U.S. Patent Application Publication No. 2006/0034871 to Grandi et al., incorporated by reference herein in its entirety for its teachings of Th1 and Th2 responses.

In some embodiments, the immune response of this invention includes a gamma interferon (IFN-γ)-dependent protective immune response. Thus the present invention additionally provides a method of eliciting a gamma interferon-dependent protective immune response against *Chlamydia* in a subject, comprising administering to the subject an effective amount of an immunogenic composition of this invention, with or without an adjuvant.

A "subject" of this invention includes any animal susceptible to infection by a Chlamydial species. Such a subject can be a mammal (e.g., a laboratory animal such as a rat, mouse, guinea pig, rabbit, primates, etc.), a farm or commercial animal (e.g., a cow, horse, goat, donkey, sheep, etc.), a domestic animal (e.g., cat, dog, ferret, etc.), an avian species and in particular embodiments, is a human. A "subject in need thereof" is a subject known to be, or suspected of being, infected with, or at risk of being infected with, *Chlamydia*. A subject of this invention can also include a subject not previously known or suspected to be infected by *Chlamydia* or in need of treatment for *Chlamydia* infection. For example, a subject of this invention can be administered the compositions of this invention even if it is not known or suspected that the subject is infected with *Chlamydia* (e.g., prophylactically). A subject of this invention is also a subject known or believed to be at risk of infection by *Chlamydia*.

In certain embodiments, the fragments and/or polypeptides of this invention can be fused with a "carrier" protein or peptide to produce a fusion protein. For example, the carrier protein or peptide can be fused to a polypeptide and/or fragment of this invention to increase the stability thereof (e.g., decrease the turnover rate) in the cell and/or subject. Exemplary carrier proteins include, but are not limited to, glutathione-S-transferase or maltose-binding protein. The carrier protein or peptide can alternatively be a reporter protein. For example, the fusion protein can comprise a polypeptide and/or fragment of this invention and a reporter protein or peptide (e.g., green fluorescent protein (GFP), β-glucuronidase, β-galactosidase, luciferase, and the like) for easy detection. As a further alternative, the fusion protein attached to the polypeptides and/or fragments and a carrier protein or peptide can be targeted to a subcellular compartment of interest, i.e., to affect the co-localization of the polypeptide and/or fragment. Any suitable carrier protein as is well known in the art can be used to produce a fusion protein of this invention.

The present invention further includes isolated polypeptides, peptides, proteins and/or fragments that are substantially equivalent to those described for this invention. As used herein, "substantially equivalent" can refer both to nucleic acid and amino acid sequences, for example a mutant sequence, that varies from a reference sequence by one or more substitutions (e.g., substitution with conservative amino acids as are well known in the art), deletions and/or additions, the net effect of which does not result in an undesirable adverse functional dissimilarity between reference and subject sequences. In some embodiments, this invention can include substantially equivalent sequences that have an adverse functional dissimilarity. For purposes of the present invention, sequences having equivalent biological activity and equivalent expression characteristics are considered substantially equivalent.

The invention further provides homologues, as well as methods of obtaining homologues, of the polypeptides and/or fragments of this invention from other strains of *Chlamydia* and/or other organisms included in this invention. As used herein, an amino acid sequence or protein is defined as a homologue of a polypeptide or fragment of the present invention if it shares significant homology to one of the polypeptides and/or fragments of the present invention. Significant homology means at least 75%, 80%, 85%, 90%, 95%, 98% and/or 100% homology with another amino acid sequence. Specifically, by using the nucleic acids that encode the chlamydial proteins and fragments of this invention (as are known in the art and incorporated by reference herein), as a probe or primer, and techniques such as PCR amplification and colony/plaque hybridization, one skilled in the art can identify homologues of the polypeptides and/or fragments of this invention in *Chlamydia* and/or other organisms on the basis of information available in the art. As one non-limiting example, a listing of *Chlamydia pneumoniae* proteins and the *Chlamydia trachomatis* homologues of these proteins can be found in U.S. Pat. No. 6,822,071, the entire contents of which are incorporated by reference herein for these teachings.

It is further contemplated that the present invention provides a kit comprising the compositions of this invention. It would be well understood by one of ordinary skill in the art that the kit of this invention can comprise one or more containers and/or receptacles to hold the reagents (e.g., antibodies, antigens, nucleic acids) of the kit, along with appropriate buffers and/or diluents and/or other solutions and directions for using the kit, as would be well known in the art. Such kits can further comprise adjuvants and/or other immunostimulatory or immunomodulating agents, as are well known in the art.

The compositions and kits of the present invention can also include other medicinal agents, pharmaceutical agents, carriers, diluents, immunostimulatory cytokines, etc. Actual methods of preparing such dosage forms are known, or will be apparent, to those skilled in this art.

It is contemplated that the above-described compositions of this invention can be administered to a subject or to a cell of a subject to impart a therapeutic benefit, such as eliciting an immune response. Thus, as noted above, the present invention further provides a method of eliciting or producing an immune response in a subject, comprising administering to the subject or to a cell of the subject an effective amount of a polypeptide and/or immunogenic fragment and/or epitope of this invention and/or a nucleic acid comprising a nucleotide sequence encoding a polypeptide and/or immunogenic fragment and/or epitope of this invention, with or without an adjuvant of this invention. The cell of the subject can be in vivo or ex vivo and can be, but is not limited to a CD8+ T lymphocyte (e.g., a cytotoxic T lymphocyte), an MHC I-expressing antigen presenting cell, such as a dendritic cell, a macrophage and/or a monocyte. The cell can also be an antigen presenting cell or other class I MHC-expressing cell which can be contacted with the nucleic acids and/or vectors of this invention under conditions whereby the nucleic acid or vector is introduced into the cell by standard methods for uptake of nucleic acid and vectors. The nucleic acid encoding the polypeptide and/or fragment of this invention is then expressed and the polypeptide and/or fragment product is processed within the antigen presenting cell or other MHC I-expressing cell and presented on the cell surface as an MHC I/antigen complex. The antigen presenting cell or other class I MHC-expressing cell is then contacted with an immune cell of the subject which binds the class I MHC/antigen complex and elicits an immune response which treats or prevents *Chlamydia* infection in the subject.

Detection of an immune response in the subject and/or in the cells of the subject can be carried out according to methods standard in the art for detecting a humoral and/or cellular immune response.

As noted above, the compositions of this invention can be administered to a cell of a subject or to a subject either in vivo or ex vivo. For administration to a cell of the subject in vivo, as well as for administration to the subject, the compositions of this invention can be administered orally, intranasally, intravaginally, intraocularly, parenterally (e.g., intravenously), by intramuscular injection, by intraperitoneal injection, subcutaneous injection, transdermally, extracorporeally, topically or the like. Also, the compositions of this invention can be pulsed onto dendritic cells, which are isolated or grown from a subject's cells, according to methods well known in the art, or onto bulk peripheral blood mononuclear cells (PBMC) or various cell subfractions thereof from a subject.

The exact amount(s) of the composition(s) of this invention that will be required will vary from subject to subject, depending on the species, age, weight and general condition of the subject, the particular composition used, its mode of administration and the like. Thus, it is not possible to specify an exact amount for every composition of this invention. However, effective amount can be determined by one of ordinary skill in the art using only routine experimentation given the teachings herein and that are well known in the art.

As an example, to a subject diagnosed with *Chlamydia* infection or known to be at risk of being infected with *Chlamydia* or in whom it is desirable to induce an immune response to *Chlamydia*, between about 50-1000 nM, or between about 100-500 nM of a polypeptide and/or immunogenic fragment of this invention can be administered, e.g., subcutaneously, and can be in an adjuvant, at one to three hour/day/week intervals until an evaluation of the subject's clinical parameters indicate that the subject is not infected by *Chlamydia* and/or the subject demonstrates the desired immunological response. Alternatively, a polypeptide and/or fragment of this invention can be pulsed onto dendritic cells at a concentration of between about 10-100 µM and the dendritic cells can be administered to the subject intravenously at the same time intervals. The treatment can be continued or resumed if the subject's clinical parameters indicate that *Chlamydia* infection is present and/or the desired immunological response is diminished or no longer present and can be maintained until the infection is no longer detected by these parameters and/or until the desired immunological response is achieved or re-established.

Parenteral administration of the peptides, polypeptides, nucleic acids and/or vectors of the present invention, if used, is generally characterized by injection. Injectables can be prepared in conventional forms, either as liquid solutions or suspensions, solid forms suitable for solution of suspension in liquid prior to injection, or as emulsions. As used herein, "parenteral administration" includes intradermal, intranasal, subcutaneous, intramuscular, intraperitoneal, intravenous and intratracheal routes, as well as a slow release or sustained release system such that a constant dosage is maintained. See, e.g., U.S. Pat. No. 3,610,795, which is incorporated by reference herein in its entirety.

The efficacy of treating or preventing *Chlamydia* infection by the methods of the present invention can be determined by detecting a clinical improvement as indicated by a change in the subject's symptoms and/or clinical parameters, as would be well known to one of skill in the art.

The pharmaceutical compositions of this invention include those suitable for oral, intranasal, rectal, topical, inhalation (e.g., via an aerosol) buccal (e.g., sub-lingual), vaginal (e.g., vaginal ring), rectal, intraurethral, parenteral (e.g., subcutaneous, intramuscular, intradermal, intraarticular, intrapleural, intraperitoneal, intracerebral, intraarterial, or intravenous), topical (i.e., both skin and mucosal surfaces, including airway surfaces) and transdermal administration. The compositions herein can also be administered via a skin scarification method or transdermally via a patch, liquid or gel. The compositions can be delivered subdermally in the form of a biodegradable material that releases the compositions over time. The most suitable route in any given case will depend, as is well known in the art, on such factors as the species, age, gender and overall condition of the subject, the nature and severity of the condition being treated and/or on the nature of the particular composition (i.e., dosage, formulation) that is being administered.

Pharmaceutical compositions suitable for oral administration can be presented in discrete units, such as capsules, cachets, lozenges, or tables, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a composition of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical composition according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sub-lingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions of this invention suitable for parenteral administration can comprise sterile aqueous and non-aqueous injection solutions of the composition of this invention, which preparations are preferably isotonic with the blood of the intended recipient. These preparations can contain anti-oxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

In certain embodiments the compositions of this invention can be administered to the mucous membranes of a subject (e.g., via intranasal administration). The formulations may be conveniently prepared in unit dosage form and may be prepared by any of the methods well known in the art. For example, formulations may be administered to the mucosa as a liquid, spray and/or mist.

The compositions can be presented in unit\dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 1 µg to about 10 grams of the composition of this invention. When the composition is substantially water-insoluble, a sufficient amount of emulsifying agent, which is physiologically and pharmaceutically acceptable, can be included in sufficient quantity to emulsify the composition in an aqueous carrier. One such useful emulsifying agent is phosphatidyl choline.

Pharmaceutical compositions suitable for rectal administration are preferably presented as unit dose suppositories. These can be prepared by admixing the composition with one or more conventional solid carriers, such as for example, cocoa butter and then shaping the resulting mixture.

Pharmaceutical compositions of this invention suitable for topical application to the skin preferably take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, *Pharmaceutical Research* 3:318 (1986)) and typically take the form of an optionally buffered aqueous solution of the composition of this invention. Suitable formulations can comprise citrate or bis\tris buffer (pH 6) or ethanol/water and can contain from 0.1 to 0.2M active ingredient.

The frequency of administration of a composition of this invention can be as frequent as necessary to impart the desired therapeutic effect. For example, the composition can be administered one, two, three, four or more times per day, one, two, three, four or more times a week, one, two, three, four or more times a month, one, two, three or four times a year or as necessary to control the condition. In some embodiments, one, two, three or four doses over the lifetime of a subject can be adequate to achieve the desired therapeutic effect. In some embodiments, alternate day dosing can be employed (e.g., every other day). The amount and frequency of administration of the composition of this invention will vary depending on the particular condition being treated or to be prevented and the desired therapeutic effect.

In additional embodiments of this invention, the compositions of this invention can comprise a protein and/or immunogenic fragment and/or epitope thereof of a different pathogenic organism in any combination [e.g., a pathogenic organism that is sexually transmitted, including but not limited to: *Trichomonas* (e.g., *Trichomonas vaginalis*); a pathogenic yeast or fungus (e.g., *Candida albicans*), *Neisseria* (e.g., *N. gonorrhea*), *Treponema pallidum*, and pathogenic viruses (e.g., herpes simplex virus (HSV), human immunodeficiency virus (HIV), human papilloma virus (HPV)].

The following examples are included to demonstrate various embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention.

EXAMPLES

Example 1

Chlamydial Protease-like Activity Factor Induces Protective Immunity Against Genital Chlamydial Infection in Humanized HLA-DR4 Transgenic Mice Bacteria. *Chlamydia trachomatis* mouse pneumonitis (MoPn; recently designated as the separate species *C. muridarum*) was grown on confluent HeLa cell monolayers. The cells were lysed using a sonicator (Fisher, Pittsburgh, Pa.) and the elementary bodies (EBs) were purified on Renograffin gradients as described (9, 14). Aliquots of bacteria were stored at −70° C. in Sucrose-Phosphate-Glutamine (SPG) buffer. *Chlamydia* genus-specific murine monoclonal antibody was used to confirm the identity of the purified bacterium (9).

Mice. HLA-DRA-IEα/HLA-DRB1*0401-IEβ tg mice were generated and backcrossed to MHC class II-deficient mice (MHC II$^{\Delta/\Delta}$ mice) to eliminate any effect of endogenous MHC class II proteins, as described previously (5). The MHC II$^{\Delta/\Delta}$ mice were generated by complete deletion of the H2-Aa, H2-Eb1 and H2-Eb2 genes and bred to C57BL/6 mice, as described previously (6). The HLA-DR4 tg mice, MHC II$^{\Delta/\Delta}$ mice (Jackson Laboratories, Bar Harbor, Me.), and C57BL/6 mice (Charles River Laboratories, Wilmington, Mass.) were housed and bred at the University of Texas at San Antonio Animal Care Facility and provided food and water ad libitum. Animal care and experimental procedures were performed in compliance with the Institutional Animal Care and Use Committee (IACUC) guidelines. 4-6 wk old female mice were used for all experiments.

Intravaginal infection. Mice were anesthetized intranasally (i.n.) using 3% isofluorane in a rodent anesthesia system (Harvard Apparatus, Holliston, Mass.) and immediately inoculated intravaginally (i.vag.) with 1,500 inclusion forming units (IFU) of *C. muridarum* in 5 µl of sterile SPG buffer (9). Vaginal vaults of challenged mice were swabbed at three day intervals, and swabs collected into Eppendorf tubes containing 4 mm glass beads (Kimble, Vineland, N.J.) and 500 μl of sterile SPG buffer. The tubes were vortexed for 1 min and swab material was plated and incubated for 28 h with HeLa cells grown on coverslips in 24-well plates. The infected HeLa cells were fixed with 2% paraformaldehyde and permeabilized with 2% saponin. Cells were washed using PBS and incubated with Modified Dulbecco's Eagle's Medium containing 10% fetal bovine serum for 1 hr to block non-specific binding. Thereafter, cells were washed and incubated with polyclonal rabbit anti-*Chlamydia* antibody for 1 hr and then incubated for an additional 2 hr with goat anti-rabbit Ig conjugated to FITC (Sigma, St. Louis, Mo.) plus Hoescht nuclear stain. The treated coverslip cultures were then washed and mounted onto superfrost microscope slides (Fisher) using Fluorsave reagent (Calbiochem, La Jolla, Calif.). Slides were visualized using a Zeiss Axioskop 2 Plus research microscope (Zeiss, Thornwood, N.Y.). The bacterial shedding was calculated and expressed as the number of inclusion forming units per animal.

Determination of cytokine responses using ELISA. Spleens from HLA-DR4 tg mice were removed on day 14 after i.vag. *C. muridarum* challenge or i.n. CPAF (15 μg)+ interleukin 12 (IL-12) (0.5 μg) immunization, respectively, and single cell suspensions made. Splenocytes ($10^6$ cells/well) were plated on 96-well culture plates and stimulated with 0.5 μg/ml of recombinant CPAF (rCPAF) or hen egg lysozyme (HEL), and incubated for 72 hr. The culture supernatants were then assayed for interferon gamma (IFN-γ and interleukin 4 (IL-4) using BD OptELISA kits (BD pharmingen, NJ) according to the manufacturer's instructions. Results were calculated and expressed as pg/ml of IFN-γ or IL-4.

Detection of antibody levels by ELISA. 96-well microtiter plates were coated overnight with UV-inactivated *C. muridarum* ($10^5$ IFU/well) or 5 μg/well of CPAF in sodium bicarbonate buffer (pH 9.5), washed with PBS containing 0.3% Brij-35 (Sigma), and blocked for 1 hr at room temperature with PBS containing 2% bovine serum albumin (BSA, EM Science Gibbstown, N.J.). Serial dilutions of sera were added to wells and incubated at room temperature for 2 hr. The plates were then washed and incubated for an additional 1 hr with goat anti-mouse total Ig conjugated to alkaline phosphatase (Southern Biotechnology Associates, Birmingham, Ala.). After incubation for 1 hr, the plates were washed and p-nitrophenyl phosphate substrate was added for color development. Absorbance at 405 nm was measured using an ELISA microplate reader (Biotek Instruments, Winooski, Vt.). No binding of immune sera was observed when the plates were coated with the unrelated antigen hen egg lysozyme (HEL).

Cloning and expressing CPAF. The open reading frames coding for CPAF from *C. trachomatis* L2 genome were cloned into pBAD vectors and expressed as fusion proteins with a 6-His tag at the N-terminus. The amino acid sequences of CPAF from serovar L2 and *C. muridarum* share significant identity (82%). Expression of the fusion protein designated CPAF (CPAF with 6-His tag) was induced with L-arabinose (Sigma) and the fusion proteins were extracted by lysing the bacteria via sonication in a Triton X-100 lysis buffer (1% Triton X-100, 1 mM phenylmethylsulfonyl fluoride, 75 U of aprotinin/ml, 20 μM leupeptin, and 1.6 μM pepstatin). After high-speed centrifugation to remove debris, the fusion protein-containing supernatants were purified further with Ni-NTA agarose beads (QIAGEN, Valencia, Calif.) for 6-Histag proteins.

Intranasal (i.n.) immunization procedures. Intranasal immunization was performed as described previously (1). Briefly, mice were anesthetized i.n. with 3% isofluorane using a rodent anesthesia system (Harvard Apparatus, Holliston, Mass.). Mice were immunized i.n. on day 0 with 15 μg rCPAF dissolved in 25 μl sterile phosphate buffered saline (PBS). This was accompanied on days −1, 0, and +1 with ±0.5 μg of recombinant murine IL-12 (Wyeth, Cambridge, Mass.) in PBS containing 1% normal mouse serum (NMS). Mice were boosted i.n. with 15 μg rCPAF±IL-12 (0.5 μg) on days 14 and 28. Some mice received only PBS-NMS (no rCPAF vaccine). As previously described, no toxicity was observed with the IL-12 treatment regimen (4). The dose of rCPAF that provided optimal protection against genital *C. trachomatis* challenge in BALB/c mice was used.

Statistical analyses. SIGMA STAT software (Chicago, Ill.) was used to perform all the tests of significance. The Kruskall-Wallis test was used to determine differences in vaginal chlamydial shedding between experimental groups. The infection resolution time between groups was compared using the Kaplan-Meier test. Differences were considered statistically significant if p values were <0.05. All data shown are representative of at least two independent experiments and have been expressed as mean±standard deviation (S.D).

HLA-DR4 tg mice resolve primary genital *C. muridarum* infection similar to conventional C57Bl/6 mice. The resolution of primary genital *C. muridarum* infection following challenge with 1,500 IFU was analyzed by comparing vaginal chlamydial shedding at timed intervals in conventional C57BL/6, MHC $II^{\Delta/\Delta}$ and HLA-DR4 tg mice. Challenged HLA-DR4 tg mice displayed resolution kinetics comparable to conventional C57BL/6 animals. The chlamydial shedding progressively reduced, such that 100% of HLA-DR4 tg and C57BL/6 animals resolved the infection by day 27 after challenge. In contrast, challenged MHC $II^{\Delta/\Delta}$ animals shed significantly greater numbers of *Chlamydia* (≧0.5 log) as compared to similarly treated HLA-DR4 tg and conventional C57BL/6 animals at day 9 after challenge and at all subsequent time-points examined. All of the challenged MHC $II^{\Delta/\Delta}$ animals were still shedding considerable numbers of *Chlamydia* (114±12) even at day 30 after challenge. These results indicate that (a) MHC class II molecules are important in chlamydial clearance, (b) chlamydial antigenic epitopes presented on human HLA-DR4 molecules elicit protective immunity, and (c) epitopes presented on HLA-DR4 molecules induce comparable protective immunity to those presented on murine MHC class II molecules, suggesting that HLA-DR4 tg mice are a useful model to study immunity against genital chlamydial infections.

Anti-chlamydial immune response in HLA-DR4 tg mice is comparable to conventional C57BL/6 mice. The cellular and humoral immune responses were analyzed in the HLA-DR4 tg, C57BL/6, and MHC $II^{\Delta/\Delta}$ animals after i.vag. challenge with 1,500 IFU of *C. muridarum*. On day 14 after challenge, splenocytes from challenged animals were stimulated in vitro with UV-inactivated *C. muridarum* and the production of IFN-γ and IL-4 was measured. Splenocytes from *C. muridarum* infected HLA-DR4 tg animals exhibited a high level (3702±242 pg/ml) of antigen-specific IFN-γ production, comparable to similarly infected conventional C57BL/6 mice (3482±307 pg/ml). In contrast, splenocytes from MHC $II^{\Delta/\Delta}$ animals displayed only minimal amounts of IFN-γ production (68±20 pg/ml). Mock-infected (PBS) animals, and cells stimulated with media alone or an unrelated antigen (HEL) did not exhibit antigen-specific IFN-γ production, suggesting the specificity of the immune response. There was no detectable IL-4 production in splenocytes from any animal group.

The serum humoral response was measured on days 14, 21, and 28 after i.vag. *C. muridarum* challenge. HLA-DR4 tg mice displayed progressively increasing titers of anti-*C. muridarum* serum antibodies that were comparable to conventional C57BL/6 mice on days 14 (1177±182 and 1213±323, respectively), 21 (1394±130 and 1514±438, respectively), and 28 (1620±142 and 1838±217, respectively) after challenge. In contrast, MHC $II^{\Delta/\Delta}$ animals displayed severely reduced serum antibody titers at each time-point examined. Mock-infected (PBS) animals did not produce detectable titers of anti-*C. muridarum* antibodies and none of the animal groups displayed serum antibodies against the unrelated antigen HEL. Collectively, these results indicate that the anti-chlamydial immune response in HLA-DR4 tg animals was comparable to that of conventional C57BL/6 mice. Furthermore, the markedly reduced cellular and humoral responses against *Chlamydia* in MHC $II^{\Delta/\Delta}$ animals suggest indirectly that HLA-DR4 molecules present chlamydial antigens to T-cells, leading to generation of the measured anti-chlamydial responses.

Immune responses to CPAF following primary genital chlamydial challenge. The question of whether human MHC II molecules in HLA-DR4 tg mice present CPAF epitopes during an active genital chlamydial infection was examined by comparing anti-CPAF immune responses in HLA-DR4 tg versus C57BL/6 and MHC $II^{\Delta/\Delta}$ animals following genital *C. muridarum* challenge. On day 14 after challenge, splenocytes from mice were stimulated in vitro with CPAF, media alone or the unrelated antigen HEL. Splenocytes from *C. muridarum* infected HLA-DR4 tg animals exhibited a high level (1106±252 pg/ml) of antigen-specific IFN-γ production comparable to similarly infected conventional C57BL/6 mice (1242±324 pg/ml). In contrast, splenocytes from MHC $II^{\Delta/\Delta}$ animals displayed only minimal amounts of IFN-γ production (250±46 pg/ml). Cells treated with HEL or media alone did not exhibit detectable IFN-γ production. There was no detectable IL-4 production in any culture supernatant. These results indicate the induction via the HLA-DR4 molecules of a Th1 type anti-CPAF cellular immune response during genital *C. muridarum* infection.

The humoral response against CPAF also was analyzed at various timed intervals in i.vag. *C. muridarum* challenged HLA-DR4 tg versus C57BL/6 and MHC $II^{\Delta/\Delta}$ animals. HLA-DR4 tg mice displayed progressively increasing titers of anti-*C. muridarum* serum antibodies that were comparable to conventional C57BL/6 mice on days 14 (1181±228 and 1201±233, respectively), 21 (1325±140 and 1416±57, respectively), and 28 (1352±211 and 1478±245, respectively) after challenge. In contrast, MHC $II^{\Delta/\Delta}$ animals displayed severely reduced serum antibody titers at each time-point examined. At the same time-points, there was no detectable CPAF-specific antibody response in mock-infected (PBS) animals and no antibody binding in plates coated with the unrelated antigen HEL. These results demonstrate the induction of a CPAF-specific humoral response via HLA-DR4 molecules after i.vag. *C. muridarum* challenge.

Intranasal vaccination with CPAF induces a robust immune response. Intranasal (i.n.) vaccination with CPAF+IL-12 induces a robust Th1 type cellular and humoral immune response and leads to protective immunity against genital *C. muridarum* infection in conventional BALB/c mice. The induction of immune responses at timed intervals after i.n. CPAF+IL-12 immunization was examined in the present study using HLA-DR4 tg mice compared to similarly treated C57BL/6 and MHC $II^{\Delta/\Delta}$ mice. Animals were immunized with CPAF+IL-12 on day 0 and boosted on days 14 and 28. On day 14 after primary immunization, splenocytes were stimulated in vitro with CPAF, media alone, or HEL for 72 hr and the production of IFN-γ and IL-4 was analyzed by ELISA. High levels of IFN-γ production were induced in splenocytes from CPAF+IL-12 immunized HLA-DR4 tg mice (3800±77 pg/ml) and C57BL/6 mice (3463±363 pg/ml), but not MHC $II^{\Delta/\Delta}$ animals (25±22 pg/ml) upon in vitro stimulation with CPAF. Splenocytes from mock-immunized (PBS) animals stimulated with CPAF, or cells from any group stimulated with the unrelated antigen, HEL, did not display detectable IFN-γ production. There was minimal IL-4 production in each of the cell cultures. Furthermore, splenocytes from mice receiving IL-12 alone did not exhibit CPAF-specific IFN-γ production.

The induction of a CPAF-specific humoral response after immunization was examined ten days after the last booster immunization. HLA-DR4 tg mice exhibited comparable anti-CPAF antibody titers to similarly treated conventional C57BL/6 animals with high titers of total Ig (5670±465 and 5560±665, respectively), IgG2a (5642±253 and 3572±916, respectively), IgG2b (3433±873 and 5400±242, respectively), and IgG1 (3299±1009 and 3178±880, respectively). In contrast, vaccinated MHC $II^{\Delta/\Delta}$ animals displayed severely reduced serum antibody titers (anti-CPA-F total Ig—358±23; IgG2a—254±100; IgG2b—160±75; and IgG1—150±30, respectively). Furthermore, the relative titers of anti-CPAF IgG2a were greater than IgG1 in immunized HLA-DR4 tg animals. Mock-immunized (PBS) animals displayed minimal CPAF-specific antibody responses. No binding was detected in ELISA plates coated with an unrelated antigen, HEL. These results demonstrate that intranasally administered CPAF is processed and presented on the HLA-DR4 molecules to induce Th1 type cellular and strong humoral responses in the HLA-DR4 tg animals.

Intranasal CPAF vaccination enhances resolution of genital chlamydial infection. The resolution kinetics of a genital chlamydial infection were analyzed in CPAF+IL-12 immunized HLA-DR4 tg, C57BL/6 and MHC $II^{\Delta/\Delta}$ mice. Animals were immunized i.n. with CPAF+IL-12 or PBS on days 0, 14, and 28, rested for one month, and challenged i.vag. with *C. muridarum* (1,500 IFU). Vaccinated HLA-DR4 tg and C57BL/6 mice displayed significantly reduced (<35%) vaginal chlamydial shedding as early as day 3 after challenge and at subsequent time-points as compared to corresponding mock-immunized (PBS) animals. Chlamydial numbers rapidly reduced in the vaccinated HLA-DR4 tg mice and complete resolution of infection was attained in 67% of animals by day 15 and 100% of animals by day 18 after challenge. Vaccinated C57BL/6 animals exhibited comparable kinetics with 100% of animals completely resolving the infection by day 15 after challenge. Mock-immunized (PBS) HLA-DR4 tg and C57BL/6 animals completely resolved the infection between day 27-30 after challenge. In contrast, none of the MHC $II^{\Delta/\Delta}$ animals immunized with CPAF+IL-12 or PBS had resolved the infection at day 30 after challenge and all of the animals were still shedding a considerable number of organisms (198±82 and 114±29 IFU, respectively) at that point. Treatment with IL-12 alone did not appreciably affect bacterial clearance, and was comparable to mock (PBS) immunization. Collectively, these results demonstrate that (a) MHC class II molecules are important in generation of protective immunity against genital chlamydial infection and (b) epitopes of CPAF presented on human HLA-DR4 molecules generate robust anti-chlamydial protective immunity leading to accelerated resolution of genital chlamydial infection.

Example 2

The Protective Efficacy of Chlamydial Protease-like Activity Factor Vaccination is Dependent Upon CD4+ T Cells Mice. Female 4-8 week old C57BL/6 mice were purchased from Simonsen Laboratories (Gilroy, Calif.) and maintained at the University of Texas at San Antonio Animal Facility. Mice were given food and water ad libitum and all animal procedures were performed in compliance with the Institutional Animal Care and Use Committee (IACUC) guidelines.

Bacteria. *Chlamydia trachomatis* mouse pneumonitis (MoPn; recently designated as the separate species *C. muridarum*) was grown on confluent HeLa cell monolayers. The cells were lysed using a sonicator (Fisher, Pittsburgh, Pa.) and the elementary bodies (EBs) were purified on Renograffin gradients as described previously (14). Aliquots of bacteria were stored at −70° C. in Sucrose-Phosphate-Glutamine (SPG) buffer. *Chlamydia* genus-specific murine monoclonal antibody was used to confirm the identity of the purified bacterium (9).

CPAF. The open reading frames coding for CPAF from *C. trachomatis* L2 genome were cloned into pBAD vectors and expressed as fusion proteins with a 6-His tag at the N-terminus. The amino acid sequences of CPAF share significant identity (82%) between serovar L2 and *C. muridarum* (18). Expression of the fusion protein designated CPAF (CPAF with 6-His tag) was induced with L-arabinose (Sigma, St. Louis, Mo.) and the fusion proteins were extracted by lysing the bacteria via sonication in a Triton X-100 lysis buffer (1% Triton X-100, 1 mM phenylmethylsulfonyl fluoride, 75 U of aprotinin/ml, 20 µM leupeptin, and 1.6 µM pepstatin). The fusion protein-containing supernatants were purified further with Ni-NTA agarose beads (QIAGEN, Valencia, Calif.) for 6-Histag proteins. Aliquots of purified proteins were stored at −70° C. until use. Before vaccination, the biological activity of recombinant CPAF was confirmed by the ability to degrade the transcription factor, RFX-5 (30).

Intranasal immunization. Vaccination was performed as described previously (1). Briefly, mice were anesthetized i.n. with 3% isofluorane using a rodent anesthesia system (Harvard Apparatus, Holliston, Mass.). Then, the C57BL/6 mice were immunized i.n. on day 0 with 15 µg CPAF dissolved in 25 µl sterile phosphate buffered saline (PBS). This was accompanied on days −1, 0, and +1 with 0.5 µg of recombinant murine IL-12 (Wyeth, Cambridge, Mass.) in PBS containing 1% normal mouse serum (NMS). Mice were boosted i.n. with 15 µg CPAF+0.5 µg IL-12 on days 14 and 28. Some mice received only PBS-NMS (no CPAF vaccine). Animals vaccinated with the chosen dose of CPAF and IL-12 exhibited optimal protective immunity against genital chlamydial challenge when compared to treatment with soluble CPAF or IL-12 alone. Therefore, this study was restricted to analyses of protective immunity in CPAF+IL-12 vaccinated animals. As previously described, no toxicity was observed with the IL-12 treatment regimen (4).

Antigen-specific CD4+ T cell responses. Animals were treated i.n. with CPAF+IL-12 or PBS and spleens were removed after 14 days. Splenocytes were layered over a ficoll density gradient to collect mononuclear cells. CD4+ T cell populations were isolated by negative selection using magnetic particles (Stem Cell Technologies) and the purity of CD4+ T cell populations was determined to be at least >95% by flow cytometry using an APC labeled anti-CD4 monoclonal antibody (BD Biosciences). A separate pool of naïve splenocytes also was prepared from mock (PBS) vaccinated animals and treated with mitomycin C (25 µg/$10^7$ cells) for 20 min and used as a source of antigen presenting cells (APCs). Purified CD4+ T cells ($5 \times 10^5$ cells/well) were cultured with naïve antigen presenting cells ($5 \times 10^5$ cells/well) and stimulated for 72 hr in vitro with CPAF or an unrelated antigen, hen egg lysozyme (HEL). Supernatants from the culture wells were analyzed for IFN-γ and IL-4 production using BD OptELISA kits (BD pharmingen, NJ) according to the manufacturer's instructions.

Detection of antibody levels by ELISA. 96-well microtiter plates were coated overnight with 5 µg/ml of CPAF or UV-inactivated *C. muridarum* ($10^5$ IFU/well) in sodium bicarbonate buffer (pH 9.5), washed with PBS containing 0.05% Tween-20 (Sigma) and blocked for 1 hr at room temperature with PBS containing 2% bovine serum albumin (BSA, EM Science Gibbstown, N.J.). Serial dilutions of serum were added to wells and incubated at room temperature for 2 hr. The plates were then washed and incubated for an additional 1 hr with goat anti-mouse total Ig, IgG2a, IgG2b, or IgG1 conjugated to alkaline phosphatase (Southern Biotechnology Associates, Birmingham, Ala.). After incubation for 1 hr, the plates were washed and p-nitrophenyl phosphate substrate was added for color development. Absorbance at 405 nm was measured using an ELISA microplate reader (Biotek Instruments, Winooski, Vt.). Reciprocal serum dilutions corresponding to 50% maximal binding were used to obtain titers. No binding of immune sera was observed when the plates were coated with the unrelated antigen HEL.

In vivo CD4+ T cell depletion. The GK1.5 hybridoma cell line, which produces anti-CD4 neutralizing antibody (8), was purchased from ATCC and grown according to the manufacturer's instructions. The anti-CD4 monoclonal antibody was purified using ammonium sulfate precipitation. A rat immunoglobulin (rat Ig, Sigma Aldrich) was used as an isotype control. On days −6, −5, and −4 and on the day of challenge and every third day afterwards, animals were injected intraperitoneally (i.p.) with 0.5 mg of purified anti-CD4 monoclonal antibody (GK1.5). The last injection of monoclonal antibody was given on day 21 after challenge. Control mice received rat Ig or PBS injection over the same schedule. CD4+ T cell depletion was monitored by flow cytometry using an APC labeled anti-CD4 monoclonal antibody (BD Biosciences). Five days prior to challenge, mice were treated with 2.5 mg of Depo-Provera (Upjohn, Kalamazoo, Mich.), to synchronize ovulation and animals (now 12-16 wk old) were subsequently infected i.vag. with 1,500 IFU of *C. muridarum*.

Adoptive transfer of CD4+ T cells. Experimental mice (4-8 wk old) were immunized intranasally (i.n.) with CPAF+IL-12, while the control groups were challenged i.vag. with 1,500 IFU of *C. muridarum* or mock-treated with PBS. The mice were rested for 30 days after the last boost, sacrificed, and the spleens removed. Single cell suspensions were made and layered over a ficoll density gradient (Cedarlane Laboratories, Canada) to obtain mononuclear cells. CD4+ T cell populations were enriched by negative selection using magnetic particles (Stem Cell Technologies). The purity of the CD4+ T cell population was determined to be at least >95% by flow cytometry using an APC labeled anti-CD4 monoclonal antibody (BD Biosciences). Two hours before transfer, female C57BL/6 mice (4-8 week old) were challenged intravaginally with 1,500 IFU of *C. muridarum*. Approximately $10^7$ CD4+ T cells were transferred i.p. into naïve mice. Bacterial shedding was monitored at three-day intervals as detailed below.

Intravaginal challenge. Mice were anesthetized i.n. using 3% isofluorane in a rodent anesthesia system (Harvard Apparatus, Holliston, Mass.) and immediately inoculated i.vag. with 1,500 inclusion forming units (IFU) of *C. muridarum* in 5 µl of sterile SPG buffer. Vaginal vaults of challenged mice were swabbed at three day intervals, and the swabs transferred into Eppendorf tubes containing 4 mm glass beads (Kimble, Vineland, N.J.) and 500 µl of sterile SPG buffer. The tubes were vortexed for 1 min and swab material was plated and incubated for 28 hr with HeLa cells grown on coverslips in 24-well plates. The infected HeLa cells were fixed with 2% paraformaldehyde and permeabilized with 2% saponin. Cells were washed using PBS and incubated with Modified Dulbecco's Eagle's Medium containing 10% fetal bovine serum for 1 hr to block non-specific binding. Thereafter, cells were washed and incubated with polyclonal rabbit anti-*Chlamydia* antibody for 1 hr and then incubated for an additional 2 hr with goat anti-rabbit Ig conjugated to FITC (Sigma, St. Louis, Mo.) plus Hoescht nuclear stain. The treated coverslip cultures were then washed and mounted onto superfrost microscope slides (Fisher) using Fluorsave reagent (Calbiochem, La Jolla, Calif.). Slides were visualized using a Zeiss Axioskop 2 Plus research microscope (Zeiss, Thornwood, N.Y.). The bacterial shedding was calculated and expressed as the number of inclusion forming units per animal.

Histology and staining. Genital tracts were removed from mice at various time-points after challenge, fixed in 10% neutral formalin, and embedded into paraffin blocks. Serial horizontal sections (5 µm) were prepared and every tenth section (~8-10 sections per tissue) was stained using hematoxylin and eosin (H&E). Stained sections were visualized using a Zeiss Axioskop 2 Plus research microscope and images were acquired using an Axiocam digital camera (Zeiss, Thornwood, N.Y.). Representative sections stained with H&E were scored in blinded fashion by a trained pathologist using a scoring scheme modified from Rank et al. (23). Dilatation of oviducts was scored as follows: 0—no significant dilatation, 1—mild dilatation of single cross-section of oviduct, 2—1-3 dilated cross-sections of oviduct, 3—>3 dilated cross-sections of oviduct, 4—confluent pronounced dilatation of oviduct. Results are expressed as mean±SEM of scores from all animals in a group (n=6).

Statistical analyses. SIGMA STAT software (Chicago, Ill.) was used to perform all the tests of significance. The Student t test was used to determine differences in cytokine and antibody production, and the Kruskall-Wallis test for differences in vaginal chlamydial shedding between experimental groups. The infection resolution time between groups was compared using the Kaplan-Meier test. Differences were considered statistically significant if p values were <0.05. All data shown are representative of at least two independent experiments.

Intranasal CPAF+IL-12 immunization induces Th1 type immune response. Splenocytes were removed at day 14 after i.n. immunization and purified CD4$^+$ T cells (5×10$^5$ cells/well) were cultured with mitomycin treated splenocytes as antigen presenting cells (5×10$^5$ cells/well) and stimulated with CPAF. Purified CD4$^+$ T cells from CPAF+IL-12 vaccinated animals exhibited elevated levels of IFN-γ production, in a dose-dependent fashion (1.2 ng/ml and 1.5 ng/ml of IFN-γ, respectively), upon stimulation with 0.5 µg or 1 µg of CPAF, as compared to those from mock-immunized (PBS) animals. Cells cultured with media or the unrelated antigen HEL displayed minimal IFN-γ production. Additionally, there was no induction of cytokine production when purified cells were stimulated with UV-inactivated *C. muridarum* (10$^5$ IFU/well) or with another 6-Histidine tagged protein (BA 1) cloned from *Francisella tularensis*, indicating the specificity of measured responses to CPAF. CD4$^+$ T cells from all groups of animals responded to the non-specific T cell mitogen concanavalin A (conA) stimulation by producing high levels of IFN-γ, indicating that the minimal cytokine production from mock-immunized (PBS) CD4$^+$ T cells was not due to an inability of these cells to be activated. There was no detectable IL-4 production in any of the cell cultures.

The antibody response to CPAF immunization was measured at timed intervals during the immunization regimen. On day 40, ten days after the last booster immunization, animals vaccinated with CPAF+IL-12 displayed elevated titers of CPAF-specific total Ab and IgG2a, IgG2b and IgG1 antibodies as compared to other treatment groups. Additionally, the titers of serum anti-CPAF total Ab (5670±665) and IgG2b (5642±253) were relatively greater than those of IgG2a (3573±916) and IgG1 (3299±1009). There was minimal CPAF-specific antibody response in mock-immunized (PBS) animals and no antibody binding observed in wells coated with HEL or in wells coated with UV-inactivated *C. muridarum* or BA1. Serum antibody levels on days 14 and 28 exhibited comparable trends, but lower titers of each antibody isotype than at day 40. Collectively, these results demonstrate the induction of antigen-specific Th1 type cellular response, and robust humoral response after CPAF+IL-12 vaccination.

The protective effects of CPAF vaccination is abrogated by depletion of CD4$^+$ T cells in vaccinated animals. The contribution of CPAF-specific CD4$^+$ T cells in conferring protective immunity against primary genital *C. muridarum* infection was examined by depletion of vaccinated mice using an anti-CD4 neutralizing antibody. Intraperitoneal injection of the neutralizing anti-CD4 antibody markedly depleted the splenic CD4$^+$ T cells (<1%) as shown by flow cytometry, and in contrast to injection with control rat immunoglobulin (29%). The CPAF+IL-12 vaccinated animals depleted of CD4$^+$ T cells shed significantly greater numbers of *Chlamydia* as early as day 9 and through day 24 after challenge, in marked contrast to vaccinated animals injected with control rat immunoglobulin. Specifically, challenged CPAF+IL-12 animals treated with control rat Ig shed significantly fewer chlamydiae on day 9 (~10-fold reduction), day 12 (~50 fold reduction), and day 15 (~10,000 fold reduction), as compared to challenged CPAF+IL-12 animals treated with anti-CD4 antibody. Whereas all of the CPAF+IL-12 vaccinated animals treated with control rat immunoglobulin completely resolved the infection by day 15 after challenge, 100% of similarly vaccinated mice treated with anti-CD4 antibody were still shedding *Chlamydia* as late as day 24 after challenge. Vaccinated CD4$^+$ T cell depleted mice resolved the infection only upon cessation of the neutralizing anti-CD4 treatment. Mock-immunized animals shed significantly fewer *Chlamydia* on days 18-24 as compared to CPAF+IL-12 vaccinated anti-CD4 antibody treated mice and completely resolved the infection by day 27 after challenge. These results suggest that CPAF+IL-12 mediated chlamydial clearance is dependent on CD4$^+$ T cells.

Anti-chlamydial immunity can be adoptively transferred by CPAF-specific CD4$^+$ T cells. Based upon the outcome of the depletion studies, additional studies were conducted to determine whether adoptive transfer of CPAF-specific CD4$^+$ T cells would confer protection against genital chlamydial challenge. Naïve recipient C57BL/6 mice were injected i.p. with enriched CD4$^+$ T cells obtained from mice vaccinated with CPAF+IL-12 and concurrently challenged i.vag. with 1,500 IFU of *C. muridarum*. As controls, some groups of mice received enriched CD4$^+$ T cells purified from mice infected i.n. with *C. muridarum* (200 IFU) or treated with PBS (mock) and concurrently challenged with *Chlamydia. C. muridarum* challenged mice that received CPAF-specific CD4$^+$ T cells exhibited significantly lower bacterial shedding at the indicated time-points compared to recipients of T cells from mock-immunized (PBS) animals, with 50% of the CPAF-specific CD4+ T cell recipient animals completely resolving the infection by day 15 and 100% by day 18. In comparison, mock-immunized (PBS) CD4+ T cell recipients exhibited greater shedding through 24 days and resolved the infection only by day 27-30 after challenge. Importantly, C. muridarum challenged mice that received CPAF-specific CD4+ T cells exhibited resolution kinetics comparable to mice that received C. muridarum-specific CD4+ T cells, with both groups of animals completely resolving the infection by day 18 post-challenge. These results demonstrate that (a) anti-chlamydial protective immunity can be adoptively transferred by CPAF-specific CD4+ T cells and (b) CPAF-specific CD4+ T cells induce protective anti-chlamydial immunity comparable to C. muridarum-specific CD4+ T cells.

CPAF-specific CD4+ T cells are capable of inducing protective immunity against oviduct pathology The development of oviduct dilatation is a characteristic complication of genital chlamydial infection in mice (7). Intranasal CPAF+IL-12 vaccination protects against development of oviduct dilatation and reduces inflammatory cellular infiltration into the upper genital tract following genital C. muridarum challenge in an IFN-γ dependent fashion. In the current study, the contribution of CPAF-specific CD4+ T cells in protection against oviduct pathology was examined by analyzing the development of histopathological changes after C. muridarum challenge in animals that were vaccinated and depleted of CD4+ T cells or in mice that received CPAF-specific CD4+ T cells. As shown in FIG. 5, CPAF+IL-12 vaccinated mice treated with control rat Ig exhibited significantly lower oviduct dilatation scores when compared to mock-immunized (PBS) animals at day 80 after challenge. In marked contrast, CPAF+IL-12 vaccinated mice treated with anti-CD4 antibody exhibited greater oviduct pathology than mock-immunized (PBS) animals. Additionally, C. muridarum challenged mice adoptively transferred with CPAF-specific CD4+ T cells exhibited significantly lower oviduct pathology than mock-immunized (PBS) animals. The degree of protection against the development of oviduct dilatation in CPAF+IL-12 (rat Ig group) and in animals receiving CPAF-specific CD4+ T cells was comparable to animals receiving C. muridarum primed T cells. Moreover, CPAF+IL-12 vaccinated mice (rat Ig group) and those adoptively transferred with CPAF-specific or C. muridarum-specific CD4+ T cells exhibited significantly lower infiltration of polymorphonuclear leukocytes, mononuclear cells, and plasma cells on day 80 after challenge, when compared to mock-immunized animals. These results together suggest that CD4+ T cells play an important role in CPAF+IL-12 vaccination-induced protection against oviduct pathology.

Example 3

Intranasal Vaccination with a Secreted Chlamydial Protein Enhances Resolution of Genital Chlamydia muridarum Infection, Protects against Oviduct Pathology and is Highly Dependent Upon Endogenous IFN-γ Production Recombinant CPAF (rCPAF) and IL-12. rCPAF from the C. trachomatis L2 genome was cloned and expressed in a bacterial system as described previously (3). Briefly, rCPAF constructs cloned from the C. trachomatis L2 genome with a 6-Histidine tag (His) were cloned into pBAD vectors and expressed in Escherichia coli with isopropyl-β-D-thiogalactopyranoside (IPTG) as an inducer. The fusion protein was purified using Ni-NTA agarose beads (Amersham Biosciences Corp.). The purified rCPAF was identified by Western blot analysis using a monoclonal anti-CPAF antibody (49). CPAF activity was determined by the ability to degrade the transcription factor RFX-5 in a concentration-dependent fashion, using a cell-free degradation assay, as described previously (13). The purified rCPAF was used as a source of protein for all experiments. A recombinant protein BA1 (HisBA-1) was cloned from the Francisella tularensis genome and similarly expressed with a 6-Histidine tag and used as specificity control for some experiments. Murine recombinant IL-12 was obtained from Wyeth (Cambridge, Mass.).

Bacteria. Chlamydia muridarum was grown on confluent HeLa cell monolayers. Cells were lysed using a sonicator (Fisher, Pittsburgh, Pa.) and elementary bodies (EBs) were purified on Renograffin gradients as described previously (14). Aliquots of bacteria were stored at −70° C. in sucrose-phosphate-glutamine buffer. For some experiments, C. muridarum stocks were inactivated using UV light as described previously (11).

Mice. Four week-old, female BALB/c mice were obtained from Charles River Laboratory (Bar Harbor, Me.). Age-matched female BALB/c IFN-γ$^{-/-}$ mice were obtained from Jackson Laboratory (Bar Harbor, Me.). Mice were housed and bred at the University of Texas at San Antonio and provided food and water ad libitum. Animal care and experimental procedures were performed in compliance with the Institutional Animal Care and Use Committee (IACUC) guidelines.

Intranasal (i.n.) immunization procedures. Intranasal immunization was performed as described previously (1). Briefly, mice were anesthetized i.n. with 3% isofluorane using a rodent anesthesia system (Harvard Apparatus, Holliston, Mass.). Mice were immunized i.n. on day 0 with 15 µg rCPAF dissolved in 25 µl sterile phosphate buffered saline (PBS). This was accompanied on days −1, 0, and +1 with ±0.5 µg of recombinant murine IL-12 (Wyeth, Cambridge, Mass.) administered intranasally in PBS containing 1% normal mouse serum (NMS). Mice were boosted i.n. with 15 µg rCPAF±IL-12 on days 14 and 28. Some mice received only IL-12 in PBS-NMS or only PBS-NMS (no rCPAF vaccine). The dose of rCPAF that provided optimal protection (15 µg/mouse) was determined from previous experiments in which titrating doses of rCPAF (1 µg-20 µg/mouse) were evaluated for protective efficacy against genital C. muridarum challenge.

Antigen-specific splenocyte recall responses. Spleens were removed 14 days after primary vaccination and single cell suspensions prepared. Collected cells [10$^6$/well (spleen)] were incubated for 72 hr with 1 µg rCPAF per well or with an equal concentration of an unrelated antigen, i.e., hen egg lysozyme (HEL), HisBA-1, 10$^5$ IFU of UV-inactivated C. muridarum (C. mur) or PBS alone in 96-well culture plates. Supernatants were assayed for levels of IFN-γ and IL-4 using BDOptEIA™ kits (BD Pharmingen, San Diego, Calif.) according to manufacturer's instructions. Absorbance at 630 nm was measured using a µQuant ELISA microplate reader (Biotek Instruments, Winooski, Vt.).

Detection of antibody and isotype levels by ELISA. Ten days following final immunization, animals were bled for serum, or bronchoalveolar lavage (BAL) or vaginal lavage fluids were obtained and analyzed by ELISA as described previously (9). Microtiter plates (96-well) were coated overnight with 5 µg rCPAF in sodium bicarbonate buffer (pH 9.5). Serial dilutions of serum or undiluted bronchoalveolar lavage (BAL) fluids or vaginal lavage fluids were added to wells followed by either goat anti-mouse total Ig, IgG1, IgG2a, IgG2b, IgM, or IgA conjugated to alkaline phosphatase (Southern Biotechnology Associates, Birmingham, Ala.). After washing, p-nitrophenyl phosphate substrate (Sigma, St. Louis, Mo.) was added for color development and absorbance (O.D.) at 405 nm was monitored using a µQuant ELISA microplate reader (Biotek Instruments). Reciprocal serum dilutions corresponding to 50% maximal binding were used to obtain titers. Because of the low amounts of antibody (Ab) in BAL and vaginal fluids and the large dilution involved in the lavage procedure, these samples were tested undiluted. No binding of immune serum was detected in plates coated with an HEL, HisBA-1, or to UV-inactivated *C. muridarum*.

Vaginal *C. muridarum* challenge and determination of bacterial shedding. One month following the final vaccination, animals (n=6-10) were anesthetized using inhalational isofluorane (3%) and challenged intravaginally (i.vag.) with $5 \times 10^4$ inclusion forming units (IFU) of *C. muridarum* in 5 µl of SPG buffer. Two doses of depo-provera (Pharmacia Upjohn, Kalamazoo, Mich.) were injected subcutaneously on days −10 and −3 before challenge. To monitor bacterial shedding, vaginal swabs were obtained on the indicated days after vaginal challenge, followed by plating of the swab material on HeLa cell monolayers grown on culture coverslips. Chlamydial inclusions were detected using a murine anti-*Chlamydia* genus specific murine monoclonal primary antibody and goat anti-mouse IgG secondary antibody conjugated to Cy3 plus Hoescht nuclear stain. The average number of inclusions in 5 random microscopic fields was calculated for each animal for earlier time-points (until day 12 after challenge) and entire coverslips for later time-points (days 15-30 after challenge), and results were expressed as the average number of inclusions per animal group.

Histology and staining. Genital tracts were removed from mice at various indicated time-points after challenge, fixed in 10% neutral formalin, and embedded into paraffin blocks. Serial horizontal sections (5 µm) were prepared and stained using hematoxylin and eosin (H&E). Stained sections were visualized using a Zeiss Axioskop 2 Plus research microscope and images were acquired using an Axiocam digital camera (Zeiss, Thornwood, N.Y.).

Histological scoring. Sections stained with H&E were scored in blinded fashion by a trained pathologist using a scoring scheme modified from Rank et al. (23). Dilatation of oviducts was scored as follows: 0—no significant dilatation, 1—mild dilatation of single cross-section of oviduct, 2—1-3 dilated cross-sections of oviduct, 3—>3 dilated cross-sections of oviduct, or 4—confluent pronounced dilatation of oviduct. Cellular parameters (polymorphonuclear cells (PMNs), mononuclear, and plasma cells) were individually scored as follows: 0—no significant presence of infiltration, 1—presence of infiltration at a single focus, 2—presence at 2-4 foci, 3—presence at more than 4 foci, or 4—confluent infiltration. Results are expressed as mean±SEM of scores from all animals in a group (n=6-8).

Statistical analyses. For comparison of two groups, the student's t test (for normally distributed values) or the Mann-Whitney Rank Sum test (for values not distributed normally) was used to compare values of continuous variables. For experiments with four groups of animals, analysis of variance (ANOVA) followed by multiple comparison of means (Kruskall-Wallis test) was used. To analyze differences in the time required for clearance, the Kaplan-Meier test was used. Differences between groups were considered statistically significant if P values were <0.05. All data shown are representative of 2-5 independent experiments and each experiment shown was analyzed independently.

Intranasal immunization with rCPAF plus IL-12 induces robust cellular Th1 type immune responses. Cell mediated immunity is a crucial component of protective immunity against *Chlamydia* (50, 51). Therefore, studies were conducted to determine whether vaccination with rCPAF+IL-12 induces antigen-specific cell mediated responses. Mice were vaccinated and rCPAF-induced cytokine recall responses were analyzed in splenocytes at fourteen days post-vaccination. Antigen-specific IFN-γ production was significantly greater ($p<0.05$) in spleen cells from rCPAF+IL-12 immunized animals as compared to mice immunized with rCPAF alone. Conversely, IL-4 production was reduced ($p<0.05$) in rCPAF+IL-12 immunized mice as compared to rCPAF immunized animals. Splenocytes from mock-vaccinated (PBS) or IL-12 treated mice did not exhibit detectable cytokine induction. The specificity of the response against rCPAF was evidenced by minimal induction of cytokine production from spleen cells stimulated with either HEL, UV-inactivated *C. muridarum* (*C. mur*) that do not express CPAF in this metabolically inactive EB stage, or to an unrelated 6-Histidine tag protein cloned from *Francisella tularensis* (HisBA-1). These results indicate that i.n. rCPAF+IL-12 vaccination induces a strong Th1 biased antigen-specific cellular immune response.

Intranasal rCPAF+IL-12 immunization induces systemic and mucosal antibody responses. Humoral response to rCPAF immunization was examined on day 40 after initial i.n. immunization. Intranasal vaccination induced a robust serum antibody response that included rCPAF-specific total Ab, IgG2a, IgG2b, and IgG1 isotypes. Specifically, rCPAF+IL-12 immunized mice exhibited significantly enhanced ($p<0.05$) titers of anti-rCPAF total Ab and IgG2a, but not IgG2b and IgG1 antibodies as compared to animals vaccinated with rCPAF alone. Since mucosal antibodies are important in protection against pathogens (15, 16, 26, 27, 28), induction of antibody response at local inductive sites was measured in bronchoalveolar lavage (BAL) and vaginal fluids collected from immunized animals. rCPAF+IL-12 immunized animals exhibited significantly higher levels ($p<0.05$) of anti-rCPAF total Ab, IgG2a, and IgA in BAL fluids when compared to animals immunized with rCPAF alone. Similarly, rCPAF-specific total Ab, IgG2a, IgG1, and IgA titers in vaginal fluid of rCPAF+IL-12 vaccinated animals were significantly higher ($p<0.05$) than mice receiving rCPAF alone. Mock-vaccinated or IL-12 treated animals did not exhibit antigen-specific antibody responses in serum or in respiratory and vaginal fluids. Serum antibody levels on day 14 and 28 exhibited comparable trends with increased titers of specific antibodies in rCPAF+IL-12 treated animals; although the titers were lower than at 40 days after first immunization. Furthermore, no serum antibody responses were found against HEL, HisBA-1, or to UV-inactivated *C. muridarum* in any treatment group, indicating the specificity of immune responses generated by rCPAF+IL-12 vaccination. The fact that rCPAF+IL-12 vaccinated animals displayed negligible cell-mediated and humoral cross-reactivity with HisBA-1 indicates that the 6-Histag does not contribute to the immunogenicity of rCPAF. These results indicate that rCPAF+IL-12 induces a robust, systemic and mucosal anti-rCPAF antibody response including production of antigen-specific IgA at mucosal sites.

rCPAF+IL-12 immunization enhances the resolution of a genital *C. muridarum* infection. The protective efficacy of i.n. rCPAF vaccination was examined by monitoring shedding of chlamydiae after intravaginal challenge with $5 \times 10^4$ IFUs *C.*

*muridarum*. There was significant reduction (≧0.5 log) in the number of chlamydiae recovered from animals vaccinated with rCPAF+IL-12 as early as 8 days post-challenge when compared to mock-immunized (PBS) or EL-12 treated animals. Moreover, 30% of rCPAF+IL-12 vaccinated animals had successfully resolved the infection by day 12, 80% animals by day 15 and 100% animals by day 18 (Table 6). In contrast, mock-vaccinated (PBS) or animals receiving rCPAF or IL-12 alone were still heavily infected at day 15. Forty percent of mice vaccinated with rCPAF alone had resolved the infection by day 18 and 70% by day 24 after challenge (Table 6). In comparison, 30% of mice treated with PBS or IL-12 alone were still actively shedding chlamydiae 30 days after bacterial challenge. These results demonstrate the efficacy of rCPAF+IL-12 vaccination in enhancing resolution of genital chlamydial infection.

rCPAF plus IL-12 induces protection against *C. muridarum*-induced upper genital tract pathology. To determine the effect of rCPAF+IL-12 vaccination on development of inflammatory disease, gross and histopathological changes in the oviduct and mesosalpingeal tissues were monitored following *C. muridarum* challenge. Since rCPAF+IL-12 immunization demonstrated the greatest efficacy in resolution of genital chlamydial infection (Table 6), *C. muridarum* induced pathology was compared between rCPAF+IL-12 and mock-vaccinated (PBS) animals. Genital *C. muridarum* infections in BALB/c mice have been shown to characteristically induce development of hydrosalpinx as a gross pathological complication (7). Oviducts in mock-vaccinated (PBS) animals exhibited the presence of hydrosalpinx as compared to the apparent normal appearance in rCPAF+IL-12 immunized mice upon gross examination on day 80 post-challenge. Specifically, at 50 and 80 days post-challenge, hydrosalpinx was not apparent in any of the rCPAF+IL-12 immunized mice, whereas most (88% and 75%, respectively) of the mock-immunized mice exhibited this gross pathological finding (Table 7). The observed pathology was bilateral (62.5%) in most, but unilateral in some mock-immunized (PBS) animals at day 50 (25% unilateral) and day 80 (12.5% unilateral) after challenge, respectively. Hydrosalpinx was not apparent in the mice until day 30 after challenge. Mice treated with IL-12 alone and challenged with *C. muridarum* displayed similar frequency of hydrosalpinx development to challenged PBS treated (mock) animals.

Detailed histopathological comparisons were performed on rCPAF+IL-12 and mock-immunized animals (PBS) after genital *C. muridarum* challenge. While most of the rCPAF+IL-12 immunized mice exhibited apparently normal oviducts, mock-immunized (PBS) animals developed characteristic dilated oviducts by day 80 after challenge. In addition, there were normal appearing fimbriae in rCPAF+IL-12 immunized animals while mock-vaccinated animals exhibited fimbrial flattening. Tissue sections from individual mice in both groups were blind-scored by a trained pathologist in order to evaluate the degree of oviduct dilatation. Oviduct dilatation on days 50 and 80 post-challenge in rCPAF+IL-12 vaccinated mice was significantly reduced (0.2±0.2 and 0.3±0.18, respectively) as compared to mock-immunized (PBS) animals (2.3±0.75 and 3.2±0.4, respectively). Very little oviduct dilatation was detected in either group until day 30 after challenge. In addition, Masson trichrome staining of tissues demonstrated significantly reduced fibrosis in rCPAF+IL-12 immunized animals as compared to mock-immunized animals on day 80 post-challenge.

The infiltration of inflammatory cells into the oviduct and mesosalpingeal tissues also was scored and evaluated in rCPAF+IL-12 and PBS immunized mice at various days after challenge. These analyses revealed comparable numbers of polymorphonuclear leukocytes (PMNs) in tissues from both groups of animals up to day 18 after challenge. However, on days 30 and 50 after challenge, PMN infiltrates in rCPAF+IL-12 vaccinated mice were significantly reduced (0.12±0.1 and 0.1±0.1) when compared to mock-immunized (PBS) animals (1.56±0.17 and 1.6±0.18, respectively). No significant PMN infiltration was detected in either group at day 80 post-challenge. The numbers of infiltrating mononuclear and plasma cells in rCPAF+IL-12 immunized animals also were significantly reduced when compared to mock-immunized animals from day 18 to 80 post-challenge. Mice treated with IL-12 alone displayed similar degrees of oviduct dilatation and cellular infiltration to challenged PBS treated animals whereas non-challenged PBS treated animals did not exhibit pathological changes at any of the indicated observation periods. These results demonstrate that rCPAF+IL-12 vaccination reduces the pathology and duration of inflammatory cellular infiltration into the oviduct and mesosalpingeal tissues after genital *C. muridarum* challenge.

IFN-$\gamma$ is important in mediating rCPAF+IL-12 induced genital protection. The role of IFN-$\gamma$ in rCPAF+IL-12 mediated protection was examined using mice deficient in endogenous IFN-$\gamma$ production (IFN-$\gamma^{-/-}$ mice). Vaccinated IFN-$\gamma^{+/+}$ mice began resolving the infection as early as 9 days post-challenge (Table 8). By 9 and 12 days post-challenge, some vaccinated IFN-$\gamma^{+/+}$ (33.3% and 50%, respectively), but not IFN-$\gamma^{-/-}$ mice (0%) had completely resolved the infection. On day 18 post-challenge, 100% of rCPAF+IL-12 vaccinated IFN-$\gamma^{+/+}$ mice had resolved the infection, in contrast to only 16.7% of vaccinated IFN-$\gamma^{-/-}$ animals. As late as 50 days post-challenge, 50% of vaccinated IFN-$\gamma^{-/-}$ mice were still shedding low numbers of bacteria. In contrast, mock-immunized IFN-$\gamma^{+/+}$ mice completely resolved the infection by day 50 post-challenge, while a majority of similarly treated IFN-$\gamma^{-/-}$ mice (66.7%) were still shedding chlamydiae 50 days post-challenge. Moreover, the induction of rCPAF-specific antibody responses in vaccinated IFN-$\gamma^{-/-}$ mice were comparable to similarly treated IFN-$\gamma^{+/+}$ mice, suggesting that the absence of IFN-$\gamma$ in these animals did not completely inhibit development of a humoral immune response after immunization.

Gross examination and histopathology also were analyzed in the IFN-$\gamma^{-/-}$ and IFN-$\gamma^{+/+}$ animals on day 80 after challenge. This individual time-point was chosen for these analyses based on previous experiments in BALB/c animals in which hydrosalpinx formation was not evident until day 50 after challenge and progressively worsened at least until day 80 after challenge. As shown in Table 9, hydrosalpinx was not apparent in rCPAF+IL-12 immunized IFN-$\gamma^{+/+}$ mice (0%), as compared to similarly treated IFN-$\gamma^{-/-}$ mice (100% bilateral). Oviduct dilatation also was minimal in rCPAF+IL-12 immunized IFN-$\gamma^{+/+}$ mice (0.9±0.3) as compared to similarly treated IFN-$\gamma^{-/-}$ mice (3.7±0.33) (FIG. 6A). All rCPAF+IL-12 and mock-vaccinated (PBS) IFN-$\gamma^{-/-}$ mice displayed bilateral hydrosalpinx and confluent oviduct dilatation (3.7±0.3 and 3.8±0.2, respectively), indicating the absence of any protective effect in vaccinated IFN-$\gamma^{-/-}$ animals. Additionally, cellular infiltration into the oviduct and mesosalpingeal tissues was examined on day 80 post-challenge (FIG. 6B). Fewer mononuclear cells were present in oviduct and mesosalpingeal tissues of vaccinated IFN-$\gamma^{+/+}$ mice (1.5±0.2) when compared to similarly treated IFN-$\gamma^{-/-}$ mice (2.25±0.36), while both groups exhibited minimal numbers of plasma cells and PMNs in the tissues. Cellular infiltration in mock-immunized IFN-$\gamma^{+/+}$ and IFN-$\gamma^{-/-}$ mice was comparable. In agreement with the previous experiment in BALB/c mice, rCPAF+IL-12 vaccinated IFN-γ$^{+/+}$ mice exhibited significantly reduced incidence of hydrosalpinx, oviduct dilatation, mononuclear and plasma cell infiltration as compared to mock-vaccinated (PBS) IFN-γ$^{+/+}$ animals. These results collectively suggest that rCPAF+IL-12 mediated protection is highly dependent on the induction of endogenous IFN-γ production.

Example 4

Intranasal Immunization with Chlamydial Protease-Like Activity Factor and CpG Deoxynucleotides Enhances Protective Immunity Against Genital *Chlamydia muridarum* Infection Bacteria *Chlamydia muridarum* was grown on confluent HeLa cell monolayers. Cells were lysed using a sonicator (Fisher, Pittsburgh, Pa.) and elementary bodies (EBs) were purified on Renograffin gradients as described previously (9). Aliquots of bacteria were stored at −70° C. in sucrose-phosphate-glutamine buffer.

CPAF and CpG deoxynucleotides CPAF from the *C. trachomatis* L2 genome was cloned and expressed in a bacterial system as described previously (3). CPAF has been shown to be highly conserved among the different biovars of *Chlamydia*, with 82% amino acid identity between L2 and *C. muridarum* CPAF (18). Additionally, protective efficacy of L2 CPAF against genital *C. muridarum* challenge has been shown (43). Briefly, CPAF constructs cloned from *C. trachomatis* L2 genome with a 6-Histidine tag (His) were cloned into pBAD vectors and expressed in *Escherichia coli* with isopropyl-β-D-thiogalactopyranoside (IPTG) as an inducer. The fusion protein was purified using Ni-NTA agarose beads (Amersham Biosciences Corp.). The purified CPAF was identified by Western blot analysis using a monoclonal anti-CPAF antibody (31). CPAF activity was determined by the ability to degrade the transcription factor RFX-5 in a concentration-dependent fashion, using a cell-free degradation assay, as described previously (13). Purified CPAF was used as a source of protein for all experiments.

CpG oligodeoxynucleotides (5'-TCC ATG ACG TTC CTG ACG TT-3'; designated CpG; SEQ ID NO:7) or non-CpG control oligodeoxynucleotides (5'-TCC AGG ACT TTC CTC AGG TT-3'; designated ODN; SEQ ID NO:8) (32,33) were synthesized and obtained from Sigma Genosys (St. Louis, Mo.).

Mice. Four week-old, female BALB/c mice were obtained from Charles River Laboratory (Bar Harbor, Me.). Mice were housed and bred at the University of Texas at San Antonio and provided food and water ad libitum. Animal care and experimental procedures were performed in compliance with the Institutional Animal Care and Use Committee (IACUC) guidelines.

Immunization procedure. Mice were anesthetized i.n. with 3% isofluorane using a rodent anesthesia system (Harvard Apparatus, Holliston, Mass.). Mice were immunized i.n. or i.p. on day 0 with 15 µg rCPAF dissolved in 25 µl (for i.n.) or 100 µl (for i.p.) of sterile phosphate buffered saline (PBS). This was accompanied on days −1, 0, and +1 with 10 µg of CpG or 10 µg of ODN. Mice were boosted i.n. with 15 µg rCPAF+CpG or ODN on days 14 and 28. Some mice received only CpG or PBS (no CPAF vaccine). The dose of CPAF used was what provided optimal protection in studies with CPAF+ IL-12 in BALB/c mice (43).

Antigen-specific cytokine recall response. Spleens were removed 14 days after primary vaccination and single cell suspensions were prepared to analyze the antigen-specific cytokine response as described previously (39, 43). Collected cells [10$^6$/well] were incubated for 72 hr with 1 µg CPAF per well or with an equal concentration of an unrelated antigen, hen egg lysozyme (HEL), or PBS alone in 96-well culture plates. Supernatants were assayed for levels of interleukin-12 (IL-12), gamma-interferon (IFN-γ) and interleukin-4 (IL-4) using BDOptEIA™ kits (BD Pharmingen, San Diego, Calif.) according to manufacturer's instructions. Absorbance at 630 nm was measured using a µQuant ELISA microplate reader (Biotek Instruments, Winooski, Vt.).

Detection of antibody and isotype levels by ELISA. Ten days following final immunization, animals were bled for serum, or vaginal lavage fluids were obtained and analyzed by ELISA as described previously (39, 43, 44). Microtiter plates (96-well) were coated overnight with 5 µg CPAF in sodium bicarbonate buffer (pH 9.5). Serial dilutions of serum or undiluted vaginal lavage fluids were added to wells followed by either goat anti-mouse total Ig, IgG1, IgG2a, IgG2b, IgM, or IgA conjugated to alkaline phosphatase (Southern Biotechnology Associates, Birmingham, Ala.). After washing, p-nitrophenyl phosphate substrate (Sigma, St. Louis, Mo.) was added for color development and absorbance (O.D.) and monitored at 405 nm using a µQuant ELISA microplate reader (Biotek Instruments). Reciprocal serum dilutions corresponding to 50% maximal binding were used to obtain titers. Because of the low amounts of Ab in vaginal fluids and the large dilution involved in the lavage procedure, these samples were tested undiluted. No binding of immune serum was detected in plates coated with HEL.

Vaginal *C. muridarum* challenge and determination of bacterial shedding. One month following the final vaccination, animals were anesthetized using isofluorane (3%) and challenged i.vag. with 5×10$^4$ inclusion forming units (IFU) of *C. muridarum* in 5 µl of SPG buffer as described previously (39, 43, 44). To synchronize the estrous cycle of animals prior to chlamydial challenge, two doses of depo-provera (Pharmacia Upjohn, Kalamazoo, Mich.) were injected subcutaneously on days −10 and −3 before challenge. To monitor bacterial shedding, vaginal swabs were obtained on the indicated days after vaginal challenge, followed by plating of the swab material on HeLa cell monolayers grown on culture coverslips. Chlamydial inclusions were detected using an anti-*Chlamydia* genus specific murine monoclonal primary antibody and goat anti-mouse IgG secondary antibody conjugated to Cy3 plus Hoescht nuclear stain. The average number of inclusions in 5 random microscopic fields was calculated for each animal for earlier time-points (until day 12 after challenge) and entire coverslips for later time-points (days 15-30 after challenge), and results expressed as average number of inclusions per animal group.

Gross and histopathology. Genital tracts were removed from mice at day 80 after challenge (39, 43, 44), examined for presence of hydrosalpinx, then fixed in 10% neutral formalin, and embedded into paraffin blocks. Serial horizontal sections (5 µm) were prepared and stained using hematoxylin and eosin (H&E). Stained sections were visualized using a Zeiss Axioskop 2 Plus research microscope and images were acquired using an Axiocam digital camera (Zeiss, Thornwood, N.Y.).

Histological scoring. Sections stained with H&E were scored in blinded fashion as described previously (43). Dilatation of oviducts was scored as follows: 0—no significant dilatation, 1—mild dilatation of single cross-section of oviduct, 2—1-3 dilated cross-sections of oviduct, 3—>3 dilated cross-sections of oviduct, or 4—confluent pronounced dilatation of oviduct. Cellular parameters (polymorphonuclear cells (PMNs), mononuclear, and plasma cells) were individually scored as follows: 0—no significant presence of infiltration, 1—presence of infiltration at a single focus, 2—presence at 2-4 foci, 3—presence at more than 4 foci, or 4—confluent infiltration. Results are expressed as mean±SD of scores from all animals in a group.

Statistical analyses. For comparison of two groups, the student's t test (for normally distributed values) or the Mann-Whitney Rank Sum test (for values not distributed normally) was used to compare values of continuous variables. For experiments with four groups of animals, analysis of variance (ANOVA) followed by multiple comparison of means (Kruskall-Wallis test) was used. To analyze differences in the time required for clearance, the Kaplan-Meier test was used. Differences between groups were considered statistically significant if P values were <0.05. All data shown are representative of 2-3 independent experiments and each experiment shown was analyzed independently.

Cellular cytokine responses to CPAF vaccination. Groups of BALB/c mice were immunized i.n. or i.p. with CPAF+CpG, CPAF+ODN or treated with PBS (mock). Fourteen days later, splenocytes were stimulated in vitro with CPAF and antigen specific cytokine production was measured by ELISA. Splenocytes from i.n. CPAF+CpG vaccinated mice stimulated with CPAF exhibited significantly greater IL-12 (538.84±19.21 pg/ml) and IFN-γ production (577.60±30.6 pg/ml) as compared to those from CPAF+ODN immunized animals (93.2±15.5 and 230.38±24.8 pg/ml, respectively). In contrast, splenocytes from i.p. CPAF+CpG vaccinated mice exhibited significantly greater IFN-γ production (385.85±35.36 pg/ml), but minimal levels of IL-12 induction (53.84±19.21 pg/ml), as compared to those from i.p. CPAF+ODN (94.32±20.2 and 3.2±15.5 pg/ml, respectively) vaccinated animals. In either case, cells stimulated with an unrelated antigen, HEL, did not exhibit cytokine production. Furthermore, splenocytes from mock-immunized (PBS) or CpG treated animals did not exhibit CPAF-specific cytokine production. There was no detectable IL-4 production in splenocytes from any animal group. These results demonstrate the induction of a robust CPAF-specific Th1 cellular response after i.n. or i.p. CPAF+CpG vaccination.

Humoral response to CPAF vaccination. Groups of mice were vaccinated i.n. or i.p. with CPAF+CpG, CPAF+ODN, or with CpG or PBS (Mock) alone. Sera and vaginal fluids were assayed for the presence of anti-CPAF antibodies. Two weeks after the final i.n. or i.p. CPAF+CpG vaccination, mice exhibited high titers of serum anti-CPAF total IgG (5957.74±533.73 and 7523.03±677, respectively), IgG1 (6043.9±269.2 and 8008.2±501, respectively), IgG2a (4639.38±409.14 and 3174.83±652.22, respectively) and IgG2b (3811.12±1120.98 and 4849.97±737.35, respectively), when compared to PBS (mock) or CpG alone immunized animals. Intranasal or i.p. immunization with CPAF+ODN induced comparable anti-CPAF total Ab and IgG1 to CPAF+CpG vaccination. However, titers following CPAF+CpG vaccination were significantly elevated for IgG2a (i.n.: 4639.38±409.14 versus 327.87±327.87, and i.p.: 3174.83±652.22 versus 1119.63±503.07, respectively) and IgG2b (i.n.: 3811.12±1120.98 versus 661.41±502.77, and i.p.: 4849.97±737.35 versus 2523.02±321.15, respectively). Vaginal fluid from i.n. or i.p. CPAF+CpG vaccinated mice exhibited significantly elevated levels of anti-CPAF IgA (0.45±0.1 and 0.52±0.05, respectively) when compared to mock vaccinated (PBS) animals. Mice immunized with CPAF+ODN exhibited intermediate levels (0.29±0.06 and 0.27±0.06, respectively) of anti-CPAF IgA as compared to animals vaccinated with CPAF+CpG or those treated with PBS (mock). Animals immunized with PBS (mock) or CpG alone displayed minimal levels of anti-CPAF IgA in the vaginal fluid. There were negligible levels of anti-CPAF IgA in the sera of each group of vaccinated animals. Plates coated with HEL did not display detectable binding of sera or vaginal fluid from any animal group, indicating the specificity of the measured anti-CPAF antibody. These results indicate that i.n. or i.p. vaccination with CPAF+CpG induces strong systemic and mucosal humoral responses against CPAF.

Protective efficacy against genital *C. muridarum* challenge after CPAF vaccination. Groups of mice were vaccinated i.n. or i.p with CPAF+CpG, CPAF+ODN, or with CpG alone or PBS (mock) on days 0, 14, and 28. The mice were rested for a month and then challenged i.vag. with $5 \times 10^4$ IFU *C. muridarum*. Vaginal bacterial recovery was measured at 3-day intervals post-challenge. Mice vaccinated i.n. with CPAF+CpG displayed significantly reduced chlamydial shedding compared to those immunized with PBS (mock) as early as day 12 after challenge. Complete resolution of infection was observed in 75% of i.n. CPAF+CpG vaccinated mice on day 12, 84% on day 15, and 100% on day 18 after challenge. In comparison, mice vaccinated with CPAF+ODN resolved the infection completely between days 15 and 21, whereas mock-immunized animals resolved the bacterial infection between 24 and 30 days post-challenge.

Mice vaccinated i.p. with CPAF+CpG also displayed significantly reduced chlamydial shedding as compared to mock-immunized animals as early as day 12 after challenge. Complete resolution in CPAF+CpG i.p. vaccinated mice was observed in 38% of animals on day 15, 63% on day 18, and 100% by day 21 after challenge. In comparison, mice vaccinated i.p. with CPAF+ODN displayed resolution between days 18-24, and mock-immunized animals between days 24-30 after challenge. These results demonstrate the comparable efficacy of i.n. and i.p. CPAF+CpG vaccination in accelerating clearance of *Chlamydia* from the genital tract. Additionally, vaccination with CPAF+ODN also enhanced the resolution of infection compared to mock-immunized animals, but with delayed kinetics in comparison to animals vaccinated with CPAF+CpG.

Histopathological analysis of genital tissues. The effect of CPAF+CpG vaccination on the development of genital tract pathology (hydrosalpinx) was examined on day 80 following vaginal chlamydial challenge. Mice vaccinated i.n. or i.p. with CPAF+CpG exhibited minimal development of hydrosalpinx (0% bilateral, 16% unilateral or 0% bilateral, 33% unilateral, respectively) as compared to mock-immunized animals (66% bilateral, 16% unilateral) (FIG. 7A). Mice vaccinated i.n. or i.p. with CPAF+ODN displayed an intermediate degree of protection against hydrosalpinx (33% bilateral, 16% unilateral, for each) when compared to CPAF+CpG vaccinated and mock-immunized animals.

The development of histopathology and cellular infiltration at day 80 after challenge in vaccinated animals was further scored in a blinded fashion as described previously [6]. CPAF+CpG vaccinated animals displayed minimal oviduct dilatation (0.41±0.19) as compared to mock-immunization with PBS (2.41±0.43) (FIG. 7B). In addition, CPAF+CpG vaccinated animals displayed significantly reduced infiltration of PMNs (1.33±0.16), mononuclear cells (1.45±0.18), and plasma cells (0.41±0.08), as compared to mock-immunized animals (3.5±0.28, 3.2±0.17, 1.92±0.15, respectively) (FIG. 7C). In addition, animals vaccinated with CPAF+ODN exhibited intermediate degrees of oviduct dilatation (1.41±0.39), and inflammatory cellular infiltration (PMNs: 2.83±0.15, mononuclear cells: 3±0.01, plasma cells: 1.38±0.17, respectively). These results indicate that apart from enhancing resolution of infection, vaccination with CPAF+CpG induces protection against oviduct pathology and reduces inflammatory cellular infiltration.

Example 5

The protective efficacy of recombinant proteins from *C. trachomatis* serovar D (a common cause of chlamydial STD in humans)—MOMP (rMOMP), IncA (rIncA), or CPAF (rCPAF) against vaginal *C. muridarum* challenge was examined in this study. Female BALB/c animals were intranasally immunized with the proteins individually or in combinations, with murine recombinant interleukin-12 (IL-12), a well established mucosal Th1 adjuvant (1, 34, 35), and evaluated for the induction of cross-species protection against *C. muridarum* challenge. Animals vaccinated with rCPAF+IL-12 alone exhibited significantly accelerated resolution of genital infection as well as minimal development of oviduct pathology. However, there was no significant additive or synergistic effect of the other evaluated antigen(s) to the cross-species protective immunity induced by rCPAF+IL-12 vaccination alone.

Recombinant proteins. The recombinant chlamydial proteins were purified as previously described (25, 43). The sequences of MOMP (NCBI nucleotide accession: X77364), IncA (AF326998), and CPAF (13) from serovar D were used for generation of the recombinant proteins. Briefly, rMOMP and rIncA were cloned into PGEX vectors and expressed with glutathione S-transferase fused to the N-terminus of the protein. Since the sequence of CPAF from serovar D and serovar L2 share 99% amino acid identity with each other (18), and 82% identity each with *C. muridarum* CPAF (18), an existing rCPAF construct generated using sequence from the *C. trachomatis* L2 genome with a 6x-Histidine tag cloned into pBAD vectors was used (13, 38, 39, 43, 44). The fusion proteins were expressed in *Escherichia coli* with L-arabinose (for rCPAF) or isopropyl-β-D-thiogalactopyranoside (for rMOMP and rIncA) as an inducer and extracted by bacterial lysis using sonication in a Triton X-100 lysis buffer. Ni-NTA agarose beads (Amersham, N.J.) were used for purification of rCPAF, and glutathione-conjugated agarose beads (Pharmacia & Upjohn, MI) for rMOMP and rIncA. Each fusion protein was concentrated using Centriplus YM-10 tubes (Millipore, Mass.), suspended in PBS with proteinase inhibitor cocktail (Roche, Calif.), aliquoted, and then stored at −20° C. The purity of each protein was evaluated by SDS-polyacrylamide gel electrophoresis and by Western blot using antigen-specific murine antibodies (13). As a standard procedure, the endotoxin levels in the purified protein samples were measured using the *Limulus* Amebocyte Assay (Sigma-Aldrich, MO) and were consistently found to be <1 endotoxin unit (EU)/mg of protein [1 EU=0.2 ng]. Murine recombinant IL-12 was obtained from Wyeth (Cambridge, Mass.).

Bacteria. *Chlamydia muridarum* was grown on confluent HeLa cell monolayers. Cells were lysed using a sonicator (Fisher Scientific, PA) and elementary bodies (EBs) were purified on Renograffin gradients as described previously (9). Aliquots of bacteria were stored at −70 C. in sucrose-phosphate-glutamine (SPG) buffer.

Mice. Four-to-six week-old, female BALB/c mice were obtained from Charles River Laboratory (Bar Harbor, Me.). Mice were housed and bred at the University of Texas at San Antonio and provided food and water ad libitum. Animal care and experimental procedures were performed in compliance with the Institutional Animal Care and Use Committee (IACUC) guidelines.

Intranasal immunization procedure. Animals were immunized as described previously (38, 39, 43, 44). Groups of mice were anesthetized (3% isofluorane) and immunized intranasally (i.n.) on day 0 with 15 µg rCPAF, 15 µg rMOMP, or 15 µg rIncA alone or with combinations of 15 µg rCPAF+15 µg rMOMP, 15 µg rCPAF+15 µg rIncA, or 15 µg rCPAF+15 µg rMOMP+15 µg rIncA, all dissolved in 25 µl of sterile PBS. This was accompanied on days −1, 0, and +1 with 0.5 µg of recombinant murine IL-12 (Wyeth, Mass.) in PBS containing 1% normal mouse serum. Mice were boosted i.n. with the same doses on days 14 and 28. The dose of rCPAF that was selected (15 µg/mouse) provided optimal protection against genital *C. muridarum* challenge in studies using BALB/c mice (38, 39, 43, 44). Equivalent doses of the other antigens (rMOMP and rIncA) were used for this comparative study. Some mice received 15 µg of the unrelated antigen hen egg lysozyme (HEL)+0.5 µg IL-12, 0.5 µg IL-12 alone, or PBS (mock) alone as controls. As previously described, no significant toxicity was observed with the IL-12 treatment regimen (4, 38).

Antigen-specific $CD4^+$ T cell responses. Fourteen days after i.n. immunization with individual recombinant chlamydial antigens, spleens were removed and splenocytes were layered over a Ficoll density gradient to collect mononuclear cells. $CD4^+$ T cell populations were isolated using magnetic particles (Stem Cell Technologies, Canada) and the purity was determined to be at least >95% of $CD4^+$ T cells by flow cytometry using an allophycocyanin-conjugated anti-CD4 monoclonal antibody (BD Biosciences, CA). A separate pool of naïve splenocytes was prepared from PBS (mock) immunized animals and treated with mitomycin C (25 µg/$10^7$ cells) for 20 min and used as a source of antigen presenting cells (APCs) (38). The purified $CD4^+$ T cells ($10^5$ cells/well) were cultured with APCs ($10^5$ cells/well) and stimulated for 72 hr in vitro with individual recombinant chlamydial antigens (1 µg/ml), or with the unrelated antigen HEL (1 µg/ml), UV-inactivated *C. muridarum* ($10^5$ IFU/well), or medium alone in culture plates. Supernatants from the culture wells were analyzed for IFN-γ and IL-4 production using BD OptELISA kits (BD Pharmingen, NJ) as described previously (38, 39, 43, 44).

Detection of antibody and isotype levels by ELISA. Ten days after the final immunization, sera from the animals were analyzed by ELISA as described previously (9, 38, 39, 43, 44). Microtiter plates were coated overnight with rCPAF (5 µg/ml) in sodium bicarbonate buffer (pH 9.5). Serial dilutions of serum were added to wells followed by either goat anti-mouse total Ig, IgG1, IgG2a, IgG2b, IgM, or IgA conjugated to alkaline phosphatase (Southern Biotechnology Associates, AL). After washing, p-nitrophenyl phosphate substrate (Sigma, Mo.) was added for color development and the absorbance at 405 nm measured using a µQuant microplate reader (Biotek Instruments, VT). Reciprocal serum dilutions corresponding to 50% maximal binding were used to obtain titers.

Vaginal *C. muridarum* challenge and determination of bacterial shedding. One month following the final vaccination, animals were challenged intravaginally (i.vag.) with $10^5$ inclusion forming units (IFU) of *C. muridarum* in 5 µl of SPG buffer as described previously (38, 39, 43, 44). The estrous cycle of animals was synchronized using two subcutaneous injections of Depo-Provera (Pharmacia Upjohn, Mich.) on days −10 and −3 before challenge. Vaginal swabs were obtained on the indicated days after challenge, followed by plating of the swab material on HeLa cell monolayers grown on culture coverslips. Chlamydial inclusions were detected using an anti-*Chlamydia* genus-specific murine monoclonal primary antibody and goat anti-mouse IgG secondary antibody conjugated to FITC plus Hoescht nuclear stain. The number of inclusions was counted under a Zeiss Axioskop microscope and results expressed as the average number of inclusions per animal group.

Gross and histopathology. Genital tracts were removed from mice at various indicated time-points after challenge, examined for the presence of hydrosalpinx, then fixed in 10% neutral formalin, and embedded into paraffin blocks. Serial horizontal sections (5 μm) were prepared and stained using hematoxylin and eosin (H&E). Stained sections were visualized using a Zeiss Axioskop microscope and scored in blinded fashion as described previously (43). Dilatation of oviducts was scored as follows: 0—no significant dilatation, 1-mild dilatation of a single cross-section of oviduct, 2—1-3 dilated cross-sections of an oviduct, 3—>3 dilated cross-sections of an oviduct, 4—confluent pronounced dilatation of the oviduct. Cellular parameters (polymorphonuclear cells (PMNs), mononuclear, and plasma cells) were individually scored as follows: 0—no significant presence of infiltration, 1—presence of infiltration at a single focus, 2—presence at 2-4 foci, 3—presence at more than 4 foci, or 4—confluent infiltration. Results are expressed as mean±SD of scores from all animals in a group.

Statistical analyses. For comparison of two groups, the student's t test (for normally distributed values) or the Mann-Whitney Rank Sum test (for values not distributed normally) were used to compare values of continuous variables. For experiments with more than two groups of animals, analysis of variance (ANOVA) followed by multiple comparison of means (Kruskall-Wallis test) was used. To analyze differences in the time required for bacterial clearance, the Kaplan-Meier test was used. Differences between groups were considered statistically significant if P values were <0.05. All data shown are representative of 2-3 independent experiments and each experiment shown was analyzed independently.

Purification of recombinant chlamydial proteins. Recombinant CPAF, rIncA, or rMOMP were cloned and expressed as described previously (25, 43). Each purified protein exhibited a distinct band (rCPAF-72 kDa; rMOMP-66 kDa; rIncA-56 kDa) after SDS-polyacrylamide gel electrophoresis and staining with Coomassie blue. The purity of the proteins was further confirmed by Western blot using antigen-specific monoclonal antibodies, then aliquoted and used as a source of recombinant protein for all experiments.

Cellular response after intranasal immunization. Groups of animals were vaccinated individually with rCPAF, rIncA, rMOMP, the unrelated antigen HEL, or PBS (mock). Additionally, all groups of animals (with the exception of mock vaccinated animals) received IL-12 on days −1, 0, and +1. Fourteen days after immunization, purified $CD4^+$ T-cells were cultured with mitomycin-C treated APCs and stimulated for 72 h with 1 μg of individual antigen, UV-inactivated $C.$ $muridarum$ ($10^5$ IFU/well), or medium alone and supernatants were analyzed for IFN-γ and IL-4 production. As shown in Table 1, mice vaccinated with rCPAF exhibited the highest antigen-specific IFN-γ production (1525±172 pg/ml) when compared to mice immunized with rMOMP (228±72 pg/ml) or rIncA (972±128 pg/ml). Additionally, purified $CD4^+$ T-cells from $C.$ $muridarum$ infected animals exhibited the greatest IFN-γ production upon stimulation with rCPAF (295±95 pg/ml), followed by rIncA (270±80 pg/ml) and rMOMP (155±45 pg/ml), respectively. As expected, purified $CD4^+$ T cells from $C.$ $muridarum$ infected animals exhibited high levels of IFN-γ production (1305±113 pg/ml), and minimal IL-4 production (below the limit of detection) upon in vitro stimulation with UV-inactivated $C.$ $muridarum$ EBs. Purified $CD4^+$ T-cells from HEL+IL-12, IL-12 alone, or PBS (mock) immunized animals displayed minimal IFN-γ production upon stimulation with any chlamydial antigen, indicating the specificity of the measured cytokine responses. These results indicate that immunization with rCPAF, rIncA, or rMOMP elicit Th1 type cellular responses; but rCPAF elicits the greatest induction of IFN-γ production among these antigens.

Humoral response after intranasal immunization. Groups of animals were vaccinated individually with rCPAF, rIncA, rMOMP, HEL, or PBS (mock), or in combinations of rCPAF+rIncA, rCPAF+MOMP, or rCPAF+rIncA+rMOMP on days 0, 14, and 28, respectively. Additionally, all groups of animals (except mock) received IL-12 on days −1, 0, +1, 14 and 28. The serum antibody responses against rCPAF, rIncA, or rMOMP were measured ten days after the last booster immunization. As shown in Table 2A, animals vaccinated with rCPAF alone or in combination with any antigen displayed high titers of serum anti-rCPAF total antibody, IgG1, IgG2a and IgG2b. These antigen-specific antibody and isotype responses also were observed after vaccination with rMOMP (Table 2B) or rIncA (Table 2C). As expected, HEL+IL-12, IL-12 alone or PBS (mock) immunized animals exhibited minimal anti-CPAF, anti-IncA, or anti-MOMP antibodies (Table 2A-C). The purity of the antigens and the specificity of immune responses were further confirmed by the minimal levels of cross-reactive antibodies in vaccinated mice.

Chlamydial clearance after genital challenge in vaccinated animals. Groups of animals were vaccinated individually with rCPAF, rIncA, and rMOMP, or in combinations of rCPAF+rIncA, rCPAF+rMOMP, and rCPAF+rIncA+rMOMP, or with HEL and PBS (mock) on days 0, 14 and 28 respectively. Additionally, all groups of animals (except mock) received IL-12 on days −1, 0, +1, 14 and 28. The efficacy of the different vaccination regimens against genital $C.$ $muridarum$ challenge was examined by monitoring vaginal chlamydial shedding at three-day intervals after challenge. As shown in Table 3, vaccination with rCPAF+IL-12 induced resolution of infection in 33% of mice as early as day 12, in 67% of mice by day 15, and 100% of mice by day 18 after challenge, respectively. In comparison, the majority of rMOMP or rIncA vaccinated animals were still shedding $Chlamydia$ at day 18 after challenge (67% or 50%, respectively). The majority (83% each) of the rMOMP or rIncA vaccinated animals displayed resolution of infection at day 24, with 100% mice exhibiting resolution on day 27 after challenge. Furthermore, the addition of rMOMP, rIncA, or both, to the rCPAF+IL-12 vaccination regimen did not significantly enhance the kinetics of bacterial resolution compared to vaccination with rCPAF+IL-12 alone, with 100% of animals in each group resolving the infection by day 18 after chlamydial challenge. Animals immunized with PBS (mock) or the unrelated antigen (HEL+IL-12) began to resolve the infection between days 21-30 after challenge. As previously shown (43), resolution of infection in animals treated with IL-12 alone was comparable to PBS (mock) animals. These results clearly demonstrate the efficacy of rCPAF in enhancing the chlamydial clearance compared to the other antigens that contributed minimally to the rCPAF+IL-12 regimen.

$Chlamydia$-induced upper genital tract pathology in vaccinated animals. The major problem with genital chlamydial infections in humans is the development of inflammatory complications in the upper genital tract (2, 7). Likewise, mice infected i.vag. with $C.$ $muridarum$ develop typical complications in the upper genital tract such as hydrosalpinx and oviduct dilatation (7). The effect of the vaccination regimen on the development of upper genital tract pathology was examined on day 80 after challenge. As shown in Table 4A, 83% of PBS (mock) immunized animals displayed bilateral hydrosalpinx on day 80 after chlamydial challenge. In comparison, rCPAF+IL-12 vaccination prevented the development of hydrosalpinx in the majority of the animals (0% bilateral, 33% unilateral). An intermediate degree of protection against oviduct pathology was observed in rMOMP+IL-12 (33% bilateral, 33% unilateral) or rIncA+IL-12 (50% bilateral, 17% unilateral) vaccination. Furthermore, the effect of rCPAF+rMOMP+IL-12 (0% bilateral, 17% unilateral), rCPAF+rIncA+IL-12 (0% bilateral, 0% unilateral) or rCPAF+rMOMP+rIncA+IL-12 (17% bilateral, 17% unilateral) was not significantly different from that of vaccination with rCPAF+IL-12 alone (0% bilateral, 33% unilateral). As expected, animals vaccinated with HEL+IL-12 displayed comparable incidence of hydrosalpinx (67% bilateral, 17% unilateral) to PBS (mock) immunized animals.

The incidence of oviduct dilatation and cellular infiltration also was scored on day 80 after challenge. As shown in Table 4B, PBS (mock) immunized animals displayed a high degree of oviduct dilatation (2.41±0.23) on day 80 after chlamydial challenge. Animals vaccinated with rCPAF+IL-12 displayed significantly reduced dilatation of oviducts (0.66±0.21) compared to PBS (mock) immunized animals. Animals vaccinated with the combinations rMOMP+IL-12 (1.18±0.23) or rIncA+IL-12 (1.25±0.21) also displayed significant reduction in oviduct dilatation, compared to PBS (mock) immunized animals, but not as great a reduction as the CPAF immunized animals. Animals vaccinated with the combinations rCPAF+rMOMP+IL-12 (0.5±0.13), rCPAF+rIncA+IL-12 (0.5±0.12), or rCPAF+rMOMP+rIncA+IL-12 (0.67±0.3) displayed reduced oviduct dilatation that was not statistically different from animals vaccinated with rCPAF+IL-12 alone (0.66±0.21). The infiltration of PMNs, mononuclear cells and plasma cells also was examined and found to be reduced in animals vaccinated with rCPAF+IL-12 alone or in combination with the other antigens, with significant reductions in mononuclear and plasma cell frequencies (Table 4C). Animals vaccinated with rMOMP+IL-12 or rIncA+IL-12 alone displayed reduced, albeit not significantly, numbers of all cell types examined compared to PBS (mock) immunized animals on day 80 after challenge. Collectively, these analyses demonstrate the greater efficacy of rCPAF+IL-12 as compared to rMOMP+IL-12 or rIncA+IL-12 in reducing the development of oviduct pathology after genital chlamydial challenge.

The presence of multiple serovars of *Chlamydia trachomatis* that cause genital infections suggests the need to identify vaccine candidates that provide cross-serovar protection. This study demonstrates that rCPAF+IL-12 vaccination enhances chlamydial clearance and reduces the development of oviduct pathology (38, 39, 43), but does not induce complete resistance to infection. This study employed a recombinant multi-subunit vaccination approach with three defined chlamydial antigens including rMOMP, rIncA, and rCPAF from *C. trachomatis* serovar D, individually or in combinations, with IL-12 as an adjuvant, and studied the cross-species protective efficacy against vaginal *C. muridarum* challenge.

Multiple serovars (D-L) of the organism cause genital infections in humans. Therefore, an ideal anti-chlamydial vaccine should induce cross-serovar immunity. A consideration for inducing cross-serovar protection is that even subtle variations in the amino acid sequence of a protein across chlamydial serovars might significantly affect the secondary and tertiary protein conformation. Therefore, without wishing to be bound to a particular theory, there is a greater likelihood of conservation of protective linear epitopes compared to conformational epitopes. To this end, T cells recognize only linear antigenic epitopes, whereas B cells can directly recognize conformational epitopes, suggesting that the induction of T cell, but not B cell, mediated immunity, may be suitable for generating cross-serovar protection. This also is corroborated by the fact that T helper 1 (Th1) type CD4$^+$ T cells, that recognize only linear epitopes, are required for optimal resolution of genital chlamydial infection. The screening of such conserved protective linear T cell epitopes can be accomplished using recombinant candidate antigens generated by heterologous (e.g., *Escherichia coli*, used in this study) expression vector systems.

After intranasal immunization, all the respective antigens induced robust CD4$^+$ Th1 type antigen-specific cellular responses, indicated by high levels of IFN-γ but minimal IL-4 production. However, both rCPAF and rIncA immunization induced significantly higher (p<0.05) IFN-γ responses than rMOMP vaccination. Additionally, while each chlamydial antigen tested induced high levels of serum antibody, rCPAF or rIncA induced greater levels of IgG2a compared to IgG1, whereas rMOMP induced greater IgG1 compared to IgG2a production. These results indicate that rCPAF or rIncA may be more potent Th1 immunogens compared to rMOMP. In this regard, Th1 responses have been shown to be highly important for protective immunity against primary genital chlamydial infection (22, 36, 40, 41). Specifically, mice depleted of CD4$^+$ T-cells or those deficient in MHC class II production displayed inability to resolve genital chlamydial infection (8, 39). Additionally, mice deficient in IFN-γ production displayed inability to optimally resolve and prevent dissemination of chlamydial infections (16, 19, 20, 22, 41, 44).

Vaccination with rCPAF+IL-12 resulted in significantly accelerated resolution of genital chlamydial infection, as well as reduction in the incidence of hydrosalpinx, oviduct dilatation, and cellular infiltration. These results are in agreement with studies (38, 39, 43, 44) demonstrating the protective efficacy of rCPAF against genital chlamydial infections. Additionally, the incorporation of rMOMP, rIncA, or both into the rCPAF+IL-12 treatment regimen resulted in levels of protective immunity comparable to vaccination with rCPAF+IL-12 alone. The failure to elicit additive or synergistic protective immunity with these combination regimens may suggest the immunogenic dominance of rCPAF when compared to rMOMP or rIncA. To this end, Sharma et al. (11, 12, 25) have demonstrated that CPAF was a dominant immunogen in *Chlamydia* sero-positive humans, when compared to a wide repertoire of other chlamydial proteins. Given that CPAF is a bacterial protein secreted only in later phases of the chlamydial life cycle (~12-18 hr after initial infection), it would not be expected that immune responses against this antigen provided better protection than rMOMP or rIncA. The ability of CPAF to be actively secreted into the host cytosol may influence antigen presentation and subsequent activation of cell-mediated responses (3, 13, 18, 29, 30, 49). In this regard, rCPAF+IL-12 induced immunity has been shown to be highly dependent upon antigen-presentation via the MHC class-II pathway (39), CD4$^+$ T-cells (38), and endogenous IFN-γ production (43). An alternative possibility as to why rMOMP and/or rIncA did not provide an additive effect to the rCPAF+IL-12 regimen was that the *C. trachomatis* serovar D proteins exhibit different degrees of amino acid identity (MOMP-82%; IncA-52%; and CPAF-82%) with the respective proteins from *C. muridarum*. While IncA inherently has low amino acid identity, MOMP and CPAF share comparable levels of sequence identity. However, the differential induction of cross-serovar protection in this study suggests that the protective linear epitopes in CPAF, not MOMP, are conserved.

The minimal contribution of rMOMP and rIncA to the cross-species protection induced by rCPAF in this study does not exclude the possibility that these recombinant proteins could induce cross-serovar (intra-species) immunity. Conversely, the usage of rMOMP or rIncA from serovar D may provide better immune protection against challenge with the same serovar or other human serovars. A vaccination study with recombinant human serovar proteins in direct protection against human serovar chlamydial infection in mice has constraints, including the strict host tropism linked to differential IFN-γ sensitivity of Chlamydia (10), and therefore, the limited infectivity of human serovars in mice. This issue may be overcome by using humanized mouse models of infection (37, 42). Such mice have been used to study other infectious agents, including human immunodeficiency virus (HIV) and Epstein-Barr virus (EBV), as well as the Toxic Shock Syndrome Toxin-1 (TSST-1) (37, 42). The results from this study also do not exclude the possibility of cross-protective conformational epitopes within MOMP or IncA. Such issues may be addressed using proteins purified from the bacterium and refolded to native configuration, as has been demonstrated for chlamydial MOMP (21). However, the refolding of proteins for vaccine may be tedious compared to the ease of mass-producing recombinant proteins.

In summary, the present study shows that vaccination with rCPAF+IL-12 accelerated chlamydial clearance, reduced the development of oviduct pathology, and induced strong cross-species protection, all to a much greater extent than rMOMP+IL-12 or rIncA+IL-12. Furthermore, the addition of rMOMP and/or rIncA to the rCPAF+IL-12 regimen did not contribute significantly to protective immunity against *C. muridarum*, supporting the utility of rCPAF as a component of an effective anti-chlamydial vaccine in induction of cross-serovar protective immunity.

Example 6

Chlamydial protease-like activity factor (CPAF) (3, 11-13, 18, 25, 49), which previously has been shown to be a protective chlamydial vaccine antigen (38, 39, 43, 44), was used in the present study to examine the requirement and sufficiency of IFN-γ production from Ag-specific CD4$^+$ T cells in protective anti-chlamydial immunity. Using a two-step approach, including vaccination and adoptive transfer of CPAF-specific CD4$^+$ T cells involving IFN-γ$^{+/+}$ mice and IFN-γR$^{-/-}$ mice, this study shows that IFN-γ secretion from Ag-specific CD4$^+$ T cells is necessary and that such cells produce sufficient IFN-γ to induce robust protective anti-chlamydial immunity.

Recombinant (r) CPAF and adjuvant. rCPAF constructs from *C. trachomatis* L2 genome with a 6×-Histidine tag (His) were cloned into pBAD vectors, expressed in *Escherichia coli* and purified using Ni-NTA agarose beads, as described previously (3, 38, 39, 43, 44). The purity of the proteins was confirmed by SDS-PAGE and Western blot. CpG oligodeoxy-nucleotides (5'-TCC ATG ACG TTC CTG ACG TT-3', designated "CpG" herein) were synthesized and obtained from Sigma Genosys (St. Louis, Mo.) (44).

Bacteria. *Chlamydia muridarum* was grown on confluent HeLa cell monolayers as described previously (9). Cells were lysed using a sonicator and elementary bodies (EBs) purified on Renograffin gradients. Aliquots of bacteria were stored at −70° C. in sucrose-phosphate-glutamine (SPG) buffer.

Mice. Four-to-six week old female C57BL/6, BALB/c, C57BL/6 IFN-γ receptor deficient mice (IFN-γR$^{-/-}$ mice, BALB/c IFN-γ deficient mice (IFN-γ$^{-/-}$ mice) and C57BL/6 β$_2$ microglobulin deficient mice (β$_2$m$^{-/-}$ mice) were purchased from Jackson Laboratory (Bar Harbor, Me.). Mice were housed and bred at the University of Texas at San Antonio. Animal care and experimental procedures were performed in compliance with the Institutional Animal Care and Use Committee (IACUC) guidelines.

Intranasal (i.n.) immunization. Animals were immunized as previously described (38, 39, 43, 44). Groups of mice were anesthetized and immunized i.n. on day 0 with 15 µg rCPAF+10 µg CpG dissolved in 25 µl of sterile PBS. Mice were boosted i.n. with the same doses on days 14 and 28. Groups of mice that received PBS (mock) alone served as controls.

Purification of CD4$^+$ T cells. CD4$^+$ T cells were purified as described previously (38). Briefly, splenocytes were layered over a ficoll density gradient to collect mononuclear cells. CD4$^+$ T cell populations were isolated using magnetic particles (Stem Cell Technologies, Canada).

Ag-specific T cell responses. Single cell suspensions from spleens or collagenase-DNase treated genital tracts were prepared from vaccinated animals at the indicated time-periods. Splenocytes (10$^6$ cells/well) or genital tract cells (10$^5$ cells/well), collected before chlamydial challenge, were stimulated for 72 h in vitro with rCPAF (1 µg/ml) or with the unrelated antigen hen egg lysozyme (HEL, 1 µg/ml), or media alone. Cells collected on days 3 and 6 after challenge were cultured in media alone for 72 h to examine the in vivo recall response. Culture supernatants were analyzed for IFN-γ, IL-2 and IL-4 production using BD OptEIA kits (BD Pharmingen, NJ).

Adoptive transfer of CD4$^+$ T cells and vaginal chlamydial challenge. Mice were vaccinated intranasally (i.n.) with three doses of rCPAF+CpG or PBS (mock). Ten days following the last boost, CD4$^+$ T cells were purified and labeled with Car-boxyFluoroscein Succinimidyl Ester (CFSE, Molecular Probes, OR: 2 µM per 10$^7$ cells) (45, 46). The CFSE labeled cells were injected (10$^7$ cells/mouse) intraperitoneally (i.p.) into female C57BL/6 mice. Two hours before transfer, recipient animals were challenged i.vag. with 10$^5$ IFU of *C. muridarum* or PBS (mock). On days 0, 3 or 6 after challenge, CFSE$^+$ cells within genital tract cell suspensions were enumerated by flow cytometry (Becton Dickenson LSR II). In some experiments, unlabelled purified CD4$^+$ T cells (10$^7$ cells/mouse) were transferred into recipient *Chlamydia*-challenged mice and bacterial shedding was monitored. For vaccination/challenge experiments, animals were challenged one month following the final vaccination. In all experiments, the estrous cycle of animals was synchronized using two subcutaneous injections of Depo-Provera (Pharmacia Upjohn, Mich.) on days 10 and 3 before chlamydial challenge.

Vaginal chlamydial shedding and oviduct pathology. Vaginal swab material from the indicated days after challenge was plated onto HeLa cell monolayers. Chlamydial inclusions were probed using an anti-*Chlamydia* murine monoclonal antibody (43) and Cy3 conjugated anti-mouse IgG secondary antibody, plus Hoescht nuclear stain, and counted using a Zeiss Axioskop microscope. On day 80 after challenge, animals were euthanized, dissected, and the number with bilateral or unilateral hydrosalpinx enumerated.

Statistics. SIGMA STAT software (Systat Software Inc., San Jose, Calif.) was used to perform all tests of significance. ANOVA was used for comparisons between multiple groups. Kaplan-Meier test was used for comparisons of time to bacterial clearance. $p<0.05$ was considered statistically significant. All data are representative of two independent experiments and each experiment was analyzed independently.

CPAF-specific IFN-γ induction in the genital tract correlates with the onset of chlamydial clearance. Animals vaccinated i.n. with rCPAF plus adjuvant display significant reduction in vaginal chlamydial shedding compared to mock-vaccinated mice, beginning around day 6 after challenge (38, 39, 43, 44). Local IFN-γ production has been shown to be important for optimal resolution of genital chlamydial infection (17, 19, 20, 22, 24), and the protective effects of CPAF vaccination were highly dependent upon endogenous IFN-γ production (43). Therefore, the temporal induction of genital IFN-γ production was examined in vaccinated/challenged mice. Splenocytes, not genital tract cells, from rCPAF+CpG or rCPAF alone vaccinated animals displayed elevated levels of CPAF-specific IFN-γ production before challenge (day 60 after initial immunization). Additionally, the splenocytes and genital tract cells from rCPAF+CpG vaccinated mice displayed elevated levels of IFN-γ production only on day 6, not day 3, after chlamydial challenge. rCPAF alone vaccinated animals displayed IFN-γ production from spleens, but not genital tracts, on day 6 after challenge. Animals treated with CpG or PBS (mock) did not display Ag-specific cytokine production even at day 6 after challenge. There was minimal IL-4 production in all cultures. As expected, incubation with HEL or medium alone did not induce Ag-specific cytokine production. Collectively, these results indicate that vaccinated animals display genital Ag-specific IFN-γ production after a brief lag following chlamydial challenge, and that rCPAF+CpG immunization induced Ag-specific IFN-γ production within the genital tracts as early as day 6 after challenge. Moreover, rCPAF+CpG vaccinated animals, but not other groups of animals, displayed early reduction in bacterial shedding at day 6 after challenge (39, 43), suggesting a strong correlation between bacterial clearance and local, not splenic, Ag-specific IFN-γ production in the genital tracts.

CPAF-specific CD4$^+$ T cell infiltration into the genital tract correlates with chlamydial clearance. Since CD4$^+$ T cells are a significant source of IFN-γ production, and rCPAF-mediated immunity was strongly dependent upon Ag-specific CD4$^+$ T cells (38), the infiltration of adoptively transferred CFSE-labeled CPAF-specific CD4$^+$ T cells into the genital tract after challenge was examined. The transferred cells contained at least 98% CD4$^+$ T cells as determined by flow cytometry using an allophycocyanin-conjugated anti-CD4 monoclonal antibody (BD Biosciences, CA). Minimal CFSE$^+$ cells were observed in the genital tract of each group of animals on day 3 after C. muridarum or mock (PBS) challenge. On day 6 after C. muridarum challenge, genital tracts of mice that received CPAF-specific CD4$^+$ T cells displayed a higher frequency of CFSE$^+$ cells (28.3%), when compared to animals receiving mock (PBS) CD4$^+$ T cells (9.8%). Mock-challenged mice receiving either group of CD4$^+$ T cells displayed minimal influx of CFSE$^+$ cells into the genital tracts at each time-period examined after challenge. These results suggest that: (a) Ag-specific, not mock (PBS), CD4$^+$ T cells respond early to the infection site; and (b) initiation of an infection is required for homing of primed-CD4$^+$ T cells into the genital tract. Moreover, the temporal kinetics of the cellular infiltration correlates with local IFN-γ production and onset of bacterial clearance from the genital tract. Together, these results suggest the importance of genital CPAF-specific IFN-γ inducing CD4$^+$ T cells in resolution of genital chlamydial infection after CPAF vaccination.

CPAF-specific CD4$^+$ T cell induced chlamydial clearance is mediated by IFN-γ (FIG. 1). Given the pivotal importance of IFN-γ for chlamydial clearance (2, 7, 17, 19, 20, 22, 24) and the correlation of genital Ag-specific CD4$^+$ T cell infiltration to IFN-γ production, the dependency of CPAF-specific CD4$^+$ T cells on this cytokine for chlamydial clearance was evaluated. Purified CD4$^+$ T cells from rCPAF+CpG or mock (PBS) vaccinated C57BL/6 mice were transferred (10$^7$ cells/mouse) into recipient C. muridarum-challenged IFN-γ$^{+/+}$ or C57BL/6 IFN-γ$^{-/-}$ mice, and bacterial shedding was measured at the indicated time periods. IFN-γ$^{+/+}$ mice that received CPAF-specific CD4$^+$ T cells completely resolved the infection by day 18 post-challenge. In contrast, 100% of the IFN-γ$^{-/-}$ mice receiving CPAF-specific or mock (PBS) CD4$^+$ T cells were shedding Chlamydia at day 18, with only 50% of animals in each group resolving the infection by day 30 after challenge. As expected, IFN-γ$^{+/+}$ mice receiving mock (PBS) CD4$^+$ T cells completely resolved the infection by day 27 after challenge. These results clearly demonstrate that CPAF-specific CD4$^+$ T cells induce resolution of genital chlamydial infection in a highly IFN-γ dependent fashion, and that other cytokines from these cells may not contribute significantly in the absence of IFN-γ to chlamydial clearance.

CPAF-specific CD4$^+$ T cells are a sufficient source of IFN-γ production for chlamydial clearance (FIGS. 2A-C). Although the requirement for IFN-γ in anti-chlamydial immunity is known (2, 7, 17, 19, 20, 22, 24), the specific cell types required for optimal induction of this cytokine have not been specifically demonstrated. To address this issue, groups of IFN-γ$^{-/-}$ mice and corresponding wild type IFN-γ$^{+/+}$ mice were immunized with three doses of CPAF+CpG on days 0, 14, and 28. Ten days after the last boost, splenocytes isolated from vaccinated IFN-γ$^{-/-}$ mice as expected did not exhibit IFN-γ production, but displayed levels of Ag-specific IL-2 production comparable to similarly treated IFN-γ$^{+/+}$ mice, suggesting that CD4$^+$ T cells did get primed in an IFN-γ deficient environment. The splenic CD4$^+$ T cells were purified from these animals and transferred i.p. into recipient C. muridarum challenged IFN-γ$^-$ mice. One group of naïve IFN-γ$^{-/-}$ mice that was challenged with the bacterium, but did not receive cellular transfer, served as baseline control for effects of chlamydial infection. The only source of IFN-γ production in the recipient animals was the adoptively transferred IFN-γ$^{+/+}$ CD4$^+$ T cells. Recipient IFN-γ$^{-/-}$ mice that received CPAF-specific CD4$^+$ T cells from IFN-γ$^{+/+}$ mice, but not IFN-γ$^{+/+}$ mice, resolved the infection by day 18 after challenge. The majority of the recipient IFN-γ$^{-/-}$ mice that received IFN-γ$^{+/+}$ mock (PBS) CD4$^+$ T cells (83%) or IFN-γ$^{-/-}$ CPAF-specific CD4$^+$ T cells (67%) were still shedding Chlamydia as late as day 30 after challenge. The development of hydrosalpinx in these groups of animals was further examined. All (100%) of the IFN-γ$^{-/-}$ mice that received IFN-γ$^{-/-}$ CPAF-specific CD4$^+$ T cells, or those that did not receive any cells, developed bilateral hydrosalpinx at day 80 after chlamydial challenge. In contrast, IFN-γ$^{-/-}$ mice that received IFN-γ CPAF-specific CD4$^+$ T cells were highly protected with hydrosalpinx evident in significantly fewer animals (33% bilateral). These results demonstrate that CPAF-specific CD4$^+$ T cells produce amounts of IFN-γ sufficient to mediate the enhanced resolution of murine genital chlamydial infection and reduction of oviduct pathology in an otherwise IFN-γ deficient environment.

These results, for the first time, have clearly defined the sufficiency of Ag-specific CD4$^+$ T cells secreting IFN-γ to mediate anti-chlamydial immunity; an observation that has significant relevance to vaccine development. Given that an IFN-γ response can be induced by various adaptive immune cells, predominantly CD4$^+$ T cells and CD8$^+$ T cells, the targeting of the candidate Ag to MHC class I or class II pathway may be crucial in eliciting a dominant CD8$^+$ T cell or CD4+ T cell response, respectively. Soluble Ags (e.g. recombinant CPAF), are taken up by endosomes and processed primarily via the MHC class II pathway. However, Ags delivered into the extracellular space also may get processed and cross-presented via the MHC I pathway to CD8+ T cells (47, 48). To address this issue, the present study specifically examined whether absence of the MHC I pathway altogether, but with an intact MHC II pathway, would affect the effects of rCPAF+CpG vaccination. Groups of mice deficient in β2 microglobulin (β2m$^{-/-}$ mice) and therefore in MHC class I loading complex, and the corresponding wild type C57BL/6 mice (β2m$^{+/+}$ mice) were vaccinated with three doses of rCPAF+CpG, rested for a month and challenged i.vag. with $10^5$ IFU of C. muridarum. The complete absence of MHC I complexes would exclude the priming or effector functions of CD8+ T cells in these experiments. rCPAF+CpG vaccinated β2 m$^{-/-}$ mice completely resolved the infection by day 18 post-challenge, which was comparable to resolution in vaccinated wild type β2 m$^{+/+}$ mice. Mock (PBS) vaccinated β2m$^{-/-}$ mice and β2 m$^{-/-}$ mice displayed comparable resolution kinetics, with chlamydial clearance occurring by day 30 after challenge in each group. On day 80 after challenge, significant reduction in hydrosalpinx was observed in rCPAF+CpG vaccinated P2m$^{-/-}$ mice (20% bilateral, 20% unilateral) and β2m mice (20% bilateral), when compared to PBS (mock) vaccinated β2m mice (80% bilateral, 20% unilateral) and β2m mice (100% bilateral), respectively (FIG. 3). This suggests further support that presentation of rCPAF via the MHC II pathway to CD4+ T cells is sufficient to induce protective anti-chlamydial response.

Collectively, these studies have provided compelling evidence to suggest that Ag-specific CD4+ T cells (a) induce early chlamydial clearance and reduce oviduct pathology via production of IFN-γ and (b) produce sufficient amounts of IFN-γ to induce anti-chlamydial immunity, in an otherwise IFN-γ deficient environment. Therefore, recombinant soluble vaccine antigens may be targeted to the MHC II pathway to elicit optimal IFN-γ production from Ag-specific CD4+ T cells for effective immunity against genital chlamydial infections.

Example 7 rPCAF+CpG vaccination induced preservation of fertility after secondary genital chlamydial challenge. Because repeated chlamydial infections have been known to induce infertility, we examined whether the rCPAF+CpG vaccination regimen leads to preservation of fertility after secondary genital chlamydial challenge.

Groups (6 mice per group) of 4-6 week-old female BALB/c mice were vaccinated i.n. or i.p. with rCPAF (15 µg)+CpG (10 µg) on day 0, and booster immunizations were given on days 14 and 28. One group of mice was mock vaccinated with PBS alone. Mice were rested for one month after final booster immunization and challenged i.vag. with $5 \times 10^4$ IFU of C. muridarum. Vaccinated mice were treated with 2.5 mg s.c. depo-progesterone 10 and 3 days before challenge. The vaginal bacterial shedding was monitored every third day and the resolution of infection by day 30 was confirmed. Two weeks after resolution of the primary infection, mice were rechallenged i.vag. with $5 \times 10^4$ IFU of C. muridarum. On day 80 after rechallenge, mice were evaluated for fertility. A group (15 mice per group) of age-matched mice that did not receive any immunization, and was not challenged, was used as naïve control for the fertility studies. The female mice were mated with proven male breeder mice (2 females and 1 male per cage) and weight gain in female mice was monitored over 18 days. The females that gained significant weight (>20% of original body weight) were euthanized and the number of implantations per uterine horn was recorded. The female mice that did not gain weight were rested for 10 days and mated for a second time with the male breeders for an additional 18 days. At the end of the second mating cycle, all female mice were euthanized and the number of implantations in each uterine horn was recorded. As shown in Table 5, 80% (12 of 15) of naïve mice became pregnant, compared to 33% (2 of 6) of mock-vaccinated C. muridarum challenged mice, indicating the significant reduction of fertility after genital chlamydial infection. In comparison, 67% (4 of 6) each of mice vaccinated i.n. or i.p. with rCPAF+CpG became pregnant, indicating a significant preservation of fertility. Moreover, the total number of implantations (mean±SD) in pregnant rCPAF+CpG vaccinated mice (i.n.—7±2.1 and i.p.—9.25±1.9) was significantly (p<0.05, student's t test) greater than mock (PBS—4±1.1), and comparable to the age-matched naïve mice (9.4±1.9). Collectively, these results provide evidence that rCPAF+CpG vaccination induces protective immunity against the development of infertility after repeated genital chlamydial challenges.

Example 8

Cellular Response to rCPAF Fragments After Vaccination in HLA-DR4 tg Mice Using ELISPOT A group of HLA-DR4 tg mice (3 mice per group) were immunized subcutaneously (s.c.) with full-length rCPAF and the draining lymph nodes were removed after 14 days. Single cell suspensions were made and the lymphocytes ($5 \times 10^5$ cells/well) were stimulated in vitro with the full length rCPAF (1 µg), or the indicated fragments of rCPAF (1-200, 136-609, 242-609, 284-609, 387-609; 1 µg each), or an unrelated antigen (gp39; 1 µg), or media alone and the numbers of cells secreting IFN-γ or IL-5 were examined using cytokine ELISPOT. The results are expressed as mean±SE of the number of cytokine spots per $5 \times 10^5$ lymphocytes. As shown in FIG. 4, cells recalled with full length rCPAF (149±6 spots), or the rCPAF fragments individually (1-200: 216±46 spots; 136-609: 194±27 spots; 242-609: 194±26 spots; 284-609: 66±17 spots; 387-609: 234±16 spots), but not gp39 or media alone, exhibited numerous Ag-specific IFN-γ spots, indicating CPAF-specific IFN-γ production. In addition, there were no detectable IL-5 spots in any culture wells. These results indicate that (a) human HLA-DR4 restricted CPAF determinants are capable of inducing robust Th1 biased cellular responses, and (b) immunogenic epitopes are present throughout the length of the rCPAF molecule, and may be used for targeted subunit vaccination.

The foregoing is illustrative of the present invention, and is not to be construed as limiting thereof. The invention is defined by the following claims, with equivalents of the claims to be included therein. All publications, patent applications, patents, patent publications, sequences identified by GenBank® database and/or SNP accession numbers, and other references cited herein are incorporated by reference in their entireties for the teachings relevant to the sentence and/or paragraph in which the reference is presented.

REFERENCES

1. Arulanandam, B. P., Lynch, J. M., Briles, D. E., Hollingshead, S., and Metzger, D. W. (2001). Intranasal vaccination with pneumococcal surface protein A and interleukin-12 augments antibody-mediated opsonization and protective 1. immunity against *Streptococcus pneumoniae* infection. *Infect. Immun.* 69, 6718-6724.
2. Brunham, R. C. and Rey-Ladino, J. (2005). Immunology of *Chlamydia* infection: implications for a *Chlamydia trachomatis* vaccine. *Nat. Rev. Immunol.* 5, 149-161.
3. Dong, F., Su, H., Huang, Y., Zhong, Y., and Zhong, G. (2004). Cleavage of host keratin 8 by a *Chlamydia*-secreted protease. *Infect. Immun.* 72, 3863-3868.
4. Huber, V. C., Arulanandam, B. P., Arnaboldi, P. M., Elmore, M. K., Sheehan, C. E., Kallakury, B. V., and Metzger, D. W. (2003). Delivery of IL-12 intranasally leads to reduced IL-12-mediated toxicity. *Int. Immunopharmacol.* 3, 801-809.
5. Ito, K., Bian, H. J., Molina, M., Han, J., Magram, J., Saar, E., Belunis, C., Bolin, D. R., Arceo, R., Campbell, R., Falcioni, F., Vidovic, D., Hammer, J., and Nagy, Z. A. (1996). HLA-DR4-IE chimeric class II transgenic, murine class 11-deficient mice are susceptible to experimental allergic encephalomyelitis. *J. Exp. Med.* 183, 2635-2644.
6. Madsen, L., Labrecque, N., Engberg, J., Dierich, A., Svejgaard, A., Benoist, C., Mathis, D., and Fugger, L. (1999). Mice lacking all conventional MHC class II genes. *Proc. Natl. Acad. Sci. U.S.A* 96, 10338-10343.
7. Morrison, R. P. and Caldwell, H. D. (2002). Immunity to murine chlamydial genital infection. *Infect. Immun.* 70, 2741-2751.
8. Morrison, S. G., Su, H., Caldwell, H. D., and Morrison, R. P. (2000). Immunity to murine *Chlamydia trachomatis* genital tract reinfection involves B cells and CD4(+) T cells but not CD8(+) T cells. *Infect. Immun.* 68, 6979-6987.
9. Murthy, A. K., Sharma, J., Coalson, J. J., Zhong, G., and Arulanandam, B. P. (2004). *Chlamydia trachomatis* pulmonary infection induces greater inflammatory pathology in immunoglobulin A deficient mice. *Cell Immunol.* 230, 56-64.
10. Nelson, D. E., Virok, D. P., Wood, H., Roshick, C., Johnson, R. M., Whitmire, W. M., Crane, D. D., Steele-Mortimer, O., Kari, L., McClarty, G., and Caldwell, H. D. (2005). Chlamydial IFN-gamma immune evasion is linked to host infection tropism. *Proc. Natl. Acad. Sci. U.S.A* 102, 10658-10663.
11. Sharma, J., Bosnic, A. M., Piper, J. M., and Zhong, G. (2004). Human antibody responses to a *Chlamydia*-secreted protease factor. *Infect. Immun.* 72, 7164-7171.
12. Sharma, J., Dong, F., Pirbhai, M., and Zhong, G. (2005). Inhibition of proteolytic activity of a chlamydial proteasome/protease-like activity factor by antibodies from humans infected with *Chlamydia trachomatis. Infect. Immun.* 73, 4414-4419.
13. Zhong, G., Fan, P., Ji, H., Dong, F., and Huang, Y. (2001). Identification of a chlamydial protease-like activity factor responsible for the degradation of host transcription factors. *J. Exp. Med.* 193, 935-942.
14. Zhong, G. M., Reid, R. E., and Brunham, R. C. (1990). Mapping antigenic sites on the major outer membrane protein of *Chlamydia trachomatis* with synthetic peptides. *Infect. Immun.* 58, 1450-1455.
15. Bienenstock, J. (1970). The significance of secretory immunoglobulins. *Can. Med. Assoc. J.* 103, 39-43.
16. Chevailler, A. and Renier, G. (1989). [Serum and secretory immunoglobulins A. Molecular and cellular aspects of their biosynthesis and function]. *Ann. Med. Interne (Paris)* 140, 299-313.
17. Cotter, T. W., Ramsey, K. H., Miranpuri, G. S., Poulsen, C. E., and Byrne, G. I. (1997). Dissemination of *Chlamydia trachomatis* chronic genital tract infection in gamma interferon gene knockout mice. *Infect. Immun.* 65, 2145-2152.
18. Dong, F., Su, H., Huang, Y., Zhong, Y., and Zhong, G. (2004). Cleavage of host keratin 8 by a *Chlamydia*-secreted protease. *Infect. Immun.* 72, 3863-3868.
19. Ito, J. I. and Lyons, J. M. (1999). Role of gamma interferon in controlling murine chlamydial genital tract infection. *Infect. Immun.* 67, 5518-5521.
20. Johansson, M., Schon, K., Ward, M., and Lycke, N. (1997). Genital tract infection with *Chlamydia trachomatis* fails to induce protective immunity in gamma interferon receptor-deficient mice despite a strong local immunoglobulin A response. *Infect. Immun.* 65, 1032-1044.
21. Pal, S., Peterson, E. M., and de la Maza, L. M. (2005). Vaccination with the *Chlamydia trachomatis* major outer membrane protein can elicit an immune response as protective as that resulting from inoculation with live bacteria. *Infect. Immun.* 73, 8153-8160.
22. Perry, L. L., Feilzer, K., and Caldwell, H. D. (1997). Immunity to *Chlamydia trachomatis* is mediated by T helper 1 cells through IFN-gamma-dependent and -independent pathways. *J. Immunol.* 158, 3344-3352.
23. Rank, R. G. (1994). Animal models for urogenital infections. *Methods Enzymol.* 235, 83-93.
24. Rank, R. G., Ramsey, K. H., Pack, E. A., and Williams, D. M. (1992). Effect of gamma interferon on resolution of murine chlamydial genital infection. *Infect. Immun.* 60, 4427-4429.
25. Sharma, J., Zhong, Y., Dong, F., Piper, J. M., Wang, G., and Zhong, G. (2006). Profiling of human antibody responses to *Chlamydia trachomatis* urogenital tract infection using microplates arrayed with 156 chlamydial fusion proteins. *Infect. Immun.* 74, 1490-1499.
26. Stefani, D. V. (1973). [Secretory immunoglobulins and the problem of local immunity (literature review)]. *Zh Mikrobiol. Epidemiol. Immunobiol.* 50, 7-11.
27. Thomasi, T. B., Jr. (1972). Secretory immunoglobulins. *N. Engl. J. Med.* 287, 500-506.
28. Tomasi, T. B., Jr. and Bienenstock, J. (1968). Secretory immunoglobulins. *Adv. Immunol.* 9, 1-96.
29. Zhong, G., Fan, T., and Liu, L. (1999). *Chlamydia* inhibits interferon gamma-inducible major histocompatibility complex class II expression by degradation of upstream stimulatory factor 1. *J. Exp. Med.* 189, 1931-1938.
30. Zhong, G., Liu, L., Fan, T., Fan, P., and Ji, H. (2000). Degradation of transcription factor RFX5 during the inhibition of both constitutive and interferon gamma-inducible major histocompatibility complex class I expression in *Chlamydia*-infected cells. *J. Exp. Med.* 191, 1525-1534.
31. Dong F, Pirbhai M, Zhong Y, Zhong G. (2004). Cleavage-dependent activation of a *Chlamydia*-secreted protease. *Mol. Microbiol.* 52, 1487-94.
32. Wongratanacheewin S, Kespichayawattana W, Intachote P, et al. (2004). Immunostimulatory CpG oligodeoxynucleotide confers protection in a murine model of infection with *Burkholderia pseudomallei.* Infect. Immun. 72, 4494-502.
33. Gallichan W S, Woolstencroft R N, Guarasci T, McCluskie M J, Davis H L, Rosenthal K L. (2001). Intranasal immunization with CpG oligodeoxynucleotides as an adjuvant dramatically increases IgA and protection against herpes simplex virus-2 in the genital tract. J. Immunol. 166, 3451-7.
34. Arulanandam, B. P. and D. W. Metzger. (1999). Modulation of mucosal and systemic immunity by intranasal interleukin 12 delivery. *Vaccine* 17, 252-260.
35. Arulanandam, B. P., M. O'Toole, and D. W. Metzger. (1999). Intranasal interleukin-12 is a powerful adjuvant for protective mucosal immunity. *J. Infect. Dis.* 180, 940-949.

36. Cain, T. K. and R. G. Rank. (1995). Local Th1-like responses are induced by intravaginal infection of mice with the mouse pneumonitis biovar of Chlamydia trachomatis. Infect. Immun. 63, 1784-1789.
37. Melkus, M. W., J. D. Estes, A. Padgett-Thomas, J. Gatlin, P. W. Denton, F. A. Othieno, A. K. Wege, A. T. Haase, and J. V. Garcia. (2006). Humanized mice mount specific adaptive and innate immune responses to EBV and TSST-1. Nat. Med. 12, 1316-1322.
38. Murphey, C., A. K. Murthy, P. A. Meier, G. M. Neal, G. Zhong, and B. P. Arulanandam. (2006). The protective efficacy of chlamydial protease-like activity factor vaccination is dependent upon CD4+ T cells. Cell Immunol. 242, 10-117.
39. Murthy, A. K., Y. Cong, C. Murphey, M. N. Guentzel, T. G. Forsthuber, G. Zhong, and B. P. Arulanandam. (2006). Chlamydial protease-like activity factor induces protective immunity against genital chlamydial infection in transgenic mice that express the human HLA-DR4 allele. Infect. Immun. 74, 6722-6729.
40. Perry, L. L., K. Feilzer, J. L. Portis, and H. D. Caldwell. (1998). Distinct homing pathways direct T lymphocytes to the genital and intestinal mucosae in Chlamydia-infected mice. J. Immunol. 160, 2905-2914.
41. Perry, L. L., H. Su, K. Feilzer, R. Messer, S. Hughes, W. Whitmire, and H. D. Caldwell. (1999). Differential sensitivity of distinct Chlamydia trachomatis isolates to IFN-gamma-mediated inhibition. J. Immunol. 162, 3541-3548.
42. Sun, Z., P. W. Denton, J. D. Estes, F. A. Othieno, B. L. Wei, A. K. Wege, M. W. Melkus, A. Padgett-Thomas, M. Zupancic, A. T. Haase, and J. V. Garcia. (2007). Intrarectal transmission, systemic infection, and CD4+ T cell depletion in humanized mice infected with HIV-1. J. Exp. Med. 204, 705-714.
43. Murthy A K, Chambers J P, Meier P A, Zhong G, Arulanandam B P. (2007). Intranasal vaccination with a secreted chlamydial protein enhances resolution of genital Chlamydia muridarum infection, protects against oviduct pathology, and is highly dependent upon endogenous gamma interferon production. Infect Immun 75, 666-76.
44. Cong Y, Jupelli M, Guentzel M N, Zhong G, Murthy A K, Arulanandam B P. (2007). Intranasal immunization with chlamydial protease-like activity factor and CpG deoxynucleotides enhances protective immunity against genital Chlamydia muridarum infection. Vaccine 25, 3773-80.
45. Asquith B, Debacq C, Florins A, et al. (2006) Quantifying lymphocyte kinetics in vivo using carboxyfluorescein diacetate succinimidyl ester (CFSE). Proc Biol Sci 273, 1165-71.
46. Lyons A B. (2000m September. 21). Analyzing cell division in vivo and in vitro using flow cytometric measurement of CFSE dye dilution. J Immunol Methods 243(1-2): 147-54.
47. Heath W R, Belz G T, Behrens G M, et al. (2004). Cross-presentation, dendritic cell subsets, and the generation of immunity to cellular antigens. Immunol Rev 199, 9-26.
48. Belz G T, Carbone F R, Heath W R. (2002). Cross-presentation of antigens by dendritic cells. Crit Rev Immunol; 22(5-6):439-48.
49. Dong, F., Pirhai, M., Zhong, Y., and Zhong, G. (2004). Cleavage-dependent activation of a Chlamydia-secreted protease. Mol. Microbiol. 52, 1487-1494.
50. Landers, D. V., Erlich, K., Sung, M., and Schachter, J. (1991). Role of L3T4-bearing T-cell populations in experimental murine chlamydial salpingitis. Infect. Immun. 59, 3774-3777.
51. Rank, R. G., Soderberg, L. S., and Barron, A. L. (1985). Chronic chlamydial genital infection in congenitally athymic nude mice. Infect. Immun. 48, 847-849.

TABLE 1

Intranasal rCPAF + IL-12 vaccination induces robust cell-mediated immune responses.

| Immunization | Cellular Recall IFN-gamma (pg/ml) Production In vitro stimulation | | | |
|---|---|---|---|---|
| | rCPAF | rMOMP | rIncA | Media |
| PBS (mock) | <32 | <32 | <32 | <32 |
| IL-12 | <32 | <32 | <32 | <32 |
| rCPAF + IL-12 | 1525 ± 172 | 87 ± 34 | 66 ± 24 | <32 |
| rMOMP + IL-12 | 64 ± 31 | 228 ± 72 | 96 ± 45 | <32 |
| rIncA + IL-12 | 58 ± 26 | 90 ± 32 | 972 ± 128 | <32 |
| C. muridarum | 295 ± 95 | 155 ± 45 | 270 ± 80 | <32 |
| HEL + IL-12 | 65 ± 30 | 52 ± 21 | 35 ± 13 | <32 |

Animals (3 mice/group) were immunized i.n. with rCPAF + IL-12, rMOMP + IL-12, rIncA + IL-12, C. muridarum ($10^5$ IFU), the unrelated antigen HEL + IL-12, IL-12 alone, or PBS (mock) alone. On day 14, animals were euthanized, splenic CD4+ T cells were purified and tested for antigen-specific IFN-γ production by ELISA. Results are representative of two independent experiments.

TABLE 2

Intranasal rCPAF + IL-12 vaccination induces robust humoral immune responses.

| Immunization | Total Ab | IgG1 | IgG2a | IgG2b |
|---|---|---|---|---|
| A | | | | |
| | Serum Anti-CPAF Antibody | | | |
| PBS (mock) | <100 | <100 | <100 | <100 |
| IL-12 | <100 | <100 | <100 | <100 |
| rCPAF + IL-12 | 6180 ± 452 | 3602 ± 888 | 5261 ± 319 | 1928 ± 655 |
| rMOMP + IL-12 | <100 | <100 | <100 | <100 |
| rIncA + IL-12 | <100 | <100 | <100 | <100 |
| rCPAF + rMOMP + IL-12 | 4140 ± 348 | 3085 ± 838 | 5462 ± 585 | 1462 ± 280 |
| rCPAF + rIncA + IL-12 | 5015 ± 957 | 3914 ± 921 | 5410 ± 317 | 2560 ± 541 |
| rCPAF + rMOMP + rIncA + IL-12 | 4323 ± 635 | 3461 ± 610 | 4898 ± 736 | 1901 ± 495 |
| HEL + IL-12 | <100 | <100 | <100 | <100 |
| B | | | | |

TABLE 2-continued

Intranasal rCPAF + IL-12 vaccination induces robust humoral immune responses.

| Immunization | Total Ab | IgG1 | IgG2a | IgG2b |
|---|---|---|---|---|
| | Serum Anti-MOMP Antibody | | | |
| PBS (mock) | <100 | <100 | <100 | <100 |
| IL-12 | <100 | <100 | <100 | <100 |
| rCPAF + IL-12 | <100 | <100 | <100 | <100 |
| rMOMP + IL-12 | 3802 ± 160 | 3740 ± 764 | 1915 ± 185 | 2775 ± 648 |
| rIncA + IL-12 | <100 | <100 | <100 | <100 |
| rCPAF + rMOMP + IL-12 | 4693 ± 172 | 3774 ± 211 | 2013 ± 243 | 2706 ± 332 |
| rCPAF + IncA + IL-12 | <100 | <100 | <100 | <100 |
| rCPAF + rMOMP + rIncA + IL-12 | 4697 ± 138 | 3873 ± 341 | 2176 ± 180 | 3059 ± 461 |
| HEL + IL-12 | <100 | <100 | <100 | <100 |

C

| Immunization | Total Ab | IgG1 | IgG2a | IgG2b |
|---|---|---|---|---|
| | Serum Anti-IncA Antibody | | | |
| PBS (mock) | <100 | <100 | <100 | <100 |
| IL-12 | <100 | <100 | <100 | <100 |
| rCPAF + IL-12 | <100 | <100 | <100 | <100 |
| rMOMP + IL-12 | <100 | <100 | <100 | <100 |
| rIncA + IL-12 | 3647 ± 115 | 1411 ± 351 | 3380 ± 286 | 1387 ± 324 |
| rCPAF + rMOMP + IL-12 | <100 | <100 | <100 | <100 |
| rCPAF + rIncA + IL-12 | 3155 ± 198 | 1776 ± 373 | 3297 ± 201 | 1353 ± 166 |
| rCPAF + rMOMP + rIncA + IL-12 | 3877 ± 78 | 1534 ± 152 | 2921 ± 86 | 1529 ± 230 |
| HEL + IL-12 | <100 | <100 | <100 | <100 |

Animals (6 mice/group) were immunized i.n. with rCPAF + IL-12, rMOMP + IL-12, rIncA + IL-12, *C. muridarum* ($10^5$ IFU), HEL + IL-12, IL-12, or PBS (mock). Animals were bled ten days after final booster immunization and sera were analyzed for (A) anti-CPAF antibody, (B) anti-MOMP antibody, (C) anti-IncA antibody levels by ELISA using microtiter plates coated with corresponding antigens. Results are expressed as means ± SD of reciprocal serum dilutions corresponding to 50% maximal binding. Results are representative of two independent experiments.

TABLE 3

Percentage of immunized animals shedding Chlamydia after genital challenge.

| | % Mice Shedding *Chlamydia* from the Vagina (n = 6) | | | | | | | | | |
|---|---|---|---|---|---|---|---|---|---|---|
| | Day after I. Vag. Challenge | | | | | | | | | |
| Immunization | 3 | 6 | 9 | 12 | 15 | 18 | 21 | 24 | 27 | 30 |
| PBS (mock) | 100 | 100 | 100 | 100 | 100 | 100 | 50 | 50 | 33 | 0 |
| rCPAF + IL-12 | 100 | 100 | 100 | 67 | 33 | 0 | 0 | 0 | 0 | 0 |
| rMOMP + IL-12 | 100 | 100 | 100 | 100 | 100 | 67 | 50 | 17 | 0 | 0 |
| rIncA + IL-12 | 100 | 100 | 100 | 100 | 83 | 50 | 33 | 17 | 0 | 0 |
| rCPAF + rMOMP + IL-12 | 100 | 100 | 100 | 67 | 50 | 0 | 0 | 0 | 0 | 0 |
| rCPAF + rIncA + IL-12 | 100 | 100 | 100 | 50 | 17 | 0 | 0 | 0 | 0 | 0 |
| rCPAF + rMOMP + rIncA + IL-12 | 100 | 100 | 100 | 83 | 67 | 0 | 0 | 0 | 0 | 0 |
| HEL + IL-12 | 100 | 100 | 100 | 100 | 100 | 100 | 67 | 50 | 33 | 0 |

Animals (6 mice/group) were immunized with three doses of rCPAF + IL-12, rMOMP + IL-12, rIncA + IL-12, rCPAF + rMOMP + IL-12, rCPAF + rIncA + IL-12, rCPAF + rMOMP + rIncA + IL-12, HEL + IL-12, or PBS (mock). One month after the final booster vaccination, mice were challenged i. vag. with $10^5$ IFU of *C. muridarum*. Chlamydial shedding was measured at the indicated days following challenge. Significant differences were detected in time required for resolution of infection between all immunization regimens containing rCPAF versus others (P = 0.0002, Kaplan-Meier test). Results are representative of two independent experiments.

TABLE 4 rCPAF + IL-12 immunization reduces the development of oviduct pathology.

A

| | % Mice Developing Hydrosalpinx (n = 6) Day 80 after C. muridarum challenge | |
|---|---|---|
| Immunization | Bilateral | Unilateral |
| PBS (mock) | 83 | 0 |
| rCPAF + IL-12 | 0 | 33 |
| rMOMP + IL-12 | 33 | 33 |
| rIncA + IL-12 | 50 | 17 |
| rCPAF + rMOMP + IL-12 | 0 | 17 |
| rCPAF + rIncA + IL-12 | 0 | 0 |
| rCPAF + rMOMP + rIncA + IL-12 | 17 | 17 |
| HEL + IL-12 | 67 | 17 |

B

| Immunization | Oviduct Dilatation Score (n = 6) Day 80 after C. muridarum Challenge |
|---|---|
| PBS (mock) | 2.41 ± 0.23 |
| rCPAF + IL-12 | 0.66 ± 0.21 |
| rMOMP + IL-12 | 1.18 ± 0.23 |
| rIncA + IL-12 | 1.25 ± 0.21 |
| rCPAF + rMOMP + IL-12 | 0.5 ± 0.13 |
| rCPAF + rIncA + IL-12 | 0.5 ± 0.12 |
| rCPAF + rMOMP + rIncA + IL-12 | 0.67 ± 0.30 |
| HEL + IL-12 | 2.16 ± 0.33 |

C

| | Cellular Infiltration Score (n = 6) Day 80 after C. muridarum challenge | | |
|---|---|---|---|
| Immunization | PMNs | Mono | Plasma * |
| PBS (mock) | 1.28 ± 0.22 | 27 ± 0.26 | 1.58 ± 0.20 |
| rCPAF + Il-12 | 0.66 ± 0.17 | 0.79 ± 0.24 | 0.45 ± 0.07 |
| rMOMP + Il-12 | 1.12 ± 0.22 | 1.62 ± 0.49 | 1.00 ± 0.20 |
| rIncA + IL-12 | 0.79 ± 0.15 | 1.5 ± 0.34 | 0.70 ± 0.10 |
| rCPAF + rMOMP + IL-12 | 0.75 ± 0.25 | 0.83 ± 0.15 | 0.41 ± 0.13 |
| rCPAF + rIncA + IL-12 | 0.62 ± 0.14 | 0.65 ± 0.10 | 0.45 ± 0.11 |
| rCPAF + rMOMP + rIncA + IL-12 | 0.75 ± 0.11 | 0.75 ± 0.17 | 0.55 ± 0.12 |
| HEL + IL-12 | 1.41 ± 0.22 | 2.66 ± 0.27 | 1.75 ± 0.18 |

Animals (6 mice/group) were immunized with three doses of rCPAF + IL-12, rMOMP + IL-12, rIncA + IL-12, rCPAF + rMOMP + IL-12, rCPAF + rIncA + IL-12, rCPAF + rMOMP + rIncA + IL-12, HEL + IL-12, or PBS (mock). At day 80 following i. vag. challenge with $10^5$ IFU of C. muridarum, animals were euthanized and tissues collected for further analysis. (A) Gross pathology: Bilateral and Unilateral hydrosalpinx. (B) Quantitative histopathological scoring of oviduct dilatation. (C) Cellular infiltration into the genital tracts following chlamydial challenge. Means ± SD of histopathology and cellular infiltration scores are shown.
* Significant differences were detected in time required for resolution of infection between all immunization regimens containing rCPAF versus others (P < 0.05, Mann-Whitney Rank-Sum test). Results are representative of two independent experiments.

TABLE 5

| | C. mur prim/sec challenge | Pregnant mice (pregnant/total) | Mean ± SD implantations (pregnant mice only) | | |
|---|---|---|---|---|---|
| Vaccination | | | R | L | Total |
| None | None | 80% (12/15) | 4.58 ± 1.3 | 4.83 ± 1.2 | 9.4 ± 1.9 |
| Mock (PBS) | Yes | 33% (2/6) | 2.5 ± 0.7 | 1.5 ± 0.7 | 4 ± 1.1 |
| CPAF + CpG i.n. | Yes | 67% (4/6) | 3 ± 1.8 | 4 ± 1.1 | 7 ± 2.1 |
| CPAF + CpG i.p. | Yes | 67% (4/6) | 4.5 ± 1.3 | 4.75 ± 0.9 | 9.25 ± 1.9 |

Effect of rCPAF + CpG vaccination on preservation of fertility after secondary genital chlamydial challenge. C. mur: Chlamydia muridarum; pri/sec: primary and secondary challenge; R: right uterine horn; L: left uterine horn.

TABLE 6

Percentage of immunized animals shedding Chlamydia after genital challenge[a]

| | % of mice shedding chlamydia from the vagina (n = 10) on the following days after i. vag. challenge: | | | | | | | |
|---|---|---|---|---|---|---|---|---|
| Immunization | 4 | 8 | 12 | 15 | 18 | 21 | 24 | 30 |
| Mock | 100 | 100 | 100 | 100 | 80 | 70 | 60 | 30 |
| IL-12 | 100 | 100 | 90 | 90 | 80 | 70 | 70 | 30 |
| rCPAF | 100 | 100 | 90 | 90 | 60 | 60 | 30 | 0 |
| rCPAF + IL-12 | 100 | 100 | 70 | 20 | 0 | 0 | 0 | 0 |

[a] Animals (10 mice/group) were treated with three doses of rCPAF + IL-12, rCPAF, IL-12, or PBS (Mock). One month following the final vaccination, mice were challenged i. vag. with $5 \times 10^4$ IFU of C. muridarum. On the days following challenge indicated, chlamydial shedding was measured. There were significant differences in the time required for resolution of infection between rCPAF + IL-12-immunized mice and all other experimental groups (P = 0.0002, as determined by the Kaplan-Meier test). The results are representative of the results of three independent experiments.

TABLE 7 rCPAF + IL-12 immunization reduces the development of hydrosalpinx[a]

| Immunization | 12 | | 14 | | 18 | | 30 | | 50 | | 80 | |
|---|---|---|---|---|---|---|---|---|---|---|---|---|
| | B | U | B | U | B | U | B | U | B | U | B | U |
| Mock | 0 | 0 | 0 | 0 | 0 | 0 | 0 | 12.5 | 62.5 | 25 | 62.5 | 12.5 |
| rCPAF + IL-12 | 0 | 0 | 0 | 0 | 0 | 0 | 0 | 0 | 0 | 0 | 0 | 0 |

% of mice developing hydrosalpinx (n = 8) on the following days after C. muridarum challenge:

[a] Animals (eight mice/group) were immunized with three doses of rCPAF + IL-12 or PBS (Mock), rested for 1 month, and subsequently challenged i. vag. with 5 × 10^4 IFU of C. muridarum. At different times following challenge, animals (eight mice/group/time) were euthanized, and tissues were collected and used for further analysis. The results are representative of the results of two independent experiments. B, bilateral; U, unilateral.

TABLE 8

Percentage of immunized IFN-γ−/− animals shedding Chlamydia after genital challenge[a]

% of mice shedding chlamydia from the vagina (n = 6) on the following days after i. vag. challenge:

| Immunization | Mice | 3 | 6 | 9 | 12 | 15 | 18 | 21 | 24 | 30 | 50 |
|---|---|---|---|---|---|---|---|---|---|---|---|
| Mock | IFN-γ+/+ | 100 | 100 | 100 | 100 | 100 | 83.3 | 83.3 | 66.7 | 16.7 | 0 |
| | IFN-γ−/− | 100 | 100 | 100 | 100 | 100 | 100 | 100 | 100 | 100 | 66.7 |
| rCPAF + IL-12 | IFN-γ+/+ | 100 | 100 | 66.7 | 50 | 16.7 | 0 | 0 | 0 | 0 | 0 |
| | IFN-γ−/− | 100 | 100 | 100 | 100 | 83.3 | 83.3 | 83.3 | 66.7 | 66.7 | 50 |

[a] Groups of IFN-γ+/+ and IFN-γ−/− mice (six mice/group) were immunized with three doses of rCPAF + IL-12 or PBS (Mock), rested for 1 month, and challenged i. vag. with 5 × 10^4 IFU of C. muridarum. Chlamydial shedding was measured on the days following challenge indicated. There were significant differences in the time to resolution of infection between rCPAF + IL-12-immunized IFN-γ+/+ mice and all other experimental groups (P < 0.0001, as determined by the Kaplan-Meier's test). The results are representative of the results of two independent experiments.

TABLE 9

IFN-γ is required for prevention of hydrosalpinx development in Chlamydia-challenged rCPAF + IL-12-immunized animals[a]

% of mice developing hydrosalpinx (n = 6) on day 80 after C. muridarum challenge

| Immunization | Mice | Bilateral | Unilateral |
|---|---|---|---|
| Mock | IFN-γ+/+ | 66.7 | 16.67 |
| | IFN-γ−/− | 100 | 0 |
| rCPAF + IL-12 | IFN-γ+/+ | 0 | 0 |
| | IFN-γ−/− | 100 | 0 |

[a] Animals (eight mice/group) were immunized with three doses of rCPAF + IL-12 or PBS (Mock), rested for 1 month, and subsequently challenged i. vag. with 5 × 10^4 IFU of C. muridarum. On day 80 after challenge, animals (eight mice/group) were euthanized, and tissues were collected and used for analyses. The results are representative of the results of two independent experiments.

What is claimed is:

1. A method of reducing the likelihood of infertility due to *Chlamydia* infection in a subject, comprising administering to the subject a composition comprising an effective amount of a chlamydial protease-like activity factor (CPAF) protein or an immunogenic fragment thereof, thereby treating *Chlamydia* infection, which thereby reduces the likelihood of infertility caused by said *Chlamydia* infection.

2. A method of reducing the likelihood of infertility due to *Chlamydia* infection in a subject, comprising administering to the subject a composition comprising:

a) an effective amount of a chlamydial protease-like activity factor (CPAF) protein or an immunogenic fragment thereof, and b) an effective amount of a different chlamydial protein or immunogenic fragment thereof, thereby treating *Chlamydia* infection, which thereby reduces the likelihood of infertility caused by said *Chlamydia* infection.

3. The method of claim 1, further comprising administering an adjuvant to the subject.

4. The method of claim 2, further comprising administering an adjuvant to the subject.

5. The method of claim 3, wherein the adjuvant is selected from the group consisting of: IL-12, CpG oligodeoxynucleotides, alum, Montanide ISA 720 and any combination thereof.

6. The method of claim 4, wherein the adjuvant is selected from the group consisting of: IL-12, CpG oligodeoxynucleotides, alum, Montanide ISA 720 and any combination thereof.

* * * * *

UNITED STATES PATENT AND TRADEMARK OFFICE
CERTIFICATE OF CORRECTION

PATENT NO. : 7,892,567 B2
APPLICATION NO. : 12/243769
DATED : February 22, 2011
INVENTOR(S) : Arulanandam et al.

It is certified that error appears in the above-identified patent and that said Letters Patent is hereby corrected as shown below:

Column 50, Line 43: Please correct "IFN-$\gamma^{+/+}$" to read -- IFN-$\gamma^{-/-}$ --

Column 51, Line 20: Please correct "β2 m$^{-/-}$" to read -- β2 m$^{+/+}$ --
Line 24: Please correct "P2m$^{-/-}$" to read -- β2 m$^{-/-}$ --

Signed and Sealed this
Second Day of August, 2011

David J. Kappos
*Director of the United States Patent and Trademark Office*